United States Patent [19]
Armitage et al.

[11] Patent Number: 6,087,329
[45] Date of Patent: *Jul. 11, 2000

[54] CD40 LIGAND POLYPEPTIDE

[75] Inventors: Richard J. Armitage, Bainbridge Island; William C. Fanslow, Federal Way; Melanie K. Spriggs, Seattle, all of Wash.

[73] Assignee: Immunex Corporation, Seattle, Wash.

[*] Notice: This patent is subject to a terminal disclaimer.

[21] Appl. No.: 09/088,913

[22] Filed: Jun. 2, 1998

Related U.S. Application Data

[60] Division of application No. 08/484,624, Jun. 7, 1995, which is a continuation-in-part of application No. 08/249,189, May 24, 1994, which is a continuation-in-part of application No. 07/969,703, Oct. 23, 1992, abandoned, which is a continuation-in-part of application No. 07/805,723, Dec. 5, 1991, abandoned, which is a continuation-in-part of application No. 07/783,707, Oct. 25, 1991, abandoned.

[51] Int. Cl.⁷ .......................... A61K 38/17; A61K 38/19; C07K 14/435; C07K 14/52
[52] U.S. Cl. ............................ 514/8; 530/350; 530/351; 514/2; 514/885
[58] Field of Search .................................. 530/350, 351; 536/23.5; 514/2, 8, 885

[56] References Cited

U.S. PATENT DOCUMENTS

| | | |
|---|---|---|
| 5,182,368 | 1/1993 | Ledbetter et al. . |
| 5,247,069 | 9/1993 | Ledbetter et al. . |
| 5,474,771 | 12/1995 | Lederman et al. . |

FOREIGN PATENT DOCUMENTS

| | | |
|---|---|---|
| 0 315 062 | 5/1989 | European Pat. Off. . |
| 0 330 191 | 8/1989 | European Pat. Off. . |
| 0 555 880 | 8/1993 | European Pat. Off. . |
| 0 585 943 | 3/1994 | European Pat. Off. . |
| 0 595 659 | 5/1994 | European Pat. Off. . |
| WO 93/09812 | 5/1993 | WIPO . |
| WO 93/23550 | 11/1993 | WIPO . |

OTHER PUBLICATIONS

I. Noelle et al. Immunology Today 13:431–433 1992.
Aruffo and Seed, *Proc. Natl. Acad. Sci. USA* 84:8573, 1987.
Stamenkovic et al., *EMBO J.* 8:1403, 1989.
Zettlmeissl et al., *DNA Cell. Biol.* 9:347, 1990.
Banchereau et al., *Science* 251:70, 1991.
Rousset et al., *J. Exp. Med.* 173:705, 1991.
Banchereau and Rousset, *Clinical Immunology Spectrum* 3:9, 1991.
Liu et al., *Nature* 342:929, 1989.
Ghaderi et al., *Immunology* 73:510, 1991.
Kikutani et al., *Cell* 47:657, 1986.
Wang et al., *J. Virol.* 65:4101, 1991.
Valle et al., *Eur. J. Immunol.* 19:1463, 1989.
Clark et al., *Proc. Natl. Acad. Sci. USA* 83:4494, 1986.
Paulie et al., *J. Immunol.* 142:590, 1989.
Gordon et al., *Eur. J. Immunol.* 17:1535, 1987.
Jabara et al., *J. Exp. Med.* 172:1861, 1990.
Zhang et al., *J. Immunol.* 146:1836, 1991.
Gascan et al., *J. Immunol.* 147:8, 1991.
Gordon et al., *J. Immunol.* 140:1425, 1988.
Armitage et al., *Nature* 357:80, 1992.
Fanslow et al., *J. Immunol.* 149:655, 1992.
Spriggs et al., *J. Exp. Med.* 176:1543, 1992.
Farrah and Smith, *Nature* 358:26, 1992.
Noelle et al., *Proc. Natl. Acad. Sci. USA* 89:6550, 1992.
Hollenbaugh et al., *EMBO J.* 11:4313, 1992.
Durie et al., *Science* 261:1328; 1993.
Lauzon et al., *Mol. Immunol.* 25:829; 1988.
Graf et al., *Eur. J. Immunol.* 22:3191, 1992.
Potocnik et al., *Scan. J. Immunol.* 31:213; 1990.

*Primary Examiner*—Christina Y. Chan
*Assistant Examiner*—Phillip Gambel
*Attorney, Agent, or Firm*—Janis C. Henry

[57] ABSTRACT

There is disclosed a polypeptide (CD40-L) and DNA sequences, vectors and transformed host cells useful in providing CD40-L polypeptides. More particularly, this invention provides isolated human and murine CD40-L polypeptides that bind to the extracellular binding region of a CD40 receptor.

8 Claims, 21 Drawing Sheets

FIG. 1A

```
  1    CTTTCAGTCAGCATGATAGAAACATACAGCCCAACCTTCCCCCAGATCCGTGGCAACTGGACTTCCAGCG     69
  1                    MetIleGluThrTyrSerGlnProSerProArgSerValAlaThrGlyLeuProAla   19

70    AGCATGAAGATTTTTATGTATTACTTACTGTTTCCTTATCACCCAAATGATTGGATCTGTGCTTTTT      138
 20    SerMetLysIlePheMetTyrLeuLeuThrValPheLeuIleThrGlnMetIleGlySerValLeuPhe      42

139    GCTGTGTATCTTCATAGAAGATTGGATAAGGTCGAAGAGGAAGTAAACCTTCATGAAGATTTTGTATTC    207
 43    AlaValTyrLeuHisArgArgLeuAspLysValGluGluGluValAsnLeuHisGluAspPheValPhe     65

208    ATAAAAAAGCTAAAAGAGAGATGCAACAAAGGAGAAGGATCTTTATCCTTGCTGAACTGTGAGGAGATGAGA  276
 66    IleLysLysLeuLysArgCysAsnLysGlyGluGlySerLeuSerLeuAsnCysGluGluMetArg         88

277    AGGCAATTTGAAGACCTTGTCAAGGATATAACGTTAAACAAAGAGAAAGAGAAAACAGCTTTGAA        345
 89    ArgGlnPheGluAspLeuValLysAspIleThrLeuAsnLysGluGluLysGluLysThrSerPheGlu    111

346    ATGCAAAGAGGTGATGAGGATCCTCAAATTGCAGCACGTTGTAAGCGAAGCTTGTAAGCCAACAGTAATGCAGCA  414
112    MetGlnArgGlyAspGluAspProGlnIleAlaAlaHisValValSerGluAlaAsnSerAsnAlaAla      134

415    TCCGTTCTACAGTGGGCCAAGAAAGGATATTATACCATGAAAAGCAACTTGGTAATGCTTGAAAATGGG    483
135    SerValLeuGlnTrpAlaLysLysArgTyrTyrThrMetLysSerAsnLeuValMetLeuGluAsnGly    157

484    AAACAGCTGACGGTTAAAAGAGAAGGACTCTATTATGTCTACACTCAAGTCACCTTCTGCTCTAATCGG    552
158    LysGlnLeuThrValLysArgGluGlyLeuTyrTyrValTyrThrGlnValThrPheCysSerAsnArg    180

553    GAGCCTTCGAGTCAACGCCCATTCATCGTCGGCCTCTGGCTTGAAGCCCAGTGGATCTGAGAGAATC     621
181    GluProSerSerGlnArgProPheIleValGlyLeuTrpLeuLysProSerSerGlySerGluArgIle    203

622    TTACTCAAGGCGGCAAATACCCACAGTTCCTCCCAGCTTTGCGAGCAGCAGTCTGTTCACTTGGGCGGA    690
204    LeuLeuLysAlaAlaAsnThrHisSerSerGlnLeuCysGluGlnLeuSerValHisLeuGlyLeuGly    226
```

FIG. 1B

```
691  GTGTTTGAATTACAAGCTGGTGCTTCTGTGTTTGTCAACGTGACTGAAGCAAGCCAAGTGATCCACAGA  759
227  ValPheGluLeuGlnLeuAlaGlyAlaSerValPheValAsnValThrGluAlaSerGlnValIleHisArg  249

760  GTTGGCTTCTCATCTTTTGGCTTACTCAAACTCTGAACAGTGCGCTGCCCTAGGCTGCAGCAGGGCTGA  828
250  ValGlyPheSerSerPheGlyLeuLeuLysLeu                                        260

829  TGCTGGCAGTCTCCCCTATACACCAAGTCAGTTAGGCCCTCCCCTGTGTTGAACTGCCTATTTATAACC  897

898  CTAGGATCCTCCCTCATGGAGAACTATTTATTATGTACCCCAAGGCACATAGAGCTGGAATAAGAGAAT  966

967  TACAGGGCAGGCAAAAATCCCAAGGACCCTGCTCCCCTAAGAACTTACAATCTGAAACAGCAACCCCAC  1035

1036 TGATTCAGACAACCAGACAGTTTTGTTGTTTATGGGTGTGTCGTTCAATGGACAGAGCTCTGATGAAACAACAGATA  1104

1105 ACTAATGAGCCACAGTTTTGTTGTTTATGGGTGTGTCGTTCAATGGACAGAGTGTACTTGACTTACCAGGG  1173

1174 AAGATGCAGAAGGGCAACTGTGAGCCTCAGCTCACAATCTGTTATGGTTGACCTGGGCTCCCTGCGGCC  1242

1243 CTAGTAGG  1250
```

FIG. 2A

```
  1   TGCCACCTTCTCTGCCAGAAGATACCATTTCAACTTTAACACAGCATGATGAAACATACAACCAAACT           69
  1                                              MetIleGluThrTyrAsnGlnThr            8

70   TCTCCCCGATCTGCGGCCACTGGACTGCCCATCAGCATGAAAATTTTTATGTATTACTTACTGTTTT          138
  9   SerProArgSerAlaAlaThrGlyLeuProIleSerMetLysIlePheMetTyrLeuLeuThrValPhe          31

139   CTTATCACCCAGATGATTGGGTCAGCACTTTTTGCTGTGTATCTTCATAGAAGGTTGGACAAGATAGAA        207
 32   LeuIleThrGlnMetIleGlySerAlaLeuPheAlaValTyrLeuHisArgArgLeuAspLysIleGlu          54

208   GATGAAAGGAATCTTCATGAAGATTTTGTATTCATGAAAACGATACAGAGATGCAACACAGGAGAAAGA        276
 55   AspGluArgAsnLeuHisGluAspPheValPheMetLysThrIleGlnArgCysAsnThrGlyGluArg         77

277   TCCTTATCCTTACTGAACTGTGAGGAGATTAAAGCCAGTTTGAAGGCTTTGAAGGATATAATGTTA          345
 78   SerLeuSerLeuAsnCysGluGluIleLysSerGlnPheGluGlyPheValLysAspIleMetLeu           100

346   AACAAAGAGGAGACGAAGAAAGAAACAGCTTTGAAATGCAAAAAGTGATCAGAATCCTCAAATTGCG        414
101   AsnLysGluGluThrLysLysGluAsnSerPheGluMetGlnLysGlyAspGlnAsnProGlnIleAla         123

415   GCACATGTCATAAGTGAGGCCAGCAGTAAAACAACATCTGTGTTACAGTGGGCTGAAAAAGGATACTAC        483
124   AlaHisValIleSerGluAlaSerSerLysThrThrSerValLeuGlnTrpAlaGluLysGlyTyrTyr         146

484   ACCATGAGCAACAACTGGTAACCCTGGAAAATGGGAAACAGCTGACCGTTAAAAGACAAGGACTCTAT        552
147   ThrMetSerAsnAsnLeuValThrLeuGluAsnGlyLysGlnLeuThrValLysArgGlnGlyLeuTyr         169

553   TATATCTATGCCAAGTCCACCTTCTGTTCCAATCGGGAAGCTTCAAGCTCCATTTATAGCCAGC           621
170   TyrIleTyrAlaGlnValThrPheCysSerAsnArgGluAlaSerGlnAlaProPheIleAlaSer           192

622   CTCTGCCTAAAGTCCCCGGTAGATTCGAGAGAATCTTACTCAGAGCTGCAAATACCCACAGTTCCGCC       690
193   LeuCysLeuLysSerProGlyArgPheGluArgIleLeuLeuArgAlaAlaAsnThrHisSerSerAla        215
```

FIG. 2B

```
691  AAACCTTGCGGGCAACAATCCATTCACTTGGGAGGAGTATTTGAATTGCAACCAGGTGCTTCGGTGTTT   759
216  LysProCysGlyGlnGlnSerIleHisLeuGlyGlyValPheGluLeuGlnProGlyAlaSerValPhe  238

760  GTCAATGTGACTGATCCAAGCCAAGTGAGCCATGGCACTGGCTTCACGTCCTTTGGCTTACTCAAACTC  828
239  ValAsnValThrAspProSerGlnValSerHisGlyThrGlyPheThrSerPheGlyLeuLeuLysLeu  261

829  TGAACAGTGTCACCTTGCAGGCTGTGGTGGAGCTGACGCTGGAGTCTTCATAATACAGCACAGCGGTT   897

898  AAGCCCCACCCCCTGTTAACTGCCTATTTATAACCCTAGGATCCCTCCTTATGGAGAACTATTTAT    961
```

FIG. 3

```
  1  MIETYNQTSPRSAATGLPISMKIFMYLLTVFLITQMIGSALFAVYLHRRL--------  50
  5  MIETYSQPSPRSVATGLPASMKIFMYLLTVFLITQMIGSVLFAVYLHRRL--------  54

51  DKIEDERNLHEDFVFMKTIQRCNTGERSLSLLNCEEIKSQFEGFVKDIML--------  100
 55  DKVEEEVNLHEDFVFIKKLKRCNKGEGSLSLLNCEEMRRQFEDLVKDITL--------  104

101  NKEETKKENSFEMQKGDQNPQIAAHVISEASSKTTSVLQWAEKGYYTMSN--.----- 150
105  NKEE.KKENSFEMQRGDEDPQIAAHVVSEANSNAASVLQWAKKGYYTMKS--.----- 153

151  NLVTLENGKQLTVKRQGLYYIYAQVTFCSNREASSQAPFIASLCLKSPGR--.----- 200
154  NLVMLENGKQLTVKREGLYYVVYTQVTFCSNREPSSQRPFIVGLWLKPSSG--.----- 203

201  FERILLRAANTHSSAKPCGQQSIHLGGVFELQPGASVFNVTDPSQVSHG--.-----  250
204  SERILLKAANTHSSSQLCEQQSVHLGGVFELQAGASVFNVTEASQVIHR--.-----  253

251  TGFTSFGLLKL  261
254  .VGFSSFGLLKL  264
```

PB E + IL-4 + CV1 d7 Proliferation

—○— HAV
—●— CD40L

Induction of B Cell Proliferation by CD40 Ligand Expressing CV-1 Cells (fixed)

Induction of B Cell Proliferation by CD40 Ligand Expressing CV-1 Cells

— □ — CD40L
— △ — 7A1
— ■ — HAV EO
— ▲ — 7A1 + CD40Fc
— ○ — CD40Fc

Induction of Murine B Cell Proliferation by CD40 Ligand Expressing CV-1 Cels (fixed)

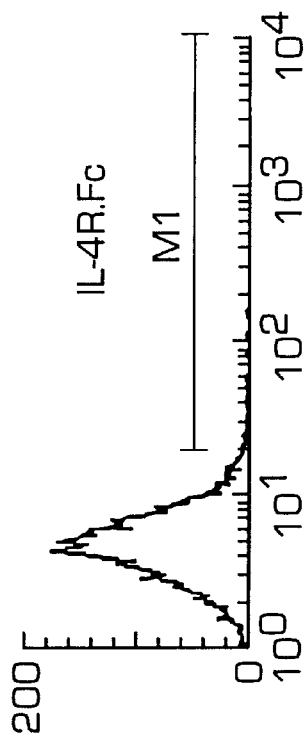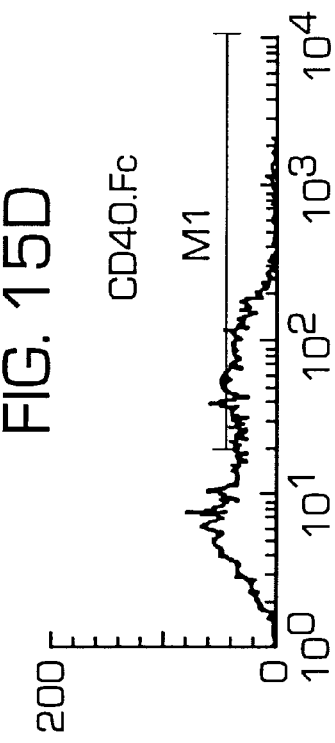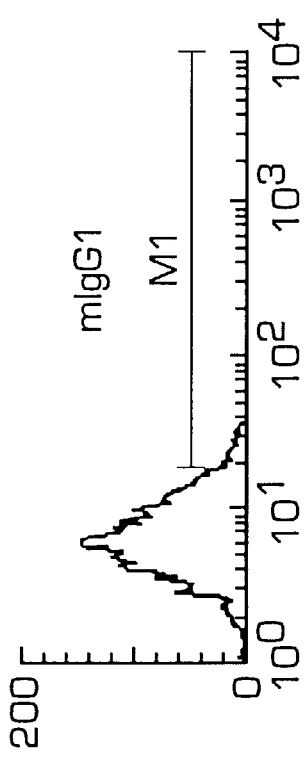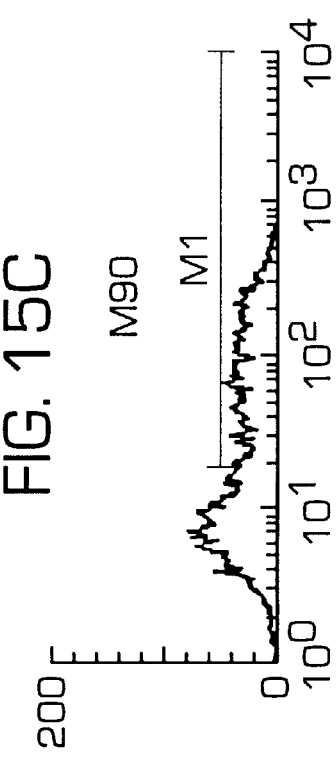
BINDING OF CD40.Fc AND ANTI-CD40L ANTIBODY M90 TO ACTIVATED PERIPHERAL BLOOD T CELLS INHIBITON OF CD40.Fc BINDING TO ACTIVATED PERIPHERAL BLOOD T CELLS BY ANTI-CD40L ANTIBODIES M90 AND M91

BINDING OF CD40 LIGANDS TO CD40Fc USING EQUILIBRIUM
BINDING VALUES ESTIMATED FROM A KINETIC ANALYSIS
OF THE ASSOCIATION PHASE

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 783 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: MOUSE (vii) IMMEDIATE SOURCE:
      (B) CLONE: CD40-L (ix) FEATURE:
      (A) NAME/KEY: CDS
      (B) LOCATION: 1..783

(xi) SEQUENCE DESCRIPTION: SEQ ID NO:1:

```
ATG ATA GAA ACA TAC AGC CAA CCT TCC CCC AGA TCC GTG GCA ACT GGA        48
Met Ile Glu Thr Tyr Ser Gln Pro Ser Pro Arg Ser Val Ala Thr Gly
 1               5                  10                  15

CTT CCA GCG AGC ATG AAG ATT TTT ATG TAT TTA CTT ACT GTT TTC CTT        96
Leu Pro Ala Ser Met Lys Ile Phe Met Tyr Leu Leu Thr Val Phe Leu
                20                  25                  30

ATC ACC CAA ATG ATT GGA TCT GTG CTT TTT GCT GTG TAT CTT CAT AGA       144
Ile Thr Gln Met Ile Gly Ser Val Leu Phe Ala Val Tyr Leu His Arg
            35                  40                  45

AGA TTG GAT AAG GTC GAA GAG GAA GTA AAC CTT CAT GAA GAT TTT GTA       192
Arg Leu Asp Lys Val Glu Glu Glu Val Asn Leu His Glu Asp Phe Val
     50                  55                  60

TTC ATA AAA AAG CTA AAG AGA TGC AAC AAA GGA GAA GGA TCT TTA TCC       240
Phe Ile Lys Lys Leu Lys Arg Cys Asn Lys Gly Glu Gly Ser Leu Ser
 65                  70                  75                  80

TTG CTG AAC TGT GAG GAG ATG AGA AGG CAA TTT GAA GAC CTT GTC AAG       288
Leu Leu Asn Cys Glu Glu Met Arg Arg Gln Phe Glu Asp Leu Val Lys
                 85                  90                  95

GAT ATA ACG TTA AAC AAA GAA GAG AAA AAA GAA AAC AGC TTT GAA ATG       336
Asp Ile Thr Leu Asn Lys Glu Glu Lys Lys Glu Asn Ser Phe Glu Met
            100                 105                 110

CAA AGA GGT GAT GAG GAT CCT CAA ATT GCA GCA CAC GTT GTA AGC GAA       384
Gln Arg Gly Asp Glu Asp Pro Gln Ile Ala Ala His Val Val Ser Glu
        115                 120                 125

GCC AAC AGT AAT GCA GCA TCC GTT CTA CAG TGG GCC AAG AAA GGA TAT       432
Ala Asn Ser Asn Ala Ala Ser Val Leu Gln Trp Ala Lys Lys Gly Tyr
    130                 135                 140

TAT ACC ATG AAA AGC AAC TTG GTA ATG CTT GAA AAT GGG AAA CAG CTG       480
Tyr Thr Met Lys Ser Asn Leu Val Met Leu Glu Asn Gly Lys Gln Leu
145                 150                 155                 160

ACG GTT AAA AGA GAA GGA CTC TAT TAT GTC TAC ACT CAA GTC ACC TTC       528
Thr Val Lys Arg Glu Gly Leu Tyr Tyr Val Tyr Thr Gln Val Thr Phe
                165                 170                 175

TGC TCT AAT CGG GAG CCT TCG AGT CAA CGC CCA TTC ATC GTC GGC CTC       576
```

```
Cys Ser Asn Arg Glu Pro Ser Ser Gln Arg Pro Phe Ile Val Gly Leu
            180                 185                 190

TGG CTG AAG CCC AGC AGT GGA TCT GAG AGA ATC TTA CTC AAG GCG GCA         624
Trp Leu Lys Pro Ser Ser Gly Ser Glu Arg Ile Leu Leu Lys Ala Ala
            195                 200                 205

AAT ACC CAC AGT TCC TCC CAG CTT TGC GAG CAG CAG TCT GTT CAC TTG         672
Asn Thr His Ser Ser Ser Gln Leu Cys Glu Gln Gln Ser Val His Leu
            210                 215                 220

GGC GGA GTG TTT GAA TTA CAA GCT GGT GCT TCT GTG TTT GTC AAC GTG         720
Gly Gly Val Phe Glu Leu Gln Ala Gly Ala Ser Val Phe Val Asn Val
225                 230                 235                 240

ACT GAA GCA AGC CAA GTG ATC CAC AGA GTT GGC TTC TCA TCT TTT GGC         768
Thr Glu Ala Ser Gln Val Ile His Arg Val Gly Phe Ser Ser Phe Gly
                245                 250                 255

TTA CTC AAA CTC TGA                                                     783
Leu Leu Lys Leu
            260
```

(2) INFORMATION FOR SEQ ID NO:2:

(i) SEQUENCE CHARACTERISTICS:
        (A) LENGTH: 260 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ile Glu Thr Tyr Ser Gln Pro Ser Pro Arg Ser Val Ala Thr Gly
 1               5                  10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
            35                  40                  45

Arg Leu Asp Lys Val Glu Glu Val Asn Leu His Glu Asp Phe Val
        50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
            115                 120                 125

Ala Asn Ser Asn Ala Ala Ser Val Leu Gln Trp Ala Lys Lys Gly Tyr
            130                 135                 140

Tyr Thr Met Lys Ser Asn Leu Val Met Leu Glu Asn Gly Lys Gln Leu
145                 150                 155                 160

Thr Val Lys Arg Glu Gly Leu Tyr Tyr Val Tyr Thr Gln Val Thr Phe
                165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
            195                 200                 205

Asn Thr His Ser Ser Ser Gln Leu Cys Glu Gln Gln Ser Val His Leu
            210                 215                 220

Gly Gly Val Phe Glu Leu Gln Ala Gly Ala Ser Val Phe Val Asn Val
225                 230                 235                 240
```

```
Thr Glu Ala Ser Gln Val Ile His Arg Val Gly Phe Ser Ser Phe Gly
            245                 250                 255

Leu Leu Lys Leu
            260

(2) INFORMATION FOR SEQ ID NO:3:

(i) SEQUENCE CHARACTERISTICS:
         (A) LENGTH: 740 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: HUMAN (vii) IMMEDIATE SOURCE:
         (B) CLONE: IgG1 Fc (xi) SEQUENCE DESCRIPTION: SEQ ID NO:3:

CGGTACCGCT AGCGTCGACA GGCCTAGGAT ATCGATACGT AGAGCCCAGA TCTTGTGACA       60

AAACTCACAC ATGCCCACCG TGCCCAGCAC CTGAACTCCT GGGGGGACCG TCAGTCTTCC      120

TCTTCCCCCC AAAACCCAAG GACACCCTCA TGATCTCCCG GACCCCTGAG GTCACATGCG      180

TGGTGGTGGA CGTGAGCCAC GAAGACCCTG AGGTCAAGTT CAACTGGTAC GTGGACGGCG      240

TGGAGGTGCA TAATGCCAAG ACAAAGCCGC GGGAGGAGCA GTACAACAGC ACGTACCGGG      300

TGGTCAGCGT CCTCACCGTC CTGCACCAGG ACTGGCTGAA TGGCAAGGAC TACAAGTGCA      360

AGGTCTCCAA CAAAGCCCTC CCAGCCCCCA TCGAGAAAAC CATCTCCAAA GCCAAAGGGC      420

AGCCCCGAGA ACCACAGGTG TACACCCTGC CCCCATCCCG GGATGAGCTG ACCAAGAACC      480

AGGTCAGCCT GACCTGCCTG GTCAAAGGCT TCTATCCCAG CGACATCGCC GTGGAGTGGG      540

AGAGCAATGG GCAGCCGGAG AACAACTACA AGACCACGCC TCCCGTGCTG GACTCCGACG      600

GCTCCTTCTT CCTCTACAGC AAGCTCACCG TGGACAAGAG CAGGTGGCAG CAGGGGAACG      660

TCTTCTCATG CTCCGTGATG CATGAGGCTC TGCACAACCA CTACACGCAG AAGAGCCTCT      720

CCCTGTCTCC GGGTAAATGA                                                 740

(2) INFORMATION FOR SEQ ID NO:4:

(i) SEQUENCE CHARACTERISTICS:
         (A) LENGTH: 519 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: HUMAN (vii) IMMEDIATE SOURCE:
         (B) CLONE: CD40 EXTRACELLULAR REGION (xi) SEQUENCE DESCRIPTION: SEQ ID NO:4:
```

```
CAGAACCACC CACTGCATGC AGAGAAAAAC AGTACCTAAT AAACAGTCAG TGCTGTTCTT        60

TGTGCCAGCC AGGACAGAAA CTGGTGAGTG ACTGCACAGA GTTCACTGAA ACGGAATGCC       120

TTCCTTGCGG TGAAAGCGAA TTCCTAGACA CCTGGAACAG AGAGACACAC TGCCACCAGC       180

ACAAATACTG CGACCCCAAC CTAGGGCTTC GGGTCCAGCA GAAGGGCACC TCAGAAACAG       240

ACACCATCTG CACCTGTGAA GAAGGCTGGC ACTGTACGAG TGAGGCCTGT GAGAGCTGTG       300

TCCTGCACCG CTCATGCTCG CCCGGCTTTG GGTCAAGCA GATTGCTACA GGGGTTTCTG        360

ATACCATCTG CGAGCCCTGC CCAGTCGGCT TCTTCTCCAA TGTGTCATCT GCTTTCGAAA       420

AATGTCACCC TTGGACAAGC TGTGAGACCA AAGACCTGGT TGTGCAACAG GCAGGCACAA       480

ACAAGACTGA TGTTGTCTGT GGTCCCCAGG ATCGGCTGA                              519
```

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: PCR PRIMER (vii) IMMEDIATE SOURCE:
        (B) CLONE: CD40 5' PRIMER (xi) SEQUENCE DESCRIPTION: SEQ ID NO:5:

```
CCGTCGACCA CCATGGTTCG TCTGCC                                             26
```

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: PCR PRIMER (vii) IMMEDIATE SOURCE:
        (B) CLONE: CD40 3' PRIMER (xi) SEQUENCE DESCRIPTION: SEQ ID NO:6:

```
CCGTCGACGT CTAGAGCCGA TCCTGGGG                                           28
```

(2) INFORMATION FOR SEQ ID NO:7:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA

```
        (iii) HYPOTHETICAL: NO (vi) ORIGINAL SOURCE:
              (A) ORGANISM: PCR PRIMER (vii) IMMEDIATE SOURCE:
              (B) CLONE: CD40 3' DOWNSTREAM PRIMER (xi) SEQUENCE DESCRIPTION: SEQ ID NO:7:

ACAAGATCTG GGCTCTACGT ACTCAGCCGA TCCTGGGGAC                              40

(2) INFORMATION FOR SEQ ID NO:8:

(i) SEQUENCE CHARACTERISTICS:
              (A) LENGTH: 5 amino acids
              (B) TYPE: amino acid
              (D) TOPOLOGY: linear (ii) MOLECULE TYPE: peptide (iii) HYPOTHETICAL: NO (v) FRAGMENT TYPE: internal (vi) ORIGINAL SOURCE:
              (A) ORGANISM: PENTAPEPTIDE (xi) SEQUENCE DESCRIPTION: SEQ ID NO:8:

Tyr Val Gly Pro Arg
1               5

(2) INFORMATION FOR SEQ ID NO:9:

(i) SEQUENCE CHARACTERISTICS:
              (A) LENGTH: 43 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (vi) ORIGINAL SOURCE:
              (A) ORGANISM: PCR PRIMER (vii) IMMEDIATE SOURCE:
              (B) CLONE: HUMAN IGG1/FC 5' PRIMER (xi) SEQUENCE DESCRIPTION: SEQ ID NO:9:

TATTAATCAT TCAGTAGGGC CCAGATCTTG TGACAAAACT CAC                          43

(2) INFORMATION FOR SEQ ID NO:10:

(i) SEQUENCE CHARACTERISTICS:
              (A) LENGTH: 38 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (vi) ORIGINAL SOURCE:
              (A) ORGANISM: PCR PRIMER (vii) IMMEDIATE SOURCE:
              (B) CLONE: HUMAN IGG1/FC 3' DOWNSTREAM PRIMER (xi) SEQUENCE DESCRIPTION: SEQ ID NO:10:
```

GCCAGCTTAA CTAGTTCATT TACCCGGAGA CAGGGAGA                                      38

(2) INFORMATION FOR SEQ ID NO:11:

(i) SEQUENCE CHARACTERISTICS:
        (A) LENGTH: 840 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (vii) IMMEDIATE SOURCE:
        (B) CLONE: CD40-L (ix) FEATURE:
        (A) NAME/KEY: CDS
        (B) LOCATION: 46..831

(xi) SEQUENCE DESCRIPTION: SEQ ID NO:11:

```
TGCCACCTTC TCTGCCAGAA GATACCATTT CAACTTTAAC ACAGC ATG ATC GAA              54
                                                 Met Ile Glu
                                                  1

ACA TAC AAC CAA ACT TCT CCC CGA TCT GCG GCC ACT GGA CTG CCC ATC          102
Thr Tyr Asn Gln Thr Ser Pro Arg Ser Ala Ala Thr Gly Leu Pro Ile
    5                  10                  15

AGC ATG AAA ATT TTT ATG TAT TTA CTT ACT GTT TTT CTT ATC ACC CAG          150
Ser Met Lys Ile Phe Met Tyr Leu Leu Thr Val Phe Leu Ile Thr Gln
 20                  25                  30                  35

ATG ATT GGG TCA GCA CTT TTT GCT GTG TAT CTT CAT AGA AGG TTG GAC          198
Met Ile Gly Ser Ala Leu Phe Ala Val Tyr Leu His Arg Arg Leu Asp
                40                  45                  50

AAG ATA GAA GAT GAA AGG AAT CTT CAT GAA GAT TTT GTA TTC ATG AAA          246
Lys Ile Glu Asp Glu Arg Asn Leu His Glu Asp Phe Val Phe Met Lys
             55                  60                  65

ACG ATA CAG AGA TGC AAC ACA GGA GAA AGA TCC TTA TCC TTA CTG AAC          294
Thr Ile Gln Arg Cys Asn Thr Gly Glu Arg Ser Leu Ser Leu Leu Asn
         70                  75                  80

TGT GAG GAG ATT AAA AGC CAG TTT GAA GGC TTT GTG AAG GAT ATA ATG          342
Cys Glu Glu Ile Lys Ser Gln Phe Glu Gly Phe Val Lys Asp Ile Met
     85                  90                  95

TTA AAC AAA GAG GAG ACG AAG AAA GAA AAC AGC TTT GAA ATG CAA AAA          390
Leu Asn Lys Glu Glu Thr Lys Lys Glu Asn Ser Phe Glu Met Gln Lys
100                 105                 110                 115

GGT GAT CAG AAT CCT CAA ATT GCG GCA CAT GTC ATA AGT GAG GCC AGC          438
Gly Asp Gln Asn Pro Gln Ile Ala Ala His Val Ile Ser Glu Ala Ser
                120                 125                 130

AGT AAA ACA ACA TCT GTG TTA CAG TGG GCT GAA AAA GGA TAC TAC ACC          486
Ser Lys Thr Thr Ser Val Leu Gln Trp Ala Glu Lys Gly Tyr Tyr Thr
            135                 140                 145

ATG AGC AAC AAC TTG GTA ACC CTG GAA AAT GGG AAA CAG CTG ACC GTT          534
Met Ser Asn Asn Leu Val Thr Leu Glu Asn Gly Lys Gln Leu Thr Val
        150                 155                 160

AAA AGA CAA GGA CTC TAT TAT ATC TAT GCC CAA GTC ACC TTC TGT TCC          582
Lys Arg Gln Gly Leu Tyr Tyr Ile Tyr Ala Gln Val Thr Phe Cys Ser
    165                 170                 175

AAT CGG GAA GCT TCG AGT CAA GCT CCA TTT ATA GCC AGC CTC TGC CTA          630
```

| | | | | | | | | | | | | | | |
|---|---|---|---|---|---|---|---|---|---|---|---|---|---|---|
|Asn|Arg|Glu|Ala|Ser|Ser|Gln|Ala|Pro|Phe|Ile|Ala|Ser|Leu|Cys|Leu|
|180| | | | |185| | | |190| | | |195| |

```
AAG TCC CCC GGT AGA TTC GAG AGA ATC TTA CTC AGA GCT GCA AAT ACC    678
Lys Ser Pro Gly Arg Phe Glu Arg Ile Leu Leu Arg Ala Ala Asn Thr
            200                 205                 210

CAC AGT TCC GCC AAA CCT TGC GGG CAA CAA TCC ATT CAC TTG GGA GGA    726
His Ser Ser Ala Lys Pro Cys Gly Gln Gln Ser Ile His Leu Gly Gly
                215                 220                 225

GTA TTT GAA TTG CAA CCA GGT GCT TCG GTG TTT GTC AAT GTG ACT GAT    774
Val Phe Glu Leu Gln Pro Gly Ala Ser Val Phe Val Asn Val Thr Asp
            230                 235                 240

CCA AGC CAA GTG AGC CAT GGC ACT GGC TTC ACG TCC TTT GGC TTA CTC    822
Pro Ser Gln Val Ser His Gly Thr Gly Phe Thr Ser Phe Gly Leu Leu
245                 250                 255

AAA CTC TGAACAGTGT CA                                              840
Lys Leu
260
```

(2) INFORMATION FOR SEQ ID NO:12:

(i) SEQUENCE CHARACTERISTICS:
        (A) LENGTH: 261 amino acids
        (B) TYPE: amino acid
        (D) TOPOLOGY: linear (ii) MOLECULE TYPE: protein (xi) SEQUENCE DESCRIPTION: SEQ ID NO:12:

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240
```

```
Val Thr Asp Pro Ser Gln Val Ser His Gly Thr Gly Phe Thr Ser Phe
            245                 250                 255

Gly Leu Leu Lys Leu
            260
```

(2) INFORMATION FOR SEQ ID NO:13:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:13:

```
TGGTGGCGGA GGGTCAGGCG GAGGTGGGTC CGGAGGCGGG GGTTCAAGTT CTGACAAGAT       60

AGAAGATGAA AGG                                                         73
```

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:14:

```
GGCCGCTCAG AGTTTGAGTA A                                                21
```

(2) INFORMATION FOR SEQ ID NO:15:

(i) SEQUENCE CHARACTERISTICS:
        (A) LENGTH: 1425 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vii) IMMEDIATE SOURCE:
        (B) CLONE: Human CD40-L/FC2 (soluble CD40-L)

(ix) FEATURE:
        (A) NAME/KEY: CDS
        (B) LOCATION: 4..1422

(ix) FEATURE:
        (A) NAME/KEY: mat_peptide
        (B) LOCATION: 79..1422

(ix) FEATURE:
        (A) NAME/KEY: sig_peptide
        (B) LOCATION: 4..78

(xi) SEQUENCE DESCRIPTION: SEQ ID NO:15:

```
TAT ATG TTC CAT GTT TCT TTT AGA TAT ATC TTT GGA ATT CCT CCA CTG         48
    Met Phe His Val Ser Phe Arg Tyr Ile Phe Gly Ile Pro Pro Leu
    -25             -20             -15

ATC CTT GTT CTG CTG CCT GTC ACT AGC TCT GAC TAC AAA GAT GAC GAT         96
Ile Leu Val Leu Leu Pro Val Thr Ser Ser Asp Tyr Lys Asp Asp Asp
-10             -5                    1                5

GAT AAA AGA TCT TGT GAC AAA ACT CAC ACA TGC CCA CCG TGC CCA GCA        144
Asp Lys Arg Ser Cys Asp Lys Thr His Thr Cys Pro Pro Cys Pro Ala
            10              15              20

CCT GAA CTC CTG GGG GGA CCG TCA GTC TTC CTC TTC CCC CCA AAA CCC        192
Pro Glu Leu Leu Gly Gly Pro Ser Val Phe Leu Phe Pro Pro Lys Pro
        25              30              35

AAG GAC ACC CTC ATG ATC TCC CGG ACC CCT GAG GTC ACA TGC GTG GTG        240
Lys Asp Thr Leu Met Ile Ser Arg Thr Pro Glu Val Thr Cys Val Val
    40              45              50

GTG GAC GTG AGC CAC GAA GAC CCT GAG GTC AAG TTC AAC TGG TAC GTG        288
Val Asp Val Ser His Glu Asp Pro Glu Val Lys Phe Asn Trp Tyr Val
55              60              65              70

GAC GGC GTG GAG GTG CAT AAT GCC AAG ACA AAG CCG CGG GAG GAG CAG        336
Asp Gly Val Glu Val His Asn Ala Lys Thr Lys Pro Arg Glu Glu Gln
                75              80              85

TAC AAC AGC ACG TAC CGG GTG GTC AGC GTC CTC ACC GTC CTG CAC CAG        384
Tyr Asn Ser Thr Tyr Arg Val Val Ser Val Leu Thr Val Leu His Gln
            90              95              100

GAC TGG CTG AAT GGC AAG GAG TAC AAG TGC AAG GTC TCC AAC AAA GCC        432
Asp Trp Leu Asn Gly Lys Glu Tyr Lys Cys Lys Val Ser Asn Lys Ala
        105             110             115

CTC CCA GCC CCC ATC GAG AAA ACC ATC TCC AAA GCC AAA GGG CAG CCC        480
Leu Pro Ala Pro Ile Glu Lys Thr Ile Ser Lys Ala Lys Gly Gln Pro
    120             125             130

CGA GAA CCA CAG GTG TAC ACC CTG CCC CCA TCC CGG GAT GAG CTG ACC        528
Arg Glu Pro Gln Val Tyr Thr Leu Pro Pro Ser Arg Asp Glu Leu Thr
135             140             145             150

AAG AAC CAG GTC AGC CTG ACC TGC CTG GTC AAA GGC TTC TAT CCC AGC        576
Lys Asn Gln Val Ser Leu Thr Cys Leu Val Lys Gly Phe Tyr Pro Ser
                155             160             165

GAC ATC GCC GTG GAG TGG GAG AGC AAT GGG CAG CCG GAG AAC AAC TAC        624
Asp Ile Ala Val Glu Trp Glu Ser Asn Gly Gln Pro Glu Asn Asn Tyr
            170             175             180

AAG ACC ACG CCT CCC GTG CTG GAC TCC GAC GGC TCC TTC TTC CTC TAC        672
Lys Thr Thr Pro Pro Val Leu Asp Ser Asp Gly Ser Phe Phe Leu Tyr
        185             190             195

AGC AAG CTC ACC GTG GAC AAG AGC AGG TGG CAG CAG GGG AAC GTC TTC        720
Ser Lys Leu Thr Val Asp Lys Ser Arg Trp Gln Gln Gly Asn Val Phe
    200             205             210

TCA TGC TCC GTG ATG CAT GGT GGC GGA GGG TCA GGC GGA GGT GGG TCC        768
Ser Cys Ser Val Met His Gly Gly Gly Gly Ser Gly Gly Gly Gly Ser
215             220             225             230

GGA GGC GGG GGT TCA AGT TCT GAC AAG ATA GAA GAT GAA AGG AAT CTT        816
Gly Gly Gly Gly Ser Ser Ser Asp Lys Ile Glu Asp Glu Arg Asn Leu
                235             240             245

CAT GAA GAT TTT GTA TTC ATG AAA ACG ATA CAG AGA TGC AAC ACA GGA        864
His Glu Asp Phe Val Phe Met Lys Thr Ile Gln Arg Cys Asn Thr Gly
            250             255             260

GAA AGA TCC TTA TCC TTA CTG AAC TGT GAG GAG ATT AAA AGC CAG TTT        912
Glu Arg Ser Leu Ser Leu Leu Asn Cys Glu Glu Ile Lys Ser Gln Phe
        265             270             275

GAA GGC TTT GTG AAG GAT ATA ATG TTA AAC AAA GAG GAG ACG AAG AAA        960
Glu Gly Phe Val Lys Asp Ile Met Leu Asn Lys Glu Glu Thr Lys Lys
    280             285             290
```

```
GAA AAC AGC TTT GAA ATG CAA AAA GGT GAT CAG AAT CCT CAA ATT GCG       1008
Glu Asn Ser Phe Glu Met Gln Lys Gly Asp Gln Asn Pro Gln Ile Ala
295                 300                 305                 310

GCA CAT GTC ATA AGT GAG GCC AGC AGT AAA ACA ACA TCT GTG TTA CAG       1056
Ala His Val Ile Ser Glu Ala Ser Ser Lys Thr Thr Ser Val Leu Gln
                315                 320                 325

TGG GCT GAA AAA GGA TAC TAC ACC ATG AGC AAC AAC TTG GTA ACC CTG       1104
Trp Ala Glu Lys Gly Tyr Tyr Thr Met Ser Asn Asn Leu Val Thr Leu
            330                 335                 340

GAA AAT GGG AAA CAG CTG ACC GTT AAA AGA CAA GGA CTC TAT TAT ATC       1152
Glu Asn Gly Lys Gln Leu Thr Val Lys Arg Gln Gly Leu Tyr Tyr Ile
        345                 350                 355

TAT GCC CAA GTC ACC TTC TGT TCC AAT CGG GAA GCT TCG AGT CAA GCT       1200
Tyr Ala Gln Val Thr Phe Cys Ser Asn Arg Glu Ala Ser Ser Gln Ala
    360                 365                 370

CCA TTT ATA GCC AGC CTC TGC CTA AAG TCC CCC GGT AGA TTC GAG AGA       1248
Pro Phe Ile Ala Ser Leu Cys Leu Lys Ser Pro Gly Arg Phe Glu Arg
375                 380                 385                 390

ATC TTA CTC AGA GCT GCA AAT ACC CAC AGT TCC GCC AAA CCT TGC GGG       1296
Ile Leu Leu Arg Ala Ala Asn Thr His Ser Ser Ala Lys Pro Cys Gly
                395                 400                 405

CAA CAA TCC ATT CAC TTG GGA GGA GTA TTT GAA TTG CAA CCA GGT GCT       1344
Gln Gln Ser Ile His Leu Gly Gly Val Phe Glu Leu Gln Pro Gly Ala
            410                 415                 420

TCG GTG TTT GTC AAT GTG ACT GAT CCA AGC CAA GTG AGC CAT GGC ACT       1392
Ser Val Phe Val Asn Val Thr Asp Pro Ser Gln Val Ser His Gly Thr
        425                 430                 435

GGC TTC ACG TCC TTT GGC TTA CTC AAA CTC TGA                           1425
Gly Phe Thr Ser Phe Gly Leu Leu Lys Leu
    440                 445
```

(2) INFORMATION FOR SEQ ID NO:16:

(i) SEQUENCE CHARACTERISTICS:
        (A) LENGTH: 473 amino acids
        (B) TYPE: amino acid
        (D) TOPOLOGY: linear (ii) MOLECULE TYPE: protein (xi) SEQUENCE DESCRIPTION: SEQ ID NO:16:

```
Met Phe His Val Ser Phe Arg Tyr Ile Phe Gly Ile Pro Pro Leu Ile
-25                 -20                 -15                 -10

Leu Val Leu Leu Pro Val Thr Ser Ser Asp Tyr Lys Asp Asp Asp Asp
                -5                   1                   5

Lys Arg Ser Cys Asp Lys Thr His Thr Cys Pro Pro Cys Pro Ala Pro
            10                  15                  20

Glu Leu Leu Gly Gly Pro Ser Val Phe Leu Phe Pro Pro Lys Pro Lys
        25                  30                  35

Asp Thr Leu Met Ile Ser Arg Thr Pro Glu Val Thr Cys Val Val Val
40                  45                  50                  55

Asp Val Ser His Glu Asp Pro Glu Val Lys Phe Asn Trp Tyr Val Asp
                60                  65                  70

Gly Val Glu Val His Asn Ala Lys Thr Lys Pro Arg Glu Glu Gln Tyr
            75                  80                  85

Asn Ser Thr Tyr Arg Val Val Ser Val Leu Thr Val Leu His Gln Asp
        90                  95                 100

Trp Leu Asn Gly Lys Glu Tyr Lys Cys Lys Val Ser Asn Lys Ala Leu
    105                 110                 115
```

```
Pro Ala Pro Ile Glu Lys Thr Ile Ser Lys Ala Lys Gly Gln Pro Arg
120                 125                 130                 135

Glu Pro Gln Val Tyr Thr Leu Pro Pro Ser Arg Asp Glu Leu Thr Lys
            140                 145                 150

Asn Gln Val Ser Leu Thr Cys Leu Val Lys Gly Phe Tyr Pro Ser Asp
            155                 160                 165

Ile Ala Val Glu Trp Glu Ser Asn Gly Gln Pro Glu Asn Asn Tyr Lys
        170                 175                 180

Thr Thr Pro Pro Val Leu Asp Ser Asp Gly Ser Phe Phe Leu Tyr Ser
        185                 190                 195

Lys Leu Thr Val Asp Lys Ser Arg Trp Gln Gln Gly Asn Val Phe Ser
200                 205                 210                 215

Cys Ser Val Met His Gly Gly Gly Ser Gly Gly Gly Gly Ser Gly
                220                 225                 230

Gly Gly Gly Ser Ser Asp Lys Ile Glu Asp Glu Arg Asn Leu His
            235                 240                 245

Glu Asp Phe Val Phe Met Lys Thr Ile Gln Arg Cys Asn Thr Gly Glu
            250                 255                 260

Arg Ser Leu Ser Leu Leu Asn Cys Glu Glu Ile Lys Ser Gln Phe Glu
265                 270                 275

Gly Phe Val Lys Asp Ile Met Leu Asn Lys Glu Thr Lys Lys Glu
280                 285                 290                 295

Asn Ser Phe Glu Met Gln Lys Gly Asp Gln Asn Pro Gln Ile Ala Ala
                300                 305                 310

His Val Ile Ser Glu Ala Ser Ser Lys Thr Thr Ser Val Leu Gln Trp
            315                 320                 325

Ala Glu Lys Gly Tyr Tyr Thr Met Ser Asn Asn Leu Val Thr Leu Glu
            330                 335                 340

Asn Gly Lys Gln Leu Thr Val Lys Arg Gln Gly Leu Tyr Tyr Ile Tyr
        345                 350                 355

Ala Gln Val Thr Phe Cys Ser Asn Arg Glu Ala Ser Ser Gln Ala Pro
360                 365                 370                 375

Phe Ile Ala Ser Leu Cys Leu Lys Ser Pro Gly Arg Phe Glu Arg Ile
            380                 385                 390

Leu Leu Arg Ala Ala Asn Thr His Ser Ser Ala Lys Pro Cys Gly Gln
            395                 400                 405

Gln Ser Ile His Leu Gly Gly Val Phe Glu Leu Gln Pro Gly Ala Ser
        410                 415                 420

Val Phe Val Asn Val Thr Asp Pro Ser Gln Val Ser His Gly Thr Gly
        425                 430                 435

Phe Thr Ser Phe Gly Leu Leu Lys Leu
440                 445

(2) INFORMATION FOR SEQ ID NO:17:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (xi) SEQUENCE DESCRIPTION: SEQ ID NO:17:

Arg Met Lys Gln Ile Glu Asp Lys Ile Glu Glu Ile Leu Ser Lys Ile
1               5                   10                  15
```

```
Tyr His Ile Glu Asn Glu Ile Ala Arg Ile Lys Lys Leu Ile Gly Glu
            20                  25                  30
Arg (2) INFORMATION FOR SEQ ID NO:18:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:18:

ATATGAATTC GACTACAAAG ATGACGATGA TAAACCTCAA ATTGCAGCAC ACGTT          55

(2) INFORMATION FOR SEQ ID NO:19:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:19:

CCTTCGCGGC CGCGTTCAGA GTTTGAGTAA GCCAA                                35

(2) INFORMATION FOR SEQ ID NO:20:

(i) SEQUENCE CHARACTERISTICS:
        (A) LENGTH: 929 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Human CD40-L trimer (ix) FEATURE:
        (A) NAME/KEY: sig_peptide
        (B) LOCATION: 65..142

(ix) FEATURE:
        (A) NAME/KEY: CDS
        (B) LOCATION: 65..886

(ix) FEATURE:
        (A) NAME/KEY: mat_peptide
        (B) LOCATION: 143..886

(xi) SEQUENCE DESCRIPTION: SEQ ID NO:20:

TGAGCGAGTC CGCATCGACG GATCGGAAAA CCTCTCCGAG GTACCTATCC CGGGGATCCC     60

CACC ATG TTC CAT GTT TCT TTT AGA TAT ATC TTT GGA ATT CCT CCA CTG    109
     Met Phe His Val Ser Phe Arg Tyr Ile Phe Gly Ile Pro Pro Leu
     -26 -25                 -20                 -15

ATC CTT GTT CTG CTG CCT GTC ACT AGT TCT GAC CGT ATG AAA CAG ATA     157
Ile Leu Val Leu Leu Pro Val Thr Ser Ser Asp Arg Met Lys Gln Ile
```

```
               -10                  -5                    1                    5
        GAG GAT AAG ATC GAA GAG ATC CTA AGT AAG ATT TAT CAT ATA GAG AAT          205
        Glu Asp Lys Ile Glu Glu Ile Leu Ser Lys Ile Tyr His Ile Glu Asn
                             10                  15                  20

GAA ATC GCC CGT ATC AAA AAG CTG ATT GGC GAG CGG ACT AGT TCT GAC          253
        Glu Ile Ala Arg Ile Lys Lys Leu Ile Gly Glu Arg Thr Ser Ser Asp
                        25                  30                  35

AAG ATA GAA GAT GAA AGG AAT CTT CAT GAA GAT TTT GTA TTC ATG AAA          301
        Lys Ile Glu Asp Glu Arg Asn Leu His Glu Asp Phe Val Phe Met Lys
                    40                  45                  50

ACG ATA CAG AGA TGC AAC ACA GGA GAA AGA TCC TTA TCC TTA CTG AAC          349
        Thr Ile Gln Arg Cys Asn Thr Gly Glu Arg Ser Leu Ser Leu Leu Asn
                55                  60                  65

TGT GAG GAG ATT AAA AGC CAG TTT GAA GGC TTT GTG AAG GAT ATA ATG          397
        Cys Glu Glu Ile Lys Ser Gln Phe Glu Gly Phe Val Lys Asp Ile Met
        70                  75                  80                  85

TTA AAC AAA GAG GAG ACG AAG AAA GAA AAC AGC TTT GAA ATG CAA AAA          445
        Leu Asn Lys Glu Glu Thr Lys Lys Glu Asn Ser Phe Glu Met Gln Lys
                        90                  95                  100

GGT GAT CAG AAT CCT CAA ATT GCG GCA CAT GTC ATA AGT GAG GCC AGC          493
        Gly Asp Gln Asn Pro Gln Ile Ala Ala His Val Ile Ser Glu Ala Ser
                    105                 110                 115

AGT AAA ACA ACA TCT GTG TTA CAG TGG GCT GAA AAA GGA TAC TAC ACC          541
        Ser Lys Thr Thr Ser Val Leu Gln Trp Ala Glu Lys Gly Tyr Tyr Thr
                120                 125                 130

ATG AGC AAC AAC TTG GTA ACC CTG GAA AAT GGG AAA CAG CTG ACC GTT          589
        Met Ser Asn Asn Leu Val Thr Leu Glu Asn Gly Lys Gln Leu Thr Val
        135                 140                 145

AAA AGA CAA GGA CTC TAT TAT ATC TAT GCC CAA GTC ACC TTC TGT TCC          637
        Lys Arg Gln Gly Leu Tyr Tyr Ile Tyr Ala Gln Val Thr Phe Cys Ser
        150                 155                 160                 165

AAT CGG GAA GCT TCG AGT CAA GCT CCA TTT ATA GCC AGC CTC TGC CTA          685
        Asn Arg Glu Ala Ser Ser Gln Ala Pro Phe Ile Ala Ser Leu Cys Leu
                        170                 175                 180

AAG TCC CCC GGT AGA TTC GAG AGA ATC TTA CTC AGA GCT GCA AAT ACC          733
        Lys Ser Pro Gly Arg Phe Glu Arg Ile Leu Leu Arg Ala Ala Asn Thr
                    185                 190                 195

CAC AGT TCC GCC AAA CCT TGC GGG CAA CAA TCC ATT CAC TTG GGA GGA          781
        His Ser Ser Ala Lys Pro Cys Gly Gln Gln Ser Ile His Leu Gly Gly
                200                 205                 210

GTA TTT GAA TTG CAA CCA GGT GCT TCG GTG TTT GTC AAT GTG ACT GAT          829
        Val Phe Glu Leu Gln Pro Gly Ala Ser Val Phe Val Asn Val Thr Asp
                215                 220                 225

CCA AGC CAA GTG AGC CAT GGC ACT GGC TTC ACG TCC TTT GGC TTA CTC          877
        Pro Ser Gln Val Ser His Gly Thr Gly Phe Thr Ser Phe Gly Leu Leu
        230                 235                 240                 245

AAA CTC TGAGCGGCCG CTACAGATGA ATAATAAGCA TGTTTGGATT CCTCAA            929
        Lys Leu
```

(2) INFORMATION FOR SEQ ID NO:21:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:21:

```
Met Phe His Val Ser Phe Arg Tyr Ile Phe Gly Ile Pro Pro Leu Ile
-26 -25                 -20                 -15
```

```
Leu Val Leu Leu Pro Val Thr Ser Ser Asp Arg Met Lys Gln Ile Glu
-10                  -5                   1                   5

Asp Lys Ile Glu Glu Ile Leu Ser Lys Ile Tyr His Ile Glu Asn Glu
            10                  15                  20

Ile Ala Arg Ile Lys Lys Leu Ile Gly Glu Arg Thr Ser Ser Asp Lys
        25                  30                  35

Ile Glu Asp Glu Arg Asn Leu His Glu Asp Phe Val Phe Met Lys Thr
    40                  45                  50

Ile Gln Arg Cys Asn Thr Gly Glu Arg Ser Leu Ser Leu Leu Asn Cys
55                  60                  65                  70

Glu Glu Ile Lys Ser Gln Phe Glu Gly Phe Val Lys Asp Ile Met Leu
                75                  80                  85

Asn Lys Glu Glu Thr Lys Lys Glu Asn Ser Phe Glu Met Gln Lys Gly
            90                  95                  100

Asp Gln Asn Pro Gln Ile Ala Ala His Val Ile Ser Glu Ala Ser Ser
        105                 110                 115

Lys Thr Thr Ser Val Leu Gln Trp Ala Glu Lys Gly Tyr Tyr Thr Met
120                 125                 130

Ser Asn Asn Leu Val Thr Leu Glu Asn Gly Lys Gln Leu Thr Val Lys
135                 140                 145                 150

Arg Gln Gly Leu Tyr Tyr Ile Tyr Ala Gln Val Thr Phe Cys Ser Asn
                155                 160                 165

Arg Glu Ala Ser Ser Gln Ala Pro Phe Ile Ala Ser Leu Cys Leu Lys
        170                 175                 180

Ser Pro Gly Arg Phe Glu Arg Ile Leu Leu Arg Ala Ala Asn Thr His
        185                 190                 195

Ser Ser Ala Lys Pro Cys Gly Gln Gln Ser Ile His Leu Gly Gly Val
200                 205                 210

Phe Glu Leu Gln Pro Gly Ala Ser Val Phe Val Asn Val Thr Asp Pro
215                 220                 225                 230

Ser Gln Val Ser His Gly Thr Gly Phe Thr Ser Phe Gly Leu Leu Lys
                235                 240                 245

Leu (2) INFORMATION FOR SEQ ID NO:22:

(i) SEQUENCE CHARACTERISTICS:
        (A) LENGTH: 878 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: Murine CD40-L trimer (ix) FEATURE:
        (A) NAME/KEY: sig_peptide
        (B) LOCATION: 15..92

(ix) FEATURE:
        (A) NAME/KEY: CDS
        (B) LOCATION: 15..857

(ix) FEATURE:
        (A) NAME/KEY: mat_peptide
        (B) LOCATION: 93..857

(xi) SEQUENCE DESCRIPTION: SEQ ID NO:22:
```

```
CTCGAGGTAC CGCC ATG TTC CAT GTT TCT TTT AGA TAT ATC TTT GGA ATT            50
               Met Phe His Val Ser Phe Arg Tyr Ile Phe Gly Ile
               -26 -25              -20              -15

CCT CCA CTG ATC CTT GTT CTG CTG CCT GTC ACT AGT TCT GAC CGT ATG            98
Pro Pro Leu Ile Leu Val Leu Leu Pro Val Thr Ser Ser Asp Arg Met
        -10              -5                           1

AAA CAG ATA GAG GAT AAG ATC GAA GAG ATC CTA AGT AAG ATT TAT CAT           146
Lys Gln Ile Glu Asp Lys Ile Glu Glu Ile Leu Ser Lys Ile Tyr His
         5              10              15

ATA GAG AAT GAA ATC GCC CGT ATC AAA AAG CTG ATT GGC GAG CGG ACT           194
Ile Glu Asn Glu Ile Ala Arg Ile Lys Lys Leu Ile Gly Glu Arg Thr
     20              25              30

AGT TCT GAC TAC AAA GAT GAC GAT GAT AAA GAT AAG GTC GAA GAG GAA           242
Ser Ser Asp Tyr Lys Asp Asp Asp Asp Lys Asp Lys Val Glu Glu Glu
 35              40              45              50

GTA AAC CTT CAT GAA GAT TTT GTA TTC ATA AAA AAG CTA AAG AGA TGC           290
Val Asn Leu His Glu Asp Phe Val Phe Ile Lys Lys Leu Lys Arg Cys
             55              60              65

AAC AAA GGA GAA GGA TCT TTA TCC TTG CTG AAC TGT GAG GAG ATG AGA           338
Asn Lys Gly Glu Gly Ser Leu Ser Leu Leu Asn Cys Glu Glu Met Arg
         70              75              80

AGG CAA TTT GAA GAC CTT GTC AAG GAT ATA ACG TTA AAC AAA GAA GAG           386
Arg Gln Phe Glu Asp Leu Val Lys Asp Ile Thr Leu Asn Lys Glu Glu
         85              90              95

AAA AAA GAA AAC AGC TTT GAA ATG CAA AGA GGT GAT GAG GAT CCT CAA           434
Lys Lys Glu Asn Ser Phe Glu Met Gln Arg Gly Asp Glu Asp Pro Gln
100             105             110

ATT GCA GCA CAC GTT GTA AGC GAA GCC AAC AGT AAT GCA GCA TCC GTT           482
Ile Ala Ala His Val Val Ser Glu Ala Asn Ser Asn Ala Ala Ser Val
115             120             125             130

CTA CAG TGG GCC AAG AAA GGA TAT TAT ACC ATG AAA AGC AAC TTG GTA           530
Leu Gln Trp Ala Lys Lys Gly Tyr Tyr Thr Met Lys Ser Asn Leu Val
            135             140             145

ATG CTT GAA AAT GGG AAA CAG CTG ACG GTT AAA AGA GAA GGA CTC TAT           578
Met Leu Glu Asn Gly Lys Gln Leu Thr Val Lys Arg Glu Gly Leu Tyr
            150             155             160

TAT GTC TAC ACT CAA GTC ACC TTC TGC TCT AAT CGG GAG CCT TCG AGT           626
Tyr Val Tyr Thr Gln Val Thr Phe Cys Ser Asn Arg Glu Pro Ser Ser
            165             170             175

CAA CGC CCA TTC ATC GTC GGC CTC TGG CTG AAG CCC AGC AGT GGA TCT           674
Gln Arg Pro Phe Ile Val Gly Leu Trp Leu Lys Pro Ser Ser Gly Ser
180             185             190

GAG AGA ATC TTA CTC AAG GCG GCA AAT ACC CAC AGT TCC TCC CAG CTT           722
Glu Arg Ile Leu Leu Lys Ala Ala Asn Thr His Ser Ser Ser Gln Leu
195             200             205             210

TGC GAG CAG CAG TCT GTT CAC TTG GGC GGA GTG TTT GAA TTA CAA GCT           770
Cys Glu Gln Gln Ser Val His Leu Gly Gly Val Phe Glu Leu Gln Ala
            215             220             225

GGT GCT TCT GTG TTT GTC AAC GTG ACT GAA GCA AGC CAA GTG ATC CAC           818
Gly Ala Ser Val Phe Val Asn Val Thr Glu Ala Ser Gln Val Ile His
            230             235             240

AGA GTT GGC TTC TCA TCT TTT GGC TTA CTC AAA CTC TGAACGCGGC                864
Arg Val Gly Phe Ser Ser Phe Gly Leu Leu Lys Leu
            245             250             255

CGCTACAGAT CTAC                                                           878

(2) INFORMATION FOR SEQ ID NO:23:

(i) SEQUENCE CHARACTERISTICS:
        (A) LENGTH: 280 amino acids
```

```
            (B) TYPE: amino acid
            (D) TOPOLOGY: linear (ii) MOLECULE TYPE: protein (xi) SEQUENCE DESCRIPTION: SEQ ID NO:23:

Met Phe His Val Ser Phe Arg Tyr Ile Phe Gly Ile Pro Pro Leu Ile
-26 -25             -20                 -15
Leu Val Leu Leu Pro Val Thr Ser Ser Asp Arg Met Lys Gln Ile Glu
-10             -5                  1               5
Asp Lys Ile Glu Glu Ile Leu Ser Lys Ile Tyr His Ile Glu Asn Glu
                10              15              20
Ile Ala Arg Ile Lys Lys Leu Ile Gly Glu Arg Thr Ser Ser Asp Tyr
            25              30              35
Lys Asp Asp Asp Lys Asp Lys Val Glu Glu Val Asn Leu His
        40              45              50
Glu Asp Phe Val Phe Ile Lys Lys Leu Arg Cys Asn Lys Gly Glu
55              60              65              70
Gly Ser Leu Ser Leu Leu Asn Cys Glu Glu Met Arg Arg Gln Phe Glu
            75              80              85
Asp Leu Val Lys Asp Ile Thr Leu Asn Lys Glu Glu Lys Lys Glu Asn
            90              95              100
Ser Phe Glu Met Gln Arg Gly Asp Glu Asp Pro Gln Ile Ala Ala His
            105             110             115
Val Val Ser Glu Ala Asn Ser Asn Ala Ala Ser Val Leu Gln Trp Ala
        120             125             130
Lys Lys Gly Tyr Tyr Thr Met Lys Ser Asn Leu Val Met Leu Glu Asn
135             140             145             150
Gly Lys Gln Leu Thr Val Lys Arg Glu Gly Leu Tyr Tyr Val Tyr Thr
            155             160             165
Gln Val Thr Phe Cys Ser Asn Arg Glu Pro Ser Ser Gln Arg Pro Phe
            170             175             180
Ile Val Gly Leu Trp Leu Lys Pro Ser Ser Gly Ser Glu Arg Ile Leu
            185             190             195
Leu Lys Ala Ala Asn Thr His Ser Ser Ser Gln Leu Cys Glu Gln Gln
200             205             210
Ser Val His Leu Gly Gly Val Phe Glu Leu Gln Ala Gly Ala Ser Val
215             220             225             230
Phe Val Asn Val Thr Glu Ala Ser Gln Val Ile His Arg Val Gly Phe
            235             240             245
Ser Ser Phe Gly Leu Leu Lys Leu
            250

(2) INFORMATION FOR SEQ ID NO:24:

(i) SEQUENCE CHARACTERISTICS:
        (A) LENGTH: 27 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:24:

Pro Asp Val Ala Ser Leu Arg Gln Gln Val Glu Ala Leu Gln Gly Gln
```

```
1               5                  10                 15
Val Gln His Leu Gln Ala Ala Phe Ser Gln Tyr
            20                 25
```

(2) INFORMATION FOR SEQ ID NO:25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: SAL I ADAPTOR (xi) SEQUENCE DESCRIPTION: SEQ ID NO:25:

TCGACTGGAA CGAGACGACC TGCT        24

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: SAL I ADAPTOR (xi) SEQUENCE DESCRIPTION: SEQ ID NO:26:

AGCAGGTCGT CTCGTTCCAG        20

CD40 LIGAND POLYPEPTIDE

CROSS REFERENCE TO RELATED APPLICATION

This application is a divisional application of U.S. Ser. No. 08/484,624, filed Jun. 7, 1995, which is a continuation-in-part application of U.S. patent application Ser. No. 08/249,189, filed May 24, 1994, which is a continuation-in-part of U.S. patent application Ser. No. 07/969,703, filed Oct. 23, 1992, now abandoned, which is a continuation-in-part of U.S. patent application Ser. No. 07/805,723, filed on Dec. 5, 1991, now abandoned, which is a continuation-in-part of U.S. patent application Ser. No. 07/783,707, filed on Oct. 25, 1991, now abandoned.

TECHNICAL FIELD OF THE INVENTION

The present invention relates to a novel cytokine. More specifically, the present invention relates to the cloning of a murine and a human cytokine that binds to a human CD40 having both agonist and antagonist activity in soluble and membrane-bound forms.

BACKGROUND OF THE INVENTION

Cytokines that have an "Interleukin" designation are those protein factors that influence immune effector cells. Cytokines designated interleukin-1 through interleukin-12 have been reported and named as an interleukin. Other known cytokines include tumor necrosis factor (TNF), granulocyte-macrophage colony stimulating factor (GM-CSF), granulocyte colony stimulating factor (G-CSF), mast cell growth factor (MGF), epidermal growth factor (EGF), platelet-derived growth factor (PDGF), nerve growth factor (NGF), erythropoietin (EPO), γ-interferon (γ-IFN) and others.

DNAs for two different TNF receptors (Type I and Type II) have been cloned (Smith et al., *Science* 248:1019, 1990; and Schall et al., *Cell* 61:361, 1990). Both forms of TNF receptor are related to each other and belong to a family of receptors whose members include nerve growth factor receptor (Johnson et al., *Cell* 47:545, 1986), B cell antigen CD40 (Stamenkovic et al., *EMBO J.* 8:1403, 1989), T cell antigen OX40 (Mallett et al., *EMBO J.* 9:1063, 1990), human Fas antigen (Itoh et al., *Cell* 66:233, 1991) and murine 4-1BB receptor (Kwon et al., *Cell. Immunol.* 121:414, 1989 [Kwon et al. I] and Kwon et al., *Proc. Natl. Acad. Sci. USA* 86:1963, 1989 [Kwon et al. II]).

Human CD40 protein (CD40) is a peptide of 277 amino acids having a molecular weight of 30,600, and a 19 amino acid secretory signal peptide comprising predominantly hydrophobic amino acids (Stamenkovic et al.). The molecular weight (exclusive of glycosylation) of the mature human CD40 protein is 28,300. A cDNA encoding human CD40 was isolated from a cDNA library prepared from Burkitt lymphoma cell line Raji. The putative protein encoded by the CD40 cDNA contains a putative leader sequence, transmembrane domain and a number of other features common to membrane-bound receptor proteins. CD40 has been found to be expressed on B lymphocytes, epithelial cells and some carcinoma cell lines.

A monoclonal antibody (mAb) directed against CD40 has been shown to mediate various functional effects of human B cells. These effects include: (a) homotypic adhesions (Gordon et al., *J. Immunol.* 140:1425, 1988 [Gordon et al. I]); (b) increased cell size (Gordon et al. I and Valle et al., *Eur. J. Immunol.* 19:1463, 1989); (c) proliferation of B cells activated with anti-IgM, anti-CD20 mAb, phorbol ester alone (Clark et al., *Proc. Natl. Acad. Sci. USA* 83:4494, 1986; and Paulie et al., *J. Immunol.* 142:590, 1989), or phorbol ester combined with interleukin-4 (Gordon et al., *Eur. J. Immunol.* 17:1535, 1987 [Gordon et al. II]; and (d) production of IgE (Jabara et al., *J. Exp. Med.* 172:1861, 1990; Zhang et al., *J. Immunol.* 146:1836, 1991) and IgM (Gascan et al., *J. Immunol.* 147:8, 1991) from interleukin-4 (IL-4) stimulated T-depleted cultures.

One such antibody, called mAb 89 by Banchereau et al., *Clin. Immunol. Spectrum* 3:8, 1991 [Banchereau et al. I], was found to induce human B cell proliferation at a relatively low antibody concentration (30 ng/ml or about $10^{-10}$ M). Proliferation lasted two to three weeks and resulted in a ten-fold expansion of the human B cell population. Optimal stimulation of the B cells occurred when CD40 surface molecule was cross-linked by IgM. Fab fragments of another anti-CD40 mAb induced only a weak proliferative response. Further, Banchereau et al., *Science* 251:70, 1991 [Banchereau et al. II] reported that resting human B cells entered a state of sustained proliferation when incubated with both a murine fibroblastic Ltk⁻ cell line that was transfected with human Fc receptor and with a monoclonal antibody specific for human CD40. Banchereau et al. II found that cross-linking CD40 is necessary for clonal expansion of B cells.

CD23 is a low affinity IgE receptor that has been found to be expressed on most IgM⁻/IgD⁻ mature B cells, but not T cells. CD23 has been sequenced and its sequence was described in Kikutani et al., *Cell* 47:657, 1986. Soluble CD23 (sCD23) was found to induce a pyrogenic reaction in rabbits and this reaction was abrogated by administration of human IgE (Ghaderi et al., *Immunology* 73:510, 1991). Therefore, CD23 may be an appropriate marker for soluble CD40 or CD40-L effects.

Prior to the present invention, a ligand for CD40 was unknown. Accordingly, there is a need in the art to identify and characterize a CD40 ligand (CD40-L).

SUMMARY OF THE INVENTION

A novel cytokine, hereafter referred to as "CD40-L," has been isolated and characterized. The nucleotide sequence and deduced amino acid sequence of representative murine CD40-L cDNA is disclosed in SEQ ID NO:1 and FIGS. 1A and 1B, and the amino acid sequence is also listed in SEQ ID NO:2. The nucleotide sequence and deduced amino acid sequence of representative human CD40-L cDNA is disclosed in SEQ ID NO:11 and FIGS. 2A and 2B, and the amino acid sequence is also listed in SEQ ID NO:12. The present invention further comprises other CD40-L polypeptides encoded by nucleotide sequences that hybridize, under moderate or severe stringency conditions, to probes defined by SEQ ID NO:11 (the coding region of human CD40-L), fragments of the sequence extending from nucleotide 46 to nucleotide 828 of SEQ ID NO:11, or to DNA or RNA sequences complementary to FIGS. 2A and 2B (SEQ ID NO:11) or fragments thereof. The invention further comprises nucleic acid sequences which, due to the degeneracy of the genetic code, encode polypeptides substantially identical or substantially similar to polypeptides encoded by the nucleic acid sequences described above, and sequences complementary to them.

CD40-L is a type II membrane polypeptide having an extracellular region at its C-terminus, a transmembrane region and an intracellular region at its N-terminus. A soluble version of murine CD40-L has been found in supernatants from EL-4 cells and EL-4 cells sorted on the basis of a biotinylated CD40/Fc fusion protein described herein. Soluble CD40-L comprises an extracellular region of CD40-L or a fragment thereof. The protein sequence of murine CD40-L is described in FIGS. 1A and 1B and SEQ ID NO:2, and human CD40-L in FIGS. 2A and 2B and SEQ ID NO:12. The extracellular region of murine CD40-L extends from amino acid 47 to amino acid 260 in FIGS. 1A and 1B and SEQ ID NO:2, and of human CD40-L from amino acid 47 to amino acid 261 in FIGS. 2A and 2B and SEQ ID NO:12. CD40-L biological activity is mediated by binding of this cytokine with CD40 and includes B cell proliferation and induction of antibody secretion, including IgE secretion.

The present invention further provides antisense or sense oligonucleotides (deoxyribonucleotides or ribonucleotides) that correspond to a sequence of at least about 12 nucleotides selected from the nucleotide sequence of CD40-L or DNA or RNA sequences complementary to the nucleotide sequence of CD40-L as described in SEQ ID NO:1 and SEQ ID NO:11 and in FIGS. 1A, 1B, 2A, and 2B. Such antisense or sense oligonucleotides prevent transcription or translation of CD40-L mRNA or polypeptides.

Further still, the present invention provides CD40-L peptide fragments that correspond to a protein sequence of at least 10 amino acids selected from the amino acid sequence encoded by SEQ ID NO:1 or SEQ ID NO:11 that can act as immunogens to generate antibodies specific to the CD40-L immunogens. Such CD40-L immunogen fragments can serve as antigenic determinants in providing monoclonal antibodies specific for CD40-L.

The invention also provides a human CD40/Fc fusion protein and a soluble CD40 protein (sCD40) comprising the extracellular region of human CD40. Both sCD40 and CD40/Fc fusion protein can inhibit CD40-L or anti-CD40 mAb induced B cell stimulation, IL-4-induced IgE stimulation and IL-4 induced CD23 induction in B cells.

BRIEF DESCRIPTION OF THE DRAWINGS

FIGS. 1A and 1B illustrate nucleotide and amino acid sequences corresponding to murine CD40-L (SEQ ID NOS:1 and 2). This protein is a type II polypeptide having its N-terminus as its intracellular domain, followed by a transmembrane region, and an extracellular domain at the C-terminus of the polypeptide. The extracellular domain, which is longer than either the intracellular domain or the transmembrane region, contains one potential N-linked glycosylation site and two potential disulfide bonds in view of four cysteine (Cys) residues.

FIGS. 2A and 2B illustrate nucleotide and amino acid sequences corresponding to human CD40-L (SEQ ID NOS:11 and 12). This protein is a type II polypeptide having its N-terminus as its intracellular domain, followed by a transmembrane region, and an extracellular domain at the C-terminus of the polypeptide. The extracellular domain, which is longer than either the intracellular domain or the transmembrane region, contains 1 potential N-linked glycosylation site and 2 potential disulfide bonds in view of 5 cysteine (Cys) residues.

FIG. 3 illustrates a comparison of protein sequences of human and murine CD40-L showing 77.7% homology at the amino acid level.

FIGS. 15A–15D show representative FACS profiles of peripheral blood T cells stimulated for 16 hours with 10 ng/ml PMA and 500 ng/ml ionomycin, and stained with 5 μg/ml CD40/Fc, a control Fc protein, IL-4 receptor/Fc, murine IgG$_1$, and a CD40-L monoclonal antibody referred to as M90.

DETAILED DESCRIPTION OF THE INVENTION

Figure 4A:
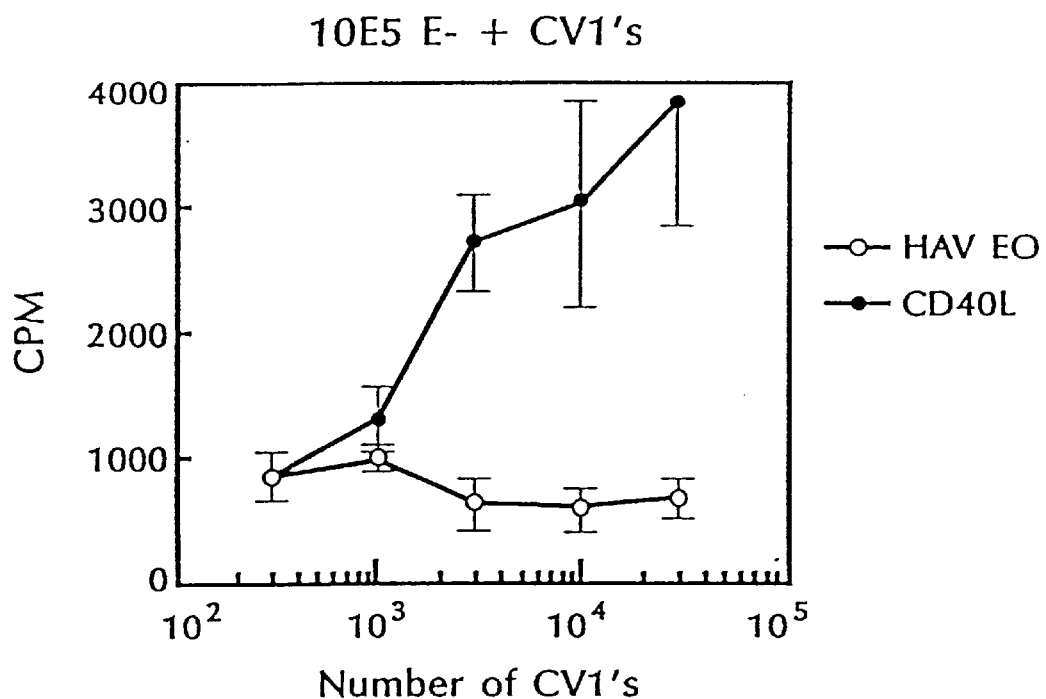
FIGS. 4A–4B illustrate proliferation of T cell depleted human peripheral blood mononuclear cells (PBMC) caused by incubation with CV1 cells transfected with full length murine CD40-L cDNA (SEQ ID NO:1) and expressing bound CD40-L (CD40-L$^+$CV1 cells) when compared with CV1 cells transfected with empty vector (HAVEO) and not expressing bound murine CD40-L. The day 7 proliferation results show that CD40-L$^+$CV1 cells significantly increase proliferation of T-cell depleted PBMC in the presence or absence of interleukin-4 (IL-4).

Novel polypeptides that can act as a ligand for murine and human CD40 have been isolated and sequenced. More particularly, cDNAs encoding these ligands have been cloned and sequenced. Further provided are methods for expression of recombinant CD40-L polypeptides. CD40-L polypeptide include other forms of mammalian CD40-L, such as derivatives or analogs of human or murine CD40-L. Murine and human CD40-L comprise a 214 and 215, respectively amino acid extracellular region at the C-terminus of full length, membrane-bound polypeptide. The extracellular region contains the domain that binds to CD40. Murine and human CD40-L further comprise a homologous hydrophobic 24 amino acid transmembrane region delineated by charged amino acids on either side and a 22 amino acid intracellular region at their N-termini. The present invention further comprises full length CD40-L polypeptides or fragments thereof comprising all or part of the extracellular region or derivatives of the extracellular region and mammalian cells transfected with a cDNA encoding murine or human CD40-L and expressing human or murine CD40-L as a membrane-bound protein.

The present invention comprises isolated DNA sequences encoding CD40-L polypeptides and DNA or RNA sequences complementary to such isolated DNA sequences. The isolated DNA sequences and their complements are selected from the group consisting of (a) nucleotides 184 through 828, 193 through 828, 193 through 762, or 403 through 762 of the DNA sequence set forth in FIGS. 2A and 2B (SEQ ID NO:11) and their complements, (b) DNA sequences which hybridize to the DNA sequences of (a) or their complements under conditions of moderate stringency and which encode a CD40-L polypeptide, analogs or derivatives thereof, and (c) DNA sequences which, due to the degeneracy of the genetic code, encode CD40-L polypeptides encoded by any of the foregoing DNA sequences and their complements. In addition, the present invention includes vectors comprising DNA sequences encoding CD40-L polypeptides and analogs, and host cells transfected with such vectors.

The novel cytokine disclosed herein is a ligand for CD40, a receptor that is a member of the TNF receptor super family. Therefore, CD40-L is likely to be responsible for transducing signal via CD40, which is known to be expressed, for example, by B lymphocytes. Full-length CD40-L is a membrane-bound polypeptide with an extracellular region at its C terminus, a transmembrane region, and an intracellular region at its N-terminus. A soluble version of CD40-L can be made from the extracellular region or a fragment thereof and a soluble CD40-L has been found in culture supernatants from cells that express a membrane-bound version of CD40-L. The protein sequence of the extracellular region of murine CD40-L extends from amino acid 47 to amino acid 260 in FIGS. 1A and 1B and SEQ ID NO:2. The protein sequence of the extracellular region of human CD40-L extends from amino acid 47 to amino acid 261 in FIGS. 2A and 2B and SEQ ID NO:12. The biological activity of CD40-L is mediated by binding to CD40 or a species-specific homolog thereof and comprises proliferation of B cells and induction of immunoglobulin secretion from activated B cells. CD40-L (including soluble monomeric and oligomeric forms, as well as membrane-bound forms) can effect B cell proliferation and immunoglobulin secretion (except IgE secretion) without the presence of added IL-4, in contrast to anti-CD40 antibodies, which require IL-4 and cross-linking to mediate activity.

CD40-L refers to a genus of polypeptides which are capable of binding CD40, or mammalian homologs of CD40. As used herein, the term "CD40-L" includes soluble CD40-L polypeptides lacking transmembrane and intracellular regions, mammalian homologs of human CD40-L, analogs of human or murine CD40-L or derivatives of human or murine CD40-L.

CD40-L may also be obtained by mutations of nucleotide sequences coding for a CD40-L polypeptide. A CD40-L analog, as referred to herein, is a polypeptide substantially homologous to a sequence of human or murine CD40-L but which has an amino acid sequence different from native sequence CD40-L (human or murine species) polypeptide because of one or a plurality of deletions, insertions or substitutions. Analogs of CD40-L can be synthesized from DNA constructs prepared by oligonucleotide synthesis and ligation or by site-specific mutagenesis techniques.

Generally, substitutions should be made conservatively; i.e., the most preferred substitute amino acids are those which do not affect the ability of the inventive proteins to bind their receptors in a manner substantially equivalent to that of native CD40-L. Examples of conservative substitutions include substitution of amino acids outside of the binding domain(s), and substitution of amino acids that do not alter the secondary and/or tertiary structure of CD40-L. Additional examples include substituting one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known.

Similarly, when a deletion or insertion strategy is adopted, the potential effect of the deletion or insertion on biological activity should be considered. Subunits of viral proteins may be constructed by deleting terminal or internal residues or sequences to form fragments. Additional guidance as to the types of mutations that can be made is provided by a comparison of the sequence of CD40-L to the sequences and structures of other TNF family members.

The primary amino acid structure of human or murine CD40-L may be modified to create CD40-L derivatives by forming covalent or aggregative conjugates with other chemical moieties, such as glycosyl groups, lipids, phosphate, acetyl groups and the like, or by creating amino acid sequence mutants. Covalent derivatives of CD40-L are prepared by linking particular functional groups to CD40-L amino acid side chains or at the N-terminus or C-terminus of a CD40-L polypeptide or the extracellular domain thereof. Other derivatives of CD40-L within the scope of this invention include covalent or aggregative conjugates of CD40-L or its fragments with other proteins or polypeptides, such as by synthesis in recombinant culture as N-terminal or C-terminal fusions. For example, the conjugate may comprise a signal or leader polypeptide sequence at the N-terminal region or C-terminal region of a CD40-L polypeptide which co-translationally or post-translationally directs transfer of the conjugate from its site of synthesis to a site inside or outside of the cell membrane or cell wall (e.g. the α-factor leader of Saccharomyces).

CD40-L polypeptide fusions can comprise polypeptides added to facilitate purification and identification of CD40-L (e.g. poly-His), or fusions with other cytokines to provide novel polyfunctional entities. Other cytokines include, for example, any of interleukins-1 through 13, TNF (tumor necrosis factor), GM-CSF (granulocyte macrophage-colony stimulating factor), G-CSF (granulocyte-colony stimulating factor), MGF (mast cell growth factor), EGF (epidermal growth factor), PDGF (platelet-derived growth factor), NGF (nerve growth factor), EPO (erythropoietin), γ-IFN (gamma interferon), 4-1BB-L (4-1BB ligand) and other cytokines that affect immune cell growth, differentiation or function.

Nucleic acid sequences within the scope of the present invention include DNA and/or RNA sequences that hybridize to the nucleotide sequence of SEQ ID NO:1 or SEQ ID NO:11 or the complementary strands, under conditions of moderate or severe stringency. Moderate stringency hybridization conditions refer to conditions described in, for example, Sambrook et al. *Molecular Cloning: A Laboratory Manual*, 2 ed. Vol. 1, pp. 1.101–104, Cold Spring Harbor Laboratory Press, (1989). Conditions of moderate stringency, as defined by Sambrook et al., include use of a prewashing solution of 5×SSC, 0.5% SDS, 1.0 mM EDTA (pH 8.0) and hybridization conditions of 50° C., 5×SSC, overnight. Conditions of severe stringency include higher temperatures of hybridization and washing (for example, hybridization in 6×SSC at 63° C. overnight; washing in 3×SSC at 55° C.).

Biological activity of CD40-L may be determined, for example, by competition for binding to the ligand binding domain of CD40 (i.e. competitive binding assays). Both murine CD40-L and human CD40-L bind to human CD40. The binding affinity of murine CD40-L (expressed on sorted murine EL-40.9 cells) for human CD40 was approximately $1.74 \times 10^9$ $M^{-1}$. Similarly, the binding affinity of murine CD40-L (expressed on unsorted murine EL-46.1 cells) for human CD40 was approximately $2.3 \times 10^9$ $M^{-1}$. Both binding affinity measurements are within a range typical of cytokine/cytokine receptor binding.

One configuration of a competitive binding assay for CD40-L polypeptide uses a radiolabeled, soluble murine CD40-L according to FIGS. 1A and 1B (SEQ ID NO:1) or human CD40-L according to FIGS. 2A and 2B (SEQ ID NO:11), and intact cells expressing CD40 (e.g., human B cells). Instead of intact cells, one could substitute soluble CD40 (such as a CD40/Fc fusion protein) bound to a solid phase through a Protein A or Protein G interaction with the Fc region of the fusion protein. A second configuration of a competitive binding assay utilizes radiolabeled soluble CD40 such as a CD40/Fc fusion protein, and intact cells expressing CD40-L. Alternatively, soluble CD40-L could be bound to a solid phase.

Competitive binding assays can be performed using standard methodology. For example, radiolabeled murine CD40-L can be used to compete with a putative CD40-L homolog to assay for binding activity against surface-bound CD40. Qualitative results can be obtained by competitive autoradiographic plate binding assays, or Scatchard plots may be utilized to generate quantitative results.

Competitive binding assays with intact cells expressing CD40 can be performed by two methods. In a first method, B cells are grown either in suspension or by adherence to tissue culture plates. Adherent cells can be removed by treatment with 5 mM EDTA treatment for ten minutes at 37° C. In a second method, transfected COS cells expressing membrane-bound CD40 can be used. COS cells or another mammalian cell can be transfected with human CD40 cDNA in an appropriate vector to express full length CD40 with an extracellular region exterior to the cell.

Alternatively, soluble CD40 can be bound to a solid phase such as a column chromatography matrix, or a tube or similar substrate suitable for analysis for the presence of a detectable moiety such as $^{125}I$. Binding to a solid phase can be accomplished, for example, by obtaining a CD40/Fc fusion protein and binding it to a protein A or protein G surface.

Another means to measure the biological activity of CD40-L and homologs thereof is to utilize conjugated, soluble CD40 (for example, $^{125}I$-CD40/Fc) in competition assays similar to those described above. In this case, however, intact cells expressing CD40-L, or soluble CD40-L bound to a solid substrate, are used to measure competition for binding of conjugated, soluble CD40 to CD40-L by a sample containing a putative CD40 homolog.

CD40-L may also be assayed by measuring biological activity in a B cell proliferation assay. Human B cells may be obtained from human tonsils by purification by negative selection and Percoll density sedimentation, as described by Defrance et al., *J. Immunol.* 139:1135, 1987. Burkitt lymphoma cell lines may be used to measure cell proliferation in response to CD40-L. Examples of Burkitt lymphoma cell lines include, for example, Raji (ATCC CCL 86), Daudi (ATCC CCL 213) and Namalwa (ATCC CRL 1432). Membrane-bound CD40-L stimulated B cell proliferation. Oligomeric, preferably dimeric, CD40-L can stimulate B cell proliferation. CD40 (receptor) antagonizes CD40-L proliferation of B cells.

Yet another assay for determining CD40-L biological activity is to measure immunoglobulin produced by B cells in response to activation by CD40-L or a derivative or analog thereof. Polyclonal immunoglobulin secretion can be measured, for example, by incubating with $5 \times 10^5$ B cells/ml in culture for at least seven days. Immunoglobulin (Ig) production can be measured by an ELISA assay such as one described in Maliszewski et al., *J. Immunol.* 144:3028, 1990 [Maliszewski et al. I] or Maliszewski et al., *Eur J. Immunol.* 20:1735, 1990 [Maliszewski et al. II]. Murine B cells can be obtained, for example, from mice and cultured according to procedures described in Grabstein et al., *J. Exp. Med.* 163:1405, 1986 [Grabstein et al. I], Maliszewski et al. I, and Maliszewski et al. II.

CD40-L can be used in a binding assay to detect cells expressing CD40. For example, murine CD40-L according to FIGS. 1A and 1B (SEQ ID NO:1) or human CD40-L according to FIGS. 2A and 2B (SEQ ID NO:11), or an extracellular domain or a fragment thereof, can be conjugated to a detectable moiety such as $^{125}I$. Radiolabeling with $^{125}I$ can be performed by any of several standard methodologies that yield a functional $^{125}I$-CD40-L molecule labeled to high specific activity. Alternatively, another detectable moiety such as an enzyme that can catalyze a colorimetric or fluorometric reaction, biotin or avidin may be used. Cells expressing CD40 can be contacted with conjugated CD40-L. After incubation, unbound conjugated CD40-L is removed and binding is measured using the detectable moiety.

CD40-L polypeptides may exist as oligomers, such as dimers or trimers. Oligomers are linked by disulfide bonds formed between cysteine residues on different CD40-L polypeptides. Alternatively, one can link two soluble CD40-L domains with a $Gly_4SerGly_5Ser$ linker sequence, or other linker sequence described in U.S. Pat. No. 5,073,627, which is incorporated by reference herein. CD40-L polypeptides may also be created by fusion of the C terminal of soluble CD40-L (extracellular domain) to the Fc region of IgG1 (for example, SEQ ID NO:3) as described for the CD40/Fc fusion protein. CD40-L/Fc fusion proteins are allowed to assemble much like heavy chains of an antibody molecule to form divalent CD40-L. If fusion proteins are made with both heavy and light chains of an antibody, it is possible to form a CD40-L oligomer with as many as four CD40-L extracellular regions.

Fusion proteins can be prepared using conventional techniques of enzyme cutting and ligation of fragments from desired sequences. PCR techniques employing synthetic oligonucleotides may be used to prepare and/or amplify the desired fragments. Overlapping synthetic oligonucleotides representing the desired sequences can also be used to prepare DNA constructs encoding fusion proteins. Fusion proteins can also comprise CD40-L and two or more additional sequences, including a leader (or signal peptide) sequence, Fc region, linker sequence, and sequences encoding highly antigenic moieties that provide a means for facile purification or rapid detection of a fusion protein.

Signal peptides facilitate secretion of proteins from cells. An exemplary signal peptide is the amino terminal 25 amino acids of the leader sequence of human interleukin-7 (IL-7; Goodwin et al., *Proc. Natl. Acad. Sci. U.S.A.* 86:302, 1989; FIG. 2B). Other signal peptides may also be employed. For example, certain nucleotides in the IL-7 leader sequence can be altered without altering the amino acid sequence. Additionally, amino acid changes that do not affect the ability of the IL-7 sequence to act as a leader sequence can be made.

The FLAG™ octapeptide (amino acid 1–8 of SEQ ID NO:16) does not alter the biological activity of fusion proteins, is highly antigenic and provides an epitope reversibly bound by a specific monoclonal antibody, enabling rapid detection and facile purification of the expressed fusion protein. The FLAG™ sequence is also specifically cleaved by bovine mucosal enterokinase at the residue immediately following the Asp-Lys pairing, fusion proteins capped with this peptide may also be resistant to intracellular degradation in *E. coli*. A murine monoclonal antibody that binds the FLAG™ sequence has been deposited with the ATCC under accession number HB 9259; methods of using the antibody in purification of fusion proteins comprising the FLAG™ sequence are described in U.S. Pat. No. 5,011,912, which is incorporated by reference herein.

Suitable Fc regions are defined as Fc regions that can bind to protein A or protein G, or alternatively, are recognized by an antibody that can be used in purification or detection of a fusion protein comprising the Fc region. Preferable Fc regions include the Fc region of human $IgG_1$ or murine $IgG_1$. One example is the human $IgG_1$ Fc region shown in SEQ ID NO:3; another example is an Fc region encoded by cDNA obtained by PCR from oligonucleotide primers from SEQ ID NO:9 and SEQ ID NO:10 with human cDNA as a template. Portions of a suitable Fc region may also be used, for example, an Fc region of human $IgG_1$ from which has been deleted a sequence of amino acids responsible for binding to protein A, such that the resultant Fc region binds to protein G but not protein A.

The $[Gly_4Ser]_3$ repeat sequence provides a linker sequence that separates the extracellular region of the CD40-L from the Fc portion of the fusion protein by a distance sufficient to ensure that the CD40-L properly folds into its secondary and tertiary structures. Suitable linker sequences (1) will adopt a flexible extended conformation, (2) will not exhibit a propensity for developing an ordered secondary structure which could interact with the functional domains of fusion proteins, and (3) will have minimal hydrophobic or charged character which could promote interaction with the functional protein domains. Typical surface amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, may also be used in the linker sequence. The length of the linker sequence may vary without significantly affecting the biological activity of the fusion protein. Linker sequences are unnecessary where the proteins being fused have non-essential N- or C-terminal amino acid regions which can be used to separate the functional domains and prevent steric interference.

CD40-L polypeptides may exist as soluble polypeptides comprising the extracellular domain of CD40-L as shown in FIGS. 1A and 1B (SEQ ID NO:1) and FIGS. 2A and 2B (SEQ ID NO:11) or as membrane-bound polypeptides comprising the extracellular domain, a transmembrane region and a short intracellular domain, as shown in FIGS. 1A and 1B (SEQ ID NO:1) and FIGS. 2A and 2B (SEQ ID NO:11) for the murine and human sequences, respectively. Moreover, the present invention comprises oligomers of CD40-L extracellular domains or fragments thereof, linked by disulfide interactions, or expressed as fusion polymers with or without spacer amino acid linking groups. For example, a dimer CD40-L molecule can be linked by an IgG Fc region linking group.

Without being bound by theory, membrane-bound CD40-L and oligomeric CD40-L can achieve activity stimulating Ig formation and proliferation of B cells previously only achieved by cross-linked anti-CD40 antibody in the presence of IL-4. It further appears likely that monomeric soluble CD40-L, comprising only the extracellular domain of CD40-L and capable of binding to CD40 receptor, will serve to antagonize the activity of membrane-bound and oligomeric CD40-L and/or cross-linked anti-CD40 antibodies. It further appears likely that the interaction of membrane-bound CD40-L with CD40 is the principal molecular interaction responsible for T cell contact dependent induction of B cell growth and differentiation to both antigen specific antibody production and polyclonal Ig secretion. In this regard, a mammalian cell transfected with a cDNA encoding full length CD40-L (i.e., being membrane-bound and having an intracellular domain, a transmembrane region and an extracellular domain or a fragment thereof) can mimic T cells in their ability to induce B cell growth, differentiation and stimulation of antigen-specific antibody production. It appears that activities of oligomeric soluble CD40-L, preferably an oligomer of extracellular regions, can mimic the biological activities of membrane-bound CD40-L. Moreover, soluble monomeric CD40-L (comprising the extracellular domain or a fragment thereof) can bind to CD40 receptor to prevent T cell interaction with B cells and therefor have activity similar to CD40 (receptor) extracellular domain which itself may be in monomeric or in oligomeric form. Alternatively, CD40-L can be oligomeric to act as a soluble factor capable of inducing B cell growth, differentiation and stimulation of antigen-specific antibody production. Accordingly, it appears that membrane-bound CD40-L and oligomeric CD40-L act as CD40 agonists, while soluble (monomeric) CD40-L and soluble CD40 act as CD40 antagonists by blocking CD40 receptor sites without significantly transducing signal or by preventing CD40-L binding to CD40 sites on B cells and other target cells.

Both CD40 agonists and CD40 antagonists will have useful therapeutic activity. For example, CD40 agonists (i.e., membrane-bound CD40-L and oligomeric CD40-L) are useful as vaccine adjuvants and for stimulating mAb production from hybridoma cells. CD40 antagonists (i.e., CD40 receptor, CD40/Fc and possibly soluble, monomeric CD40-L) are useful for treating autoimmune diseases characterized by presence of high levels of antigen-antibody complexes, such as allergy, systemic lupus erythematosis, rheumatoid arthritis, insulin dependent diabetes mellitus (IDDM), graft versus host disease (GVHD) and others.

IgE secretion from human B cells can be induced by IL-4 in the presence of T cells (Vercelli et al., *J. Exp. Med.* 169:1295, 1989). Further, IgE production can be induced from T cell depleted PBM (peripheral blood mononuclear cells) by addition of an anti-CD40 mAb (Jabara et al., *J. Exp. Med.* 172:1861, 1990 and Zhang et al., J. Immunol. 146:1836, 1991). The present invention further includes a method for inhibiting IgE production from activated B cells, activated by IL-4 in the presence of T cells or by CD40-L (preferably, membrane-bound CD40-L), comprising administering an effective amount of a CD40/Fc fusion protein, as described herein, or a soluble CD40 encoded by the cDNA sequence described in SEQ ID NO. 3. Similarly, CD40 receptors and possibly soluble CD40-L (monomer only) can also block secretion of other antibody isotypes.

The present invention further includes CD40-L polypeptides with or without associated native-pattern glycosylation. CD40-L expressed in yeast or mammalian expression systems (e.g., COS-7 cells) may be similar to or significantly different from a native CD40-L polypeptide in molecular weight and glycosylation pattern, depending upon the choice of expression system. Expression of CD40-L polypeptides in bacterial expression systems, such as *E. coli*, provides non-glycosylated molecules.

DNA constructs that encode various additions or substitutions of amino acid residues or sequences, or deletions of terminal or internal residues or sequences not needed for biological activity or binding can be prepared. For example, the extracellular CD40-L N-glycosylation site can be modified to preclude glycosylation while allowing expression of a homogeneous, reduced carbohydrate analog using yeast expression systems. N-glycosylation sites in eukaryotic polypeptides are characterized by an amino acid triplet Asn-X-Y, wherein X is any amino acid except Pro and Y is Ser or Thr. Appropriate modifications to the nucleotide sequence encoding this triplet will result in substitutions, additions or deletions that prevent attachment of carbohydrate residues at the Asn side chain. In another example, sequences encoding Cys residues can be altered to cause the Cys residues to be deleted or replaced with other amino acids, preventing formation of incorrect intramolecular disulfide bridges upon renaturation. Human CD40-L comprises five Cys residues in its extracellular domain. Thus, at least one of the five Cys residues can be replaced with another amino acid or deleted without effecting protein tertiary structure or disulfide bond formation.

Other approaches to mutagenesis involve modification of sequences encoding dibasic amino acid residues to enhance expression in yeast systems in which KEX2 protease activity is present. Sub-units of a CD40-L polypeptide may be constructed by deleting sequences encoding terminal or internal residues or sequences. Moreover, other analyses may be performed to assist the skilled artisan in selecting sites for mutagenesis. For example, PCT/US92/03743 (the disclosure of which is hereby incorporated by reference) discusses methods of selecting ligand agonists and antagonists.

CD40-L polypeptides are encoded by multi-exon genes. The present invention further includes alternative mRNA constructs which can be attributed to different mRNA splicing events following transcription and which share regions of identity or similarity with the cDNAs disclosed herein.

Antisense or sense oligonucleotides comprise a single-stranded nucleic acid sequence (either RNA or DNA) capable of binding to target CD40-L mRNA (sense) or CD40-L DNA (antisense) sequences. Antisense or sense oligonucleotides, according to the present invention, comprise a fragment of SEQ ID NO:1 or SEQ ID NO:11, or a DNA or RNA complement of SEQ ID NO:1 or SEQ ID NO:11. Such a fragment comprises at least about 14 nucleotides. Preferably, such a fragment comprises from about 14 to about 30 nucleotides. The ability to create an antisense or a sense oligonucleotide, based upon a cDNA sequence for CD40-L is described in, for example, Stein and Cohen, *Cancer Res.* 48:2659, 1988 and van der Krol et al., *Bio-Techniques* 6:958, 1988.

Binding of antisense or sense oligonucleotides to target nucleic acid sequences results in the formation of duplexes that block translation (RNA) or transcription (DNA) by one of several means, including enhanced degradation of the duplexes, premature termination of transcription or translation, or by other means. Suitable polymerase promotors include promotors for any RNA polymerase, or promotors for any DNA polymerase. Antisense or sense oligonucleotides further comprise oligonucleotides having modified sugar-phosphodiester backbones (or other sugar linkages, such as those described in WO091/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence. Antisense or sense oligonucleotides may be introduced into a cell containing the target nucleic acid sequence by any gene transfer method, including, for example, $CaPO_4$-mediated DNA transfection, electroporation, or other gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, the murine retrovirus M-MuLV, N2 (a retrovirus derived from M-MuLV), or or the double copy vectors designated DCT5A, DCT5B and DCT5C (see PCT Application US 90/02656). Alternatively, other promotor sequences may be used to express the oligonucleotide.

Sense or antisense oligonucleotides may also be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The sequence of murine CD40-L cDNA was obtained by direct expression techniques. The sequence of human CD40-L was obtained by cross-species hybridization techniques using the murine CD40-L cDNA as a probe.

We cloned murine CD40-L by first obtaining a clone of the extracellular region of human CD40 (the receptor) by polymerase chain reaction (PCR) techniques using primers based upon a sequence published in Stamenkovic et al. (SEQ ID NO:4). An upstream oligonucleotide primer 5'-CCGTCGACCACCATGGTTCGTCTGCC -3' (SEQ ID NO:5) introduces a Sal 1 site upstream from an initiator methionine of CD40 and a downstream oligonucleotide primer 5'-CCGTCGACGTCTAGAGCCGATCCTGGGG-3' (SEQ ID NO:6) inserts a termination codon after amino acid 192 of CD40, followed by Xba 1 and Sal 1 sites. The amplified cDNA was digested with Sal 1 and cloned into pDC406 (McMahan et al., *EMBO J.* 10:2821, 1991) to construct pDC406/s CD40.

A second CD40 receptor fragment (SEQ ID NO:4) was obtained by PCR techniques for fusion to the Fc domain of human IgG1 (SEQ ID NO:3). Briefly, The upstream oligonucleotide primer (SEQ ID NO:5) and fusion template (SEQ ID NO:4) were the same as before. The downstream oligonucleotide primer was 5'-ACAAGATCTGGGCTCTACGTATCTCAGCCGATCCT GGGGAC-3' (SEQ ID NO:7) that inserts amino acids Tyr Val Glu Pro Arg (SEQ ID NO:8) after amino acid 193 of CD40. Glu and Pro are the first two amino acids of a hinge region of human IgG1, and are followed by a Bgl II restriction site. The Bgl II restriction site was used to fuse the extracellular domain of CD40 to the remainder of human IgG1 Fc region.

Other fusion proteins comprising ligand binding domains from other receptors can be made by obtaining a DNA sequence for the ligand binding domain of a receptor and fusing this sequence to a DNA sequence encoding an Fc region of an antibody molecule that binds to protein A or protein G, or another polypeptide that is capable of affinity purification, for example, avidin or streptavidin. The resultant gene construct can be introduced into mammalian cells to transiently express a fusion protein. Receptor/Fc fusion proteins can be purified by protein A or protein G affinity purification. Receptor/avidin fusion proteins can be purified by biotin affinity chromatography. The fusion protein can later be removed from the column by eluting with a high salt solution or another appropriate buffer.

We obtained a cDNA encoding human IgG1 Fc region by PCR amplification using cDNA from human cells as a template and an upstream oligonucleotide primer 5'-TATTAATCATTCAGTAGGGCCCAGATCTTGTGACA AAACTCAC-3' (SEQ ID NO:9) and a downstream oligonucleotide primer 5'-GCCAGCTTAACTAGTTCATTTACCCGGAGACAGG GAGA-3" (SEQ ID NO:10). The PCR amplified cDNA introduced a Bgl II site near the beginning of the hinge region, which was used to ligate CD40 extracellular domain to construct a s CD40/Fc fusion cDNA, which was ligated into pDC406 to construct pDC406/CD40/Fc. Other suitable Fc regions are defined as any region that can bind with high affinity to protein A or protein G, and includes the Fc region of human IgG1 or murine IgG1. One example is the human IgG1 Fc region shown in SEQ ID NO:3 or the cDNA obtained by PCR from oligonucleotide primers from SEQ ID NO:9 and SEQ ID NO:10 with human cDNA as a template.

Receptor/Fc fusion molecules preferably are synthesized in recombinant mammalian cell culture because they are generally too large and complex to be synthesized by prokaryotic expression methods. Examples of suitable mammalian cells for expressing a receptor/Fc fusion protein include CV-1 cells (ATCC CCL 70) and COS-7 cells (ATCC CRL 1651), both derived from monkey kidney.

The DNA construct pDC406/CD40/Fc was transfected into the monkey kidney cell line CV-1/EBNA (ATCC CRL 10478). The pDC406 plasmid includes regulatory sequences derived from SV40, human immunodeficiency virus (HIV), and Epstein-Barr virus (EBV). The CV-1/EBNA cell line was derived by transfection of the CV-1 cell line with a gene encoding Epstein-Barr virus nuclear antigen-1(EBNA-1) and constitutively express EBNA-1 driven from human CMV immediate-early enhancer/promoter. An EBNA-1 gene allows for episomal replication of expression vectors, such as pDC406, that contain the EBV origin of replication.

Transfectants expressing CD40/Fc fusion protein are initially identified using dot blots or Western blots. The supernatants are then subjected to dot blot or gel electrophoresis followed by transfer of the electrophoresed proteins for binding to G28-5 mAb (an antibody that binds to human CD40 receptor). The blotted proteins were then incubated with radiolabeled with $^{125}$I-protein A, washed to remove unbound label, and examined for expression of Fc. Monoclonal antibody G28-5 was produced according to Clark et al., supra.

Once cells expressing the fusion construct were identified, large scale cultures of transfected cells were grown to accumulate supernatant from cells expressing CD40/Fc. CD40/Fc fusion protein in supernatant fluid was purified by affinity purification. Briefly, one liter of culture supernatant containing CD40/Fc fusion protein was purified by filtering mammalian cell supernatants (e.g., in a 0.45μ filter) and applying filtrate to a protein A/G antibody affinity column (Schleicher and Schuell, Keene, NH) at 4° C. at a flow rate of 80 ml/hr for a 1.5 cm×12.0 cm column. The column was washed with 0.5 M NaCl in PBS until free protein could not be detected in wash buffer. Finally, the column was washed with PBS. Bound fusion protein was eluted from the column with 25 mM citrate buffer, pH 2.8, and brought to pH 7 with 500 mM Hepes buffer, pH 9.1. Silver-stained SDS gels of the eluted CD40/Fc fusion protein showed it to be >98% pure.

Soluble CD40 (sCD40) and CD40/Fc fusion proteins were made as described herein. The supernatants were purified through a G28-5 (anti-CD40 mAb) affinity column to affinity purify sCD40 expressed by the transfected CV-1/EBNA cells. Protein-containing fractions were pooled and aliquots removed for G28-5 binding assays and analysis by SDS-PAGE (sodium dodecyl sulfate polyacrylamide gel electrophoresis) in the presence of 1 mM dithiothreitol as a reducing agent. A single band was seen of molecular weight 28,100 daltons. In the absence of a reducing agent, SDS-PAGE analysis of sCD40 revealed two bands, a major band of molecular weight 56,000 and a minor band of molecular weight 28,000. The banding pattern indicates that the majority of sCD40 exists as a disulfide-linked homodimer in solution. The 28,000 band is free monomer.

CD40 proteins were visualized by silver staining. Sample protein concentrations were determined using a micro-BCA assay (Pierce) with ultrapure bovine serum albumin as standard. Soluble CD40 purity and protein concentration were confirmed by amino acid analysis. Purified soluble CD40 was absorbed to PVDF paper and the paper subjected to automated Edman degradation on an Applied Biosystems model 477A protein sequencer according to manufacturers instructions for N-terninal protein sequencing. This procedure checked the protein sequence of sCD40.

Soluble CD40 and CD40/Fc fusion protein were able to modulate human B cell responses in the absence of anti-CD40 mAb (G28-5). Purified tonsillar B cells were cultured with anti-IgM and human IL-4 and either sCD40 or CD40/Fc fusion protein was added. Neither form of CD40 had an inhibitory effect on B cell proliferation (as measured by tritiated thymidine incorporation). IL-4 receptor, by contrast, inhibited IL-4-induced B cell proliferation in a concentration-dependent manner.

Soluble CD40 and CD40/Fc were tested for their ability to inhibit IL-4 induced IgE secretion in a 2-donor MLC (mixed lymphocyte culture) system. In three experiments, the level of IgE production was reduced as the concentration of CD40 was increased. Soluble CD40, added at a concentration of 10 µg/ml, was able to completely inhibit IgE secretion in this model of allergy. Further, CD40/Fc had similar effects as its soluble counterpart. However, addition of an IL-7 receptor-Fc fusion protein (made by similar procedures with a published IL-7 receptor sequence) did not affect secretion of IgE in this model.

Levels of CD23 were also measured in the same MLC in response to sCD40 or CD40/Fc fusion proteins. Soluble CD40 produced a small, but reproducible decrease in sCD23 level at day 6 compared to cultures stimulated with IL-4 alone, however a stronger inhibitory effect was pronounced at day 12 in the same cultures. Soluble CD23 induction by IL-4-stimulated T-depleted PBM (peripheral blood macrophages) E-cells was similarly affected by addition of sCD40, causing a small decrease in sCD23 levels at day 6 and a more pronounced inhibition at day 12. In each culture system, the results with CD40/Fc fusion protein were substantially the same as with sCD40.

In an effort to isolate a cDNA for a CD40-L, purified CD40/Fc fusion protein was radioiodinated with $^{125}$I using a commercially available solid phase agent (IODO-GEN®, 1,3,4,6-tetrachloro-3α-diphenylglycourol Pierce). In this procedure, 5 µg of IODO-GEN were plated at the bottom of a 10×75 mm glass tube and incubated for twenty minutes at 4° C. with 75 µl of 0.1 M sodium phosphate, pH 7.4 and 20 µl (2 mCi) Na$^{125}$I. The solution was then transferred to a second glass tube containing 5 µg of CD40/Fc in 45 µl PBS (phosphate buffered saline) and this reaction mixture was incubated for twenty minutes at 4° C. The reaction mixture was fractionated by gel filtration on a 2 ml bed volume of SEPHADEX® G-25 (Sigma), and then equilibrated in RPMI 1640 medium containing 2.5% (v/v) bovine serum albumin (BSA), 0.2% (v/v) sodium azide and 20 mM Hepes, pH 7.4 binding medium. The final pool of $^{125}$I CD40/Fc was diluted to a working stock solution of 1×10$^{-7}$ M in binding medium and stored for up to one month at 4° C. without detectable loss of receptor binding activity.

A cDNA library was prepared from a EL4 cell line sorted by FACS (fluorescence activated cell sorting) on the basis of binding of a biotinylated CD40/Fc fusion protein. Cells were sorted five times until there was a significant shift in fluorescence intensity based upon expression of a ligand for CD40 by the sorted EL-4 cells. The five-times sorted cells were called EL-40.5 cells and these cells were cultured for the purposes of creating a cDNA library from EL-40.5 mRNA. Briefly, cDNA was synthesized, inserted into empty pDC406 vector and transformed into E. coli. Transformants were pooled, and the DNA from the pools was isolated and transfected into CV1-EBNA cells to create an expression cloning library.

Transfected CV1-EBNA cells were cultured on slides for three days to permit transient expression of CD40-L. The slides containing the transfected cells were then incubated with radioiodinated CD40/Fc, washed to remove unbound CD40/Fc, and fixed with gluteraldehyde. The fixed slides were dipped in liquid photographic emulsion and exposed in the dark. After developing the slides, they were individually examined with a microscope and cells expressing CD40-L were identified by the presence of autoradiographic silver grains against a light background.

The expression cloning library from EL-40.5 cells was screened and one pool, containing approximately 2000 individual clones, was identified as positive for binding $^{125}$I labeled CD40/Fc fusion protein. This pool was broken down into smaller pools of approximately 200 colonies. The smaller pools were screened as described above. One of the smaller pools was positive for CD40-L.

A single clone was isolated and sequenced by standard techniques, to provide the cDNA sequence and deduced amino acid sequence of murine CD40-L as shown in FIGS. 1A and 1B and SEQ ID NO:1.

The human homolog CD40-L cDNA was found by cross species hybridization techniques. Briefly, a human peripheral blood lymphocyte (PBL) cDNA library was made from peripheral blood lymphocytes treated with OKT3 antibody (ATCC, Rockville Md.) that binds to CD3 (10 ng/ml) and interleukin-2 (IL-2, 10 ng/ml) for six days. The PBL cells were washed and then stimulated for 4 hours with 10 ng/ml PMA (phorbol myristate acetate, Sigma St Louis) and 500 ng/ml ionomycin (Calbiochem). Messenger RNA was isolated from stimulated PBL cells, cDNA formed and cDNA was ligated into Eco R1 linkers. Ligated cDNA was inserted into the Eco R1 site of λgt10 phage cloning vehicle (Gigapak® Stratagene, San Diego, Calif.) according to manufacturer's instructions. Phage were amplified, plated at densities densities of approximately 20,000 phage per 15 cm plate and phage lifts were performed, as described in Maniatis et al., *Molecular Biology: A Laboratory Manual*, Cold Spring Harbor Laboratory, New York, 1982, pages 316–328. A murine probe was constructed corresponding to the coding region of murine CD40-L from nucleotide 13 to nucleotide 793 of SEQ ID NO:1 and FIGS. 1A and 1B. This probe was hybridized to to the PBL library phage lifts under conditions of moderate to severe stringency. Briefly, hybridization conditions were 6×SSC, 1×Denhardt's solution, 2 mM EDTA, 0.5% NP4(Nonidet P-40 detergent) at 63° C. overnight. This was followed by washing in 3×SSC, 0.1% SDS for three hours at 55° C., followed by overnight exposure to X-Ray film. Positive plaques were identified at a frequency of approximately 1 per 1000 plaques. Positive plaques were purified twice and cDNA was prepared from amplified cultures.

One can utilize the murine or human CD40-L cDNA sequences disclosed herein to obtain cDNAs encoding other mammalian homologs of murine or human CD40-L by cross-species hybridization techniques. Briefly, an oligonucleotide probe is created from the nucleotide sequence of the extracellular region of murine CD40-L as described in FIGS. 1A and 1B (SEQ ID NO:1) or human CD40-L as described in FIGS. 2A and 2B (SEQ ID NO:11). This probe can be made by standard techniques, such as those described in Maniatis et al. supra. The murine or human probe is used to screen a mammalian cDNA library or genomic library under moderate stringency conditions. Examples of mammalian cDNA or genomic libraries include, for cDNA, a library made from the mammal's peripheral blood lymphocytes. Alternatively, various cDNA libraries or mRNAs isolated from various cell lines can be screened by Northern hybridization to determine a suitable source of mammalian CD40-L DNA or mRNA.

Recombinant expression vectors for expression of CD40-L by recombinant DNA techniques include a CD40-L DNA sequence comprising a synthetic or cDNA-derived DNA fragment encoding a CD40-L polypeptide, operably linked to a suitable transcriptional or translational regulatory nucleotide sequence, such as one derived from a mammalian, microbial, viral, or insect gene. Examples of regulatory sequences include sequences having a regulatory role in gene expression (e.g., a transcriptional promoter or enhancer), optionally an operator sequence to control transcription, a sequence encoding an mRNA ribosomal binding site, and appropriate sequences which control transcription and translation initiation and termination. Nucleotide sequences are operably linked when the regulatory sequence functionally relates to the CD40-L DNA sequence. Thus, a promoter nucleotide sequence is operably linked to a CD40-L DNA sequence if the promoter nucleotide sequence controls the transcription of the CD40-L DNA sequence. Still further, a ribosome binding site may be operably linked to a sequence for a CD40-L polypeptide if the ribosome binding site is positioned within the vector to encourage translation. In addition, sequences encoding signal peptides can be incorporated into expression vectors. For example, a DNA sequence for a signal peptide (secretory leader) may be operably linked to a CD40-L DNA sequence. The signal peptide is expressed as a precursor amino acid sequence which enables improved extracellular secretion of translated fusion polypeptide by a yeast host cell.

Suitable host cells for expression of CD40-L polypeptides include prokaryotes, yeast or higher eukaryotic cells. Prokaryotes include gram negative or gram positive organisms, for example, *E. coli* or Bacilli. Suitable prokaryotic host cells for transformation include, for example, *E. coli, Bacillus subtilis, Salmonella typhimurium*, and various other species within the genera Pseudomonas, Streptomyces, and Staphylococcus. Higher eukaryotic cells include established cell lines of mammalian origin. Cell-free translation systems could also be employed to produce CD40-L polypeptides using RNAs derived from DNA constructs disclosed herein. Appropriate cloning and expression vectors for use with bacterial, fungal, yeast, and mammalian cellular hosts are described, for example, in Pouwels et al. *Cloning Vectors: A Laboratory Manual*, Elsevier, New York, (1985).

In a prokaryotic host cell, such as *E. coli*, a CD40-L polypeptide or analog may include an N-terminal methionine residue to facilitate expression of the recombinant polypeptide in the prokaryotic host cell. The N-terminal Met may be cleaved from the expressed recombinant CD40-L polypeptide. Prokaryotic host cells may be used for expression of CD40-L polypeptides that do not require extensive proteolytic or disulfide processing.

The expression vectors carrying the recombinant CD40-L DNA sequence are transfected or transformed into a substantially homogeneous culture of a suitable host microorganism or mammalian cell line. Transformed host cells are cells which have been transformed or transfected with nucleotide sequences encoding CD40-L polypeptides and express CD40-L polypeptides. Expressed CD40-L polypeptides will be located within the host cell and/or secreted into culture supernatant fluid, depending upon the nature of the host cell and the gene construct inserted into the host cell.

Expression vectors transfected into prokaryotic host cells generally comprise one or more phenotypic selectable markers. A phenotypic selectable marker is, for example, a gene encoding a protein that confers antibiotic resistance or that supplies an autotrophic requirement, and an origin of replication recognized by the host to ensure amplification within the host. Other useful expression vectors for prokaryotic host cells include a selectable marker of bacterial origin derived from commercially available plasmids. This selectable marker can comprise genetic elements of the cloning vector pBR322 (ATCC 37017). pBR322 contains genes for ampicillin and tetracycline resistance and thus provides simple means for identifying transformed cells. The pBR322 "backbone" sections are combined with an appropriate promoter and a CD40-L DNA sequence. Other commercially vectors include, for example, pKK223-3 (Pharmacia Fine Chemicals, Uppsala, Sweden) and pGEM1 (Promega Biotec, Madison, Wis., USA).

Promoter sequences are commonly used for recombinant prokaryotic host cell expression vectors. Common promoter sequences include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage λ $P_L$ promoter and a cI857ts thermolabile repressor sequence. Plasmid vectors available from the American Type Culture Collection which incorporate derivatives of the λ $P_L$ promoter include plasmid pHUB2 (resident in *E. coli* strain JMB9 (ATCC 37092)) and pPLc28 (resident in *E. coli* RR1 (ATCC 53082)).

CD40-L may be expressed in yeast host cells, preferably from the Saccharomyces genus (e.g., *S. cerevisiae*). Other genera of yeast, such as Pichia or Kluyveromyces, may also be employed. Yeast vectors will often contain an origin of replication sequence from a 2μ yeast plasmid, an autonomously replicating sequence (ARS), a promoter region, sequences for polyadenylation, and sequences for transcription termination. Preferably, yeast vectors include an origin of replication sequence and selectable marker. Suitable promoter sequences for yeast vectors include promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657.

Yeast vectors can be assembled, for example, using DNA sequences from pBR322 for selection and replication in *E. coli* ($Amp^r$ gene and origin of replication). Other yeast DNA sequences that can be included in a yeast expression construct include a glucose-repressible ADH2 promoter and a-factor secretion leader. The ADH2 promoter has been described by Russell et al. (*J. Biol. Chem.* 258:2674, 1982) and Beier et al. (*Nature* 300:724, 1982). The yeast α-factor leader sequence directs secretion of heterologous polypeptides. The a α-factor leader sequence is often inserted between the promoter sequence and the structural gene sequence. See, e.g., Kurjan et al., *Cell* 30:933, 1982 and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems could also be employed to express recombinant CD40-L polypeptides. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines. Suitable mammalian expression vectors include nontranscribed elements such as an origin of replication, a promoter sequence, an enhancer linked to the structural gene, other 5' or 3' flanking nontranscribed sequences, such as ribosome binding sites, a polyadenylation site, splice donor and acceptor sites, and transcriptional termination sequences.

Transcriptional and translational control sequences for mammalian host cell expression vectors may be excised from viral genomes. For example, commonly used mammalian cell promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Exemplary mammalian expression vectors can be constructed as disclosed by Okayama and Berg (*Mol. Cell. Biol.* 3:280, 1983). A useful high expression vector, PMLSV N1/N4, described by Cosman et al., *Nature* 312:768, 1984 has been deposited as ATCC 39890. Additional useful mammalian expression vectors are described in EP-A-0367566, and in U.S. patent application Ser. No. 07/701,415, filed May 16, 1991, incorporated by reference herein. For expression of a type II protein extracellular region, such as CD40-L, a heterologous signal sequence should be added, such as the signal sequence for interleukin-7 (IL-7) described in U.S. Pat. No. 4,965,195, or the signal sequence for interleukin-2 receptor described in U.S. patent application Ser. No. 06/626,667 filed on Jul. 2, 1984 (now U.S. Pat. No. 5,317,087).

Human or murine CD40-L can be made in membrane-bound form when an intracellular and transmembrane regions are included or in soluble form with only the extracellular domain. We expressed full length murine CD40-L in mammalian cells to yield cells expressing membrane-bound murine CD40-L. CV1 cells were transfected with a cDNA shown in FIGS. 1A and 1B (SEQ ID NO:1) in HAVEO vector or CV1 cells were transfected with HAVEO empty vector using techniques described in Example 6 herein. This yielded transfected CV1 cells expressing membrane-bound murine CD40-L. These cells were used as a source of membrane-bound murine CD40-L for the series of experiments reported in Examples 10–13 reported below.

Purification of Recombinant CD40-L Polypeptides

CD40-L polypeptides may be prepared by culturing transformed host cells under culture conditions necessary to express CD40-L polypeptides. The resulting expressed polypeptides may then be purified from culture media or cell extracts. A CD40-L polypeptide, if desired, may be concentrated using a commercially available protein concentration filter, for example, an Amicon or Millipore PELLICON™ ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reverse-phase high performance liquid chromatography (RP-HPLC) steps employing hydrophobic RP-HPLC media, (e.g., silica gel having pendant methyl or other aliphatic groups) can be employed to further purify CD40-L. Some or all of the foregoing purification steps, in various combinations, can also be employed to provide a substantially homogeneous recombinant protein.

It is also possible to utilize an affinity column comprising CD40 ligand binding domain to affinity-purify expressed CD40-L polypeptides. CD40-L polypeptides can be removed from an affinity column in a high salt elution buffer and then dialyzed into a lower salt buffer for use.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express CD40-L as a secreted polypeptide. This simplifies purification. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

Administration of CD40-L Compositions

The present invention provides therapeutic compositions comprising an effective amount of CD40-L in a suitable diluent or carrier and methods of treating mammals using the compositions. For therapeutic use, purified CD40-L or a biologically active analog thereof is administered to a patient, preferably a human, for treatment in a manner appropriate to the indication. Thus, for example, CD40-L pharmaceutical compositions (for example, in the form of a soluble extracellular domain, or a fragment thereof) which is administered to achieve a desired therapeutic effect can be given by bolus injection, continuous infusion, sustained release from implants, or other suitable technique. Typically, a CD40-L therapeutic agent will be administered in the form of a pharmaceutical composition comprising purified CD40-L polypeptide in conjunction with physiologically acceptable carriers, excipients or diluents. Such carriers will be nontoxic to patients at the dosages and concentrations employed. Ordinarily, the preparation of such compositions entails combining a CD40-L polypeptide with buffers, antioxidants such as ascorbic acid, low molecular weight (less than about 10 residues) polypeptides, proteins, amino acids, carbohydrates including glucose, sucrose or dextrans, chelating agents such as EDTA, glutathione and other stabilizers and excipients. Neutral buffered saline or saline mixed with conspecific serum albumin are exemplary appropriate diluents. CD40-L sense or antisense oligonucleotides may be administered in vivo by administering an effective amount of a vector containing a nucleic acid sequence that encodes and effective antisense or sense oligonucleotide. Additionally, CD40-L sense or antisense oligonucleotides may be administered ex vivo by removing cells containing CD40-L DNA or mRNA from an individual, incorporating an antisense or sense oligonucleotide into the cells using gene transfer techniques, and re-infusing the cells into the individual.

The following examples are intended to illustrate particular embodiments and not limit the scope of the invention.

EXAMPLE 1

This example describes construction of a CD40/Fc DNA construct to express a soluble CD40/Fc fusion protein for use in detecting cDNA clones encoding a CD40 ligand. The cDNA sequence of the extracellular region or ligand binding domain of complete CD40 human receptor sequence was obtained using polymerase chain reaction (PCR) techniques, and is based upon the sequence published in Stamenkovic et al., supra. A CD40 plasmid (CDM8) was used as a template for PCR amplification. CDM8 is described in Stamenkovic et al. and was obtained from the authors. A PCR technique (Sarki et al., Science 239:487, 1988) was employed using 5' (upstream) and 3' (downstream) oligonucleotide primers to amplify the DNA sequences encoding CD40 extracellular ligand binding domain. Upstream oligonucleotide primer 5'-CCGTCGACCACCATGGTTCGTCTGCC-3' (SEQ ID NO:5) introduces a Sal 1 site upstream from an initiator methionine of CD40 and a downstream oligonucleotide primer 5'-ACAAGATCTGGGCTCTACGTATCTCAGCCGATCCTGGGGAC-3' (SEQ ID NO:7) that inserts amino acids Tyr Val Glu Pro Arg (SEQ ID NO:8) after amino acid 193 of CD40. Glu and Pro are the first two amino acids of a hinge region of human IgG1, and are followed by a Bgl II restriction site that was used to fuse the extracellular domain of CD40 to the remained of human IgG1 Fc region.

The DNA construct pDC406/CD40/Fc was transfected into the monkey kidney cell line CV-1/EBNA (ATCC CRL 10478). The pDC406 plasmid includes regulatory sequences derived from SV40, human immunodeficiency virus (HIV), and Epstein-Barr virus (EBV). The CV-1/EBNA cell line was derived by transfection of the CV-1 cell line with a gene encoding Epstein-Barr virus nuclear antigen-1 (EBNA-1) that constitutively expresses EBNA-1 driven from the human CMV intermediate-early enhancer/promoter. The EBNA-1 gene allows for episomal replication of expression vectors, such as pDC406, that contain the EBV origin of replication.

Once cells expressing the fusion construct were identified, large scale cultures of transfected cells were grown to accumulate supernatant from cells expressing CD40/Fc. The CD40/Fc fusion protein in supernatant fluid was purified by affinity purification. Briefly, one liter of culture supernatant containing the CD40/Fc fusion protein was purified by filtering mammalian cell supernatants (e.g., in a 0.45 $\mu$ filter) and applying filtrate to a protein A/G antibody affinity column (Schleicher and Schuell, Keene, N.H.) at 4° C. at a flow rate of 80 ml/hr for a 1.5 cm×12.0 cm column. The column was washed with 0.5 M NaCl in PBS (phosphate buffered saline) until free protein could not be detected in wash buffer. Finally, the column was washed with PBS. Bound fusion protein was eluted from the column with 25 mM citrate buffer, pH 2.8, and brought to pH 7 with 500 mM Hepes buffer, pH 9.1. Silver-strained SDS gels of the eluted CD40/Fc fusion protein showed it to be >98% pure.

Purified CD40/Fc fusion protein was iodinated with $^{125}$I using a commercially available solid phase agent (IODO-GEN®, 1,3,4,6-tetrachloro-3α-diphenylglycouril Pierce). In this procedure, 5 $\mu$g of IODO-GEN were plated at the bottom of a 10×75 mm glass tube and incubated for twenty minutes at 4° C. with 75 $\mu$l of 0.1 M sodium phosphate, pH 7.4 and 20 $\mu$l (2 mCi) Na$^{125}$I. The solution was then transferred to a second glass tube containing 5 $\mu$g of CD40/Fc in 45 $\mu$l PBS and this reaction mixture was incubated for twenty minutes at 4° C. The reaction mixture was fractionated by gel filtration on a 2 ml bed volume of Sephadex® G-25 (Sigma), and then equilibrated in RPMI 1640 medium containing 2.5% (v/v) bovine serum albumin (BSA), 0.2% (v/v) sodium azide and 20 mM Hepes, pH 7.4 binding medium. The final pool of $^{125}$I CD40/Fc was diluted to a working stock solution of $1\times10^{-7}$ M in binding medium and stored for up to one month at 4° C. without detectable loss of receptor binding activity.

Approximately 50%–60% label incorporation was observed. Radioiodination yielded specific activities in the range of $1\times10^{15}$ to $5\times10^{15}$ cpm/nmole (0.42–2.0 atoms of radioactive iodine per molecule of protein). SDS polyacrylamide gel electrophoresis (SDS-PAGE) revealed a single labeled polypeptide consistent with expected values. The labeled fusion protein was greater than 98% trichloroacetic acid (TCA) precipitable, indicating that the $^{125}$I was covalently bound to the protein.

EXAMPLE 2

This example describes selection of a cell line putatively expressing CD40-L. Several cell lines were screened using the radioiodinated CD40/Fc fusion protein described in Example 1. Briefly, quantitative binding studies were performed according to standard methodology, and Scatchard plots were derived for the various cell lines. A clonal cell line (EL4, ATCC Catalog TIP 39) a murine thymoma cell line was identified and sorted. Prior to sorting, EL-4 cells were found to express approximately 450 molecules of CD40-L per cell. The seventh sort cells were called EL-40.7 and were grown and found to express approximately 10,000 molecules of CD40-L per cell. Lastly, the ninth sort cells were called EL-40.9 and were grown and found to express approximately 15,000 molecules of CD40-L per cell.

EXAMPLE 3

This example describes preparation of a cDNA library for expression cloning of murine CD40-L. The library was prepared from a fifth sorted clone of a mouse thymoma cell line EL-4 (ATCC TIB 39), called EL-40.5. EL-40.5 cells were EL4 cells sorted five times with biotinylated CD40/Fc fusion protein in a FACS (fluorescence activated cell sorter). A cDNA library was made from RNA obtained from EL-40.5 cells essentially as described in U.S. Pat. No. 4,968,607, the disclosure of which is incorporated by reference herein. Briefly, a cDNA library was constructed by reverse transcription of poly (A)$^+$ mRNA isolated from the total RNA extracted from the EL-40.5 cell line. The library construction technique was substantially similar to that described by Ausubel et al., eds., *Current Protocols In Molecular Biology*, Vol. 1, (1987). Poly (A)$^+$ mRNA was isolated by oligo dT cellulose chromatography and double-stranded cDNA was made substantially as described by Gubler et al., *Gene* 25:263, 1983. Poly(A)$^+$ mRNA fragments were converted to RNA-cDNA hybrids by reverse transcriptase using random hexanucleotides as primers. The RNA-cDNA hybrids were then converted into double-stranded cDNA fragments using RNAase H in combination with DNA polymerase I. The resulting double-stranded cDNA was blunt-ended with T4 DNA polymerase. Sal I adaptors 5'-TCG ACT GGA ACG AGA CGA CCT GCT-3' (SEQ ID NO:25) GA CCT TGC TCT GCT GGA CGA-5' (SEQ ID NO:26) were ligated to 5' ends of resulting blunt-ended cDNA, as described in Haymerle et al., *Nucleic Acids Res.* 14:8615, 1986. Non-ligated adaptors were removed by gel filtration chromatography at 68° C. This left 24 nucleotide non-self-complementary overhangs on cDNA. The same procedure was used to convert 5' Sal I ends of the mammalian expression vector pDC406 to 24 nucleotide overhangs complementary to those added to cDNA. Optimal proportions of adaptored vector and cDNA were ligated in the presence of T4 polynucleotide kinase. Dialyzed ligation mixtures were electroporated into *E. coli* strain DH5α and transformants selected on ampicillin plates.

Plasmid DNA was isolated from pools consisting of approximately 2,000 clones of transformed *E. coli* per pool. The isolated DNA was transfected into a sub-confluent layer of CV1-EBNA cells using DEAE-dextran followed by chloroquine treatment substantially according to the procedures described in Luthman et al., *Nucl. Acids Res.* 11:1295, 1983 and McCutchan et al., *J. Natl. Cancer Inst.* 41:351, 1986.

CV1-EBNA cells were maintained in complete medium (Dulbecco's modified Eagles' media containing 10% (v/v fetal calf serum, 50 U/ml penicillin, 50 U/ml streptomycin, and 2 mM L-glutamine) and were plated to a density of approximately 2×10$^5$ cells/well in single-well chambered slides (Lab-Tek). The slides were pre-treated with 1 ml human fibronectin (10 µg/ml PBS) for 30 minutes followed by a single washing with PBS. Media was removed from adherent cells growing in a layer and replaced with 1.5 ml complete medium containing 66.6 µM chloroquine sulfate. About 0.2 ml of a DNA solution (2 µg DNA, 0.5 mg/ml DEAE-dextran in complete medium containing chloroquine) was added to the cells and the mixture was incubated at 37° C. for about five hours. Following incubation, media was removed and the cells were shocked by addition of complete medium containing 10% DMSO (dimethylsulfoxide) for 2.5–20 minutes. Shocking was followed by replacement of the solution with fresh complete medium. The cells were grown in culture for two to three days to permit transient expression of the inserted DNA sequences. These conditions led to a 30% to 80% transfection frequency in surviving CV1-EBNA cells.

EXAMPLE 4

This example describes screening of the expression cloning library made in Example 3 with a labeled CD40/Fc fusion protein made in Example 1. After 48–72 hours, transfected monolayers of CV1-EBNA cells made in Example 3 were assayed by slide autoradiography for expression of CD40-L using radioiodinated CD40/Fc fusion protein as prepared in Example 1. Transfected CV1-EBNA cells were washed once with binding medium (RPMI 1640 containing 25 mg/ml bovine serum albumin (BSA), 2 mg/ml sodium azide, 20 mM Hepes pH 7.2, and 50 mg/ml nonfat dry milk) and incubated for 2 hours at 4° C. ml in binding medium containing 1×10$^{-9}$ M $^{125}$I-CD40/Fc fusion protein. After incubation, cells in the chambered slides were washed three times with binding buffer, followed by two washes with PBS, (pH 7.3) to remove unbound radiolabeled fusion protein.

The cells were fixed by incubating in 10% gluteraldehyde in PBS (30 minutes at room temperature), washed twice in PBS and air-dried. The slides were dipped in Kodak GTNB-2 photographic emulsion (6× dilution in water) and exposed in the dark for two to four days days at room temperature in a light-proof box. The slides were developed in Kodak D19 developer, rinsed in water and fixed in Agfa G433C fixer. The slides were individually examined under a microscope at 25–40× magnification. Positive slides showing cells expressing CD40-L were identified by the presence of autoradiographic silver grains against a light background.

One pool containing approximately 2000 individual clones was identified as potentially positive for binding the CD40/Fc fusion protein. The pool was titered and plated to provide plates containing approximately 200 colonies each. Each plate was scraped to provide pooled plasmid DNA for transfection into CV1-EBNA cells according to the same procedure described above. The smaller pools were screened by slide autoradiography as described previously. One of the smaller pools contained clones that were positive for CD40-L as indicated by the presence of an expressed gene product capable of binding to the CD40/Fc fusion protein.

The positive smaller pool was titered and plated to obtain individual colonies. Approximately 400 individual colonies were picked and inoculated into culture medium in individual wells of 96-well plates. Cultures were mixed by pooling rows and columns and the mixed cultures were used to prepare DNA for a final round of transfection and screening. An intersection of a positive row and and a positive column indicated a potential positive colony. Ten potential positive colonies (i.e., candidate clones) were identified. DNA was isolated from each candidate clone, retransfected and rescreened. Five candidate clones were positive by binding to CD40/Fc. All five positive candidate clones contained a cDNA insert of 1468 nucleotides, as determined by dideoxynucleotide sequencing. The cDNA coding region of the CD40-L clone corresponds to the sequence of FIGS. 1A and 1B and SEQ ID NO:1.

A cloning vector containing murine CD40-L sequence, designated pDC406-mCD40-L, was deposited with the American Type Culture Collection, Rockville, Md. (ATCC) on Dec. 6, 1991, under accession number 68872. The nucleotide sequence and predicted amino acid sequence of this clone are illustrated in SEQ ID NO:1 and in FIGS. 1A and 1B.

EXAMPLE 5

This example illustrates a cross-species hybridization technique which was used to isolate a human CD40-L homolog using a probe designed from the sequence of murine CD40-L. A murine CD40-L probe was produced by excising the coding region from murine CD40-L clone pDC406-CD40-L (nucleotide 13 through 793) and $^{32}$P-labeling the fragment using random primers (Boehringer-Mannheim).

A human peripheral blood lymphocyte (PBL) cDNA library was constructed in a λ phage vector using λgt10 arms and packaged in vitro using a commercially available kit (Gigapak® Stratagene, San Diego, Calif.) according to the manufacturer's instructions. The PBL cells were obtained from normal human volunteers and treated with 10 ng/ml of OKT3 (an anti-CD3 antibody), and 10 ng/ml of human IL-2 (Immunex, Seattle, Wash.) for six days. The PBL cells were washed and stimulated with 500 ng/ml ionomycin (Calbiochem) and 10 ng/ml PMA (Sigma) for four hours. Messenger RNA and cDNA were obtained from the stimulated PBL cells and packaged into λg10 phage vectors (Gigapak® Stratagene) according to manufacturer's instructions.

The murine probe was hybridized to phage cDNA in 6×SSC (15 mM trisodium citrate, and 165 mM sodium chloride), 1×Denhardt's solution, 2 mM EDTA, 0.5% Np40 at 63° C. overnight. Hybridization was followed by extensive washing in 3×SSC, 0.1% SDS at approximately 55° C. for three hours. Specific bands were visualized by autoradiography.

A cloning vector containing human CD40-L sequence, designated hCD40-L, was deposited with the American Type Culture Collection, Rockville, Md. (ATCC) on Dec. 6, 1991, under accession number 68873. The nucleotide sequence and predicted amino acid sequence of this clone are illustrated SEQ ID NO:11 and in FIGS. 2A and 2B.

EXAMPLE 6

This example illustrates the expression of membrane-bound murine CD40-L in CV1-EBNA cells. Murine CD40-L cDNA in HAVEO vector or empty HAVEO vector were transfected into CV1 EBNA cells using standard techniques, such as those described in McMahan et al. et al. *EMBO J.* 10:2821, 1991 and in Example 3 herein. Briefly, CV1 EBNA cells were plated at a density of 2×10$^6$ cells per 10 cm dish in 10 ml of Dulbecco's Minimal Essential Medium supplemented with 10% fetal calf serum (Medium). The cells were allowed to adhere overnight at 37° C. The Medium was replaced with 1.5 ml of Medium containing 66.7 μM chloroquine and a DNA mixture containing 5 μg of cDNA encoding mCD40-L. Medium containing 175 μl, and 25 μl of DEAE dextran (4 mg/ml in PBS) was also added to the cells. The cells and cDNA were incubated at 37° C. for 5 hours. The cDNA mixture was removed and the cells were shocked with 1 ml of fresh Medium containing 10% DMSO for 2.5 min. The Medium was replaced with fresh Medium and the cells were grown for at least 3 days.

EXAMPLE 7

This example illustrates the preparation of monoclonal antibodies to CD40-L. Preparations of purified murine CD40-L or human CD40-L are prepared by COS cell expression and CD40/Fc affinity purification as described herein. Purified CD40-L or transfected cells expressing membrane-bound CD40-L can generate monoclonal antibodies against CD40-L using conventional techniques, for example, those techniques described in U.S. Pat. No. 4,411,993. Briefly, mice are immunized with human CD40-L as an immunogen emulsified in complete Freund's adjuvant or another suitable adjuvant such as incomplete Freund's adjuvant or Ribi adjuvant R700 (Ribi, Hamilton, Mt.) or another suitable adjuvant, and injected in amounts ranging from 10–100 μg subcutaneously or intraperitoneally. Rats (i.e. Lewis rats) are immunized with murine CD40-L as an immunogen in a similar manner. Ten days to three weeks later, the immunized animals are boosted with additional CD40-L emulsified in incomplete Freund's adjuvant. Mice are periodically boosted thereafter on a weekly, bi-weekly or every third week immunization schedule. Serum samples are periodically taken by retro-orbital bleeding or tail-tip excision for testing by dot blot assay, ELISA (Enzyme-Linked Immunosorbent Assay), or FACS analysis, for CD40-L antibodies.

Following detection of an appropriate antibody titer, positive animals are provided one last intravenous injection of CD40-L in saline. Three to four days later, the animals are sacrificed, spleen cells harvested, and spleen cells are fused to a murine myeloma cell line (e.g., NS1 or Ag 8.653). Fusions generate hybridoma cells, which are plated in multiple microtiter plates in a selective medium containing HAT (hypoxanthine, aminopterin and thymidine) to inhibit proliferation of non-fused cells, myeloma-myeloma hybrids, and spleen cell-spleen cell hybrids.

The hybridoma cells are screened by ELISA for reactivity against purified CD40-L by adaptations of the techniques disclosed in Engvall et al., *Immunochem.* 8:871, 1971 and in U.S. Pat. No. 4,703,004, or by or FACS as described herein. Positive hybridoma cells can be cloned in soft agar or another, similar medium, or by limiting dilution, to insure that a final cell population is derived from a single hybridoma cell. The cloned hybridoma cells are injected intraperitoneally into syngeneic mice (or rats) to produce ascites containing high concentrations of anti-CD40-L monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can also be used, as can affinity chromatography based upon binding to CD40-L.

EXAMPLE 8

This example illustrates anti-allergy therapeutic effects of sCD40 and CD40/Fc fusion protein. Soluble CD40 and CD40/Fc were tested for their ability to inhibit IL-4 (5 ng/ml) induced IgE secretion in a two donor MLC system The data from three experiments are presented in Table 1.

TABLE 1

| | IgE (ng/ml) | | |
|---|---|---|---|
| Addition | Exp. 1 | Exp. 2 | Exp. 3 |
| medium | <0.1 | <0.1 | <0.1 |
| IL-4 | 24 | 47 | 54 |

TABLE 1-continued

| | IgE (ng/ml) | | |
|---|---|---|---|
| Addition | Exp. 1 | Exp. 2 | Exp. 3 |
| IL-4 + sCD40 (0.1 μg/ml) | 19 | nd | 38 |
| IL-4 + sCD40 (0.3 μg/ml) | 14 | 29 | 24 |
| IL-4 + sCD40 (1 μg/ml) | 10 | 24 | 8 |
| IL-4 + sCD40 (3 μg/ml) | 7 | 19 | 2 |
| IL-4 + IL-7R/Fc (10 μg/ml) | 21 | nd | 58 |

IgE levels were measured after 12 days in culture by an ELISA procedure. Briefly, flat-bottomed 96-well microtiter plates (Corning) were coated with mouse mAb anti-human IgE (Zymed) at 1:500 dilution in PBS (phosphate buffered saline). After washing 3×, a blocking step was performed using 5% non-fat dried milk, followed by titration of human IgE standards or test supernatants. After washing 3×, biotinylated goat anti-human IgE (Kirkegaard and Perry) was added at a 1:500 dilution. This was followed by further washing and then addition of streptavidin-HRP (Zymed) at a 1:500 dilution. After further washing, the reaction was developed using TMB substrate (Kirkegaard and Perry) and absorbance measured at 520 nm. All washing steps were carried out in PBS plus 0.05% Tween. All incubation steps were performed at volumes of 100 μl/well for one hour at room temperature. The sensitivity of this assay is 100 pg/ml.

EXAMPLE 9

This example illustrates the effects of sCD40 and CD40/Fc fusion protein to inhibit soluble CD23 shedding from IL-4 (5 ng/ml) stimulated B cells. Soluble CD40 and CD40/Fc were tested for their ability to inhibit IL-4-induced sCD23 shedding in a two donor MLC system The data from three experiments are presented in Table 2.

TABLE 2

| | sCD23 (ng/ml) | | | | | |
|---|---|---|---|---|---|---|
| | Exp. 1 | | Exp. 2 | | Exp. 3 | |
| Addition | day 6 | day 12 | day 6 | day 12 | day 6 | day 12 |
| E⁻ + medium | 55 | <0.5 | 24 | 10 | 10 | 5 |
| +IL-4 | 115 | 55 | 96 | 62 | 44 | 27 |
| +IL-4 + sCD40 (1 μg/ml) | nd | nd | 88 | 36 | 38 | 9 |
| +IL-4 + sCD40 (3 μg/ml) | 97 | 4 | 82 | 31 | 40 | 4 |
| +IL-4 + sCD40 (10 μg/ml) | nd | nd | 72 | 28 | nd | nd |
| +IL-4 + IL-7R/Fc (3 μg/ml) | 111 | 48 | 103 | 67 | 40 | 22 |
| PBM + medium | 12 | <0.5 | 15 | 5 | 3 | 10 |
| +IL-4 | 39 | 255 | 47 | 22 | 48 | 26 |
| +IL-4 + sCD40 (1 μg/ml) | nd | nd | 44 | 18 | 46 | 18 |
| +IL-4 + sCD40 (3 μg/ml) | 24 | 6 | 37 | 11 | 45 | 12 |
| +IL-4 + sCD40 (10 μg/ml) | nd | nd | 28 | 5 | nd | nd |
| +IL-4 + IL-7R/Fc (3 μg/ml) | 35 | 26 | 43 | 20 | 50 | 23 |

Soluble CD23 levels were measured after 6 and 12 days in culture by a commercial sCD23 ELISA detection kit (Binding Site, San Diego, Calif.). The sensitivity limit was 500 pg/ml. Approximately 1×10⁵ cells per well were cultured in triplicate in round-bottomed 96-well microtiter plates (Intermountain Scientific, Bountiful Utah) for the indicated time in the presence or absence of additives as indicated in Table 2. The results show anti-allergy effects of sCD40. Similar studies were run with CD40/Fc (data not shown) instead of sCD40, and similar results were obtained. Accordingly, these data in Examples 8 and 9 illustrate an anti-allergy property for CD40.

EXAMPLE 10

This example illustrates B cell proliferative activity of membrane-bound murine CD40-L for human B cells. Human peripheral blood mononuclear cells (PBMC) were isolated from peripheral blood from normal volunteers by density gradient centrifugation over Histopaque® (Sigma, St. Louis, Mo.) T cell-depleted preparations of cells (E−) were obtained by removing T cells by rosetting with 2-aminoethylisothiouronium bromide-treated SRBC (sheep red blood cells) and further density gradient centrifugation over Histopaque®. B cell proliferation assays were conducted with E⁻ preparations in RPMI media with added 10% heat-inactivated fetal bovine serum (FBS) at 37° C. in a 10% $CO_2$ atmosphere. Approximately $1 \times 10^5$ E⁻ cells per well were cultured in triplicate in flat-bottomed 96-well microtiter plates (Coming) for 7 days in the presence of transfected CV1 EBNA cells (described in Example 6). The CV1 EBNA cells were transfected with murine CD40-L cDNA or empty vector. The cells were pulsed with 1 μCi/well of tritiated thymidine (25 Ci/nmole Amersham, Arlington Heights, Ill.) for the final eight hours of culture. Cells were harvested onto glass fiber discs with an automated cell harvester and incorporated cpm were measured by liquid scintillation spectrometry.

Figure 4B:
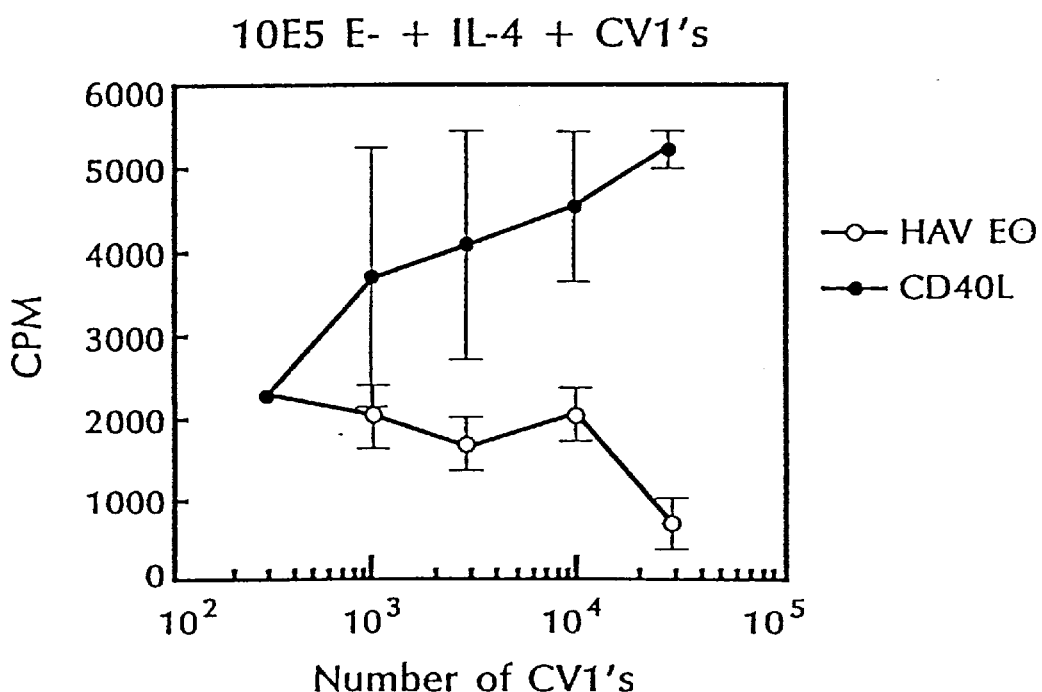
Figure 5:
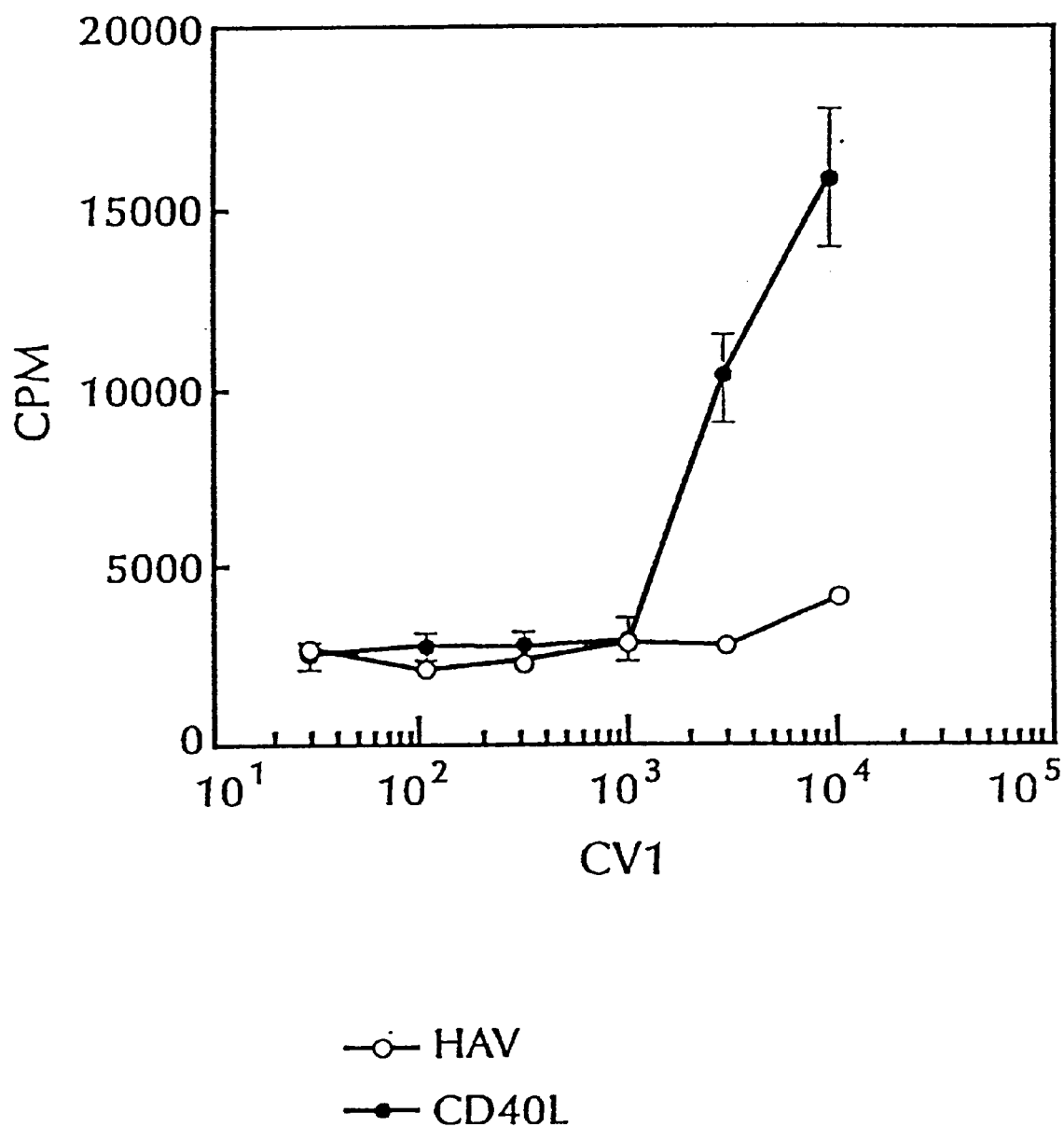
FIG. 5 illustrates a second determination of T cell depleted PBMC proliferation with addition of bound murine CD40-L and 10 ng/ml of IL-4. These data show no co-mitogenic effect of IL-4 but continued strong mitogenic effect of bound CD40-L.

FIG. 4a shows a comparison of human B cell proliferation of CV1 EBNA cells transfected with empty vector (HAVEO) or with murine CD40-L cDNA in HAVEO vector. These data show that membrane-bound CD40-L stimulates human B cell proliferation in the absence of a co-mitogen. FIG. 4b shows a similar experiment, except that 10 ng/ml of human IL-4 was added to the cultures. In this experiment, IL-4 slightly enhances the B cell mitogenic activity of membrane-bound murine CD40-L. FIG. 5 is a repeat of the experiment shown in FIG. 4b. However, when the experiment was repeated, there was no evidence of IL-4 co-mitogenic activity. There was repeated evidence of CD40-L mitogenic activity. Accordingly, membrane-bound CD40-L stimulates proliferation of human B cells.

EXAMPLE 11

This example illustrates the effect of membrane-bound murine CD40-L to stimulate IgE production and CD23 shedding from E⁻ cells isolated in Example 10. Approximately $1 \times 10^5$ cells/well were cultured in triplicate round bottomed 96-well Nunc microtiter plates (Intermountain Scientific, Bountiful Utah.) in Iscove's Modified Dulbecco's Medium (IMDM) plus 10% FCS in a humidified atmosphere of 10% $CO_2$. Medium was supplemented with 50 μg/ml human transferrin (Sigma), 0.5% bovine serum albumin (Sigma) and 1 μg/ml of each of oleic, linoleic and palmitic acids (Sigma). The E⁻ cells were cultured for 10 days in the presence of 5 ng/ml human IL-4. A titration of CV1 EBNA cells transfected with murine CD40-L or empty vector were added. After ten days, culture supernatants were assayed for IgE by the ELISA procedure described in Example 8 or for CD23 shedding by the procedure described in Example 9.

Figure 6:
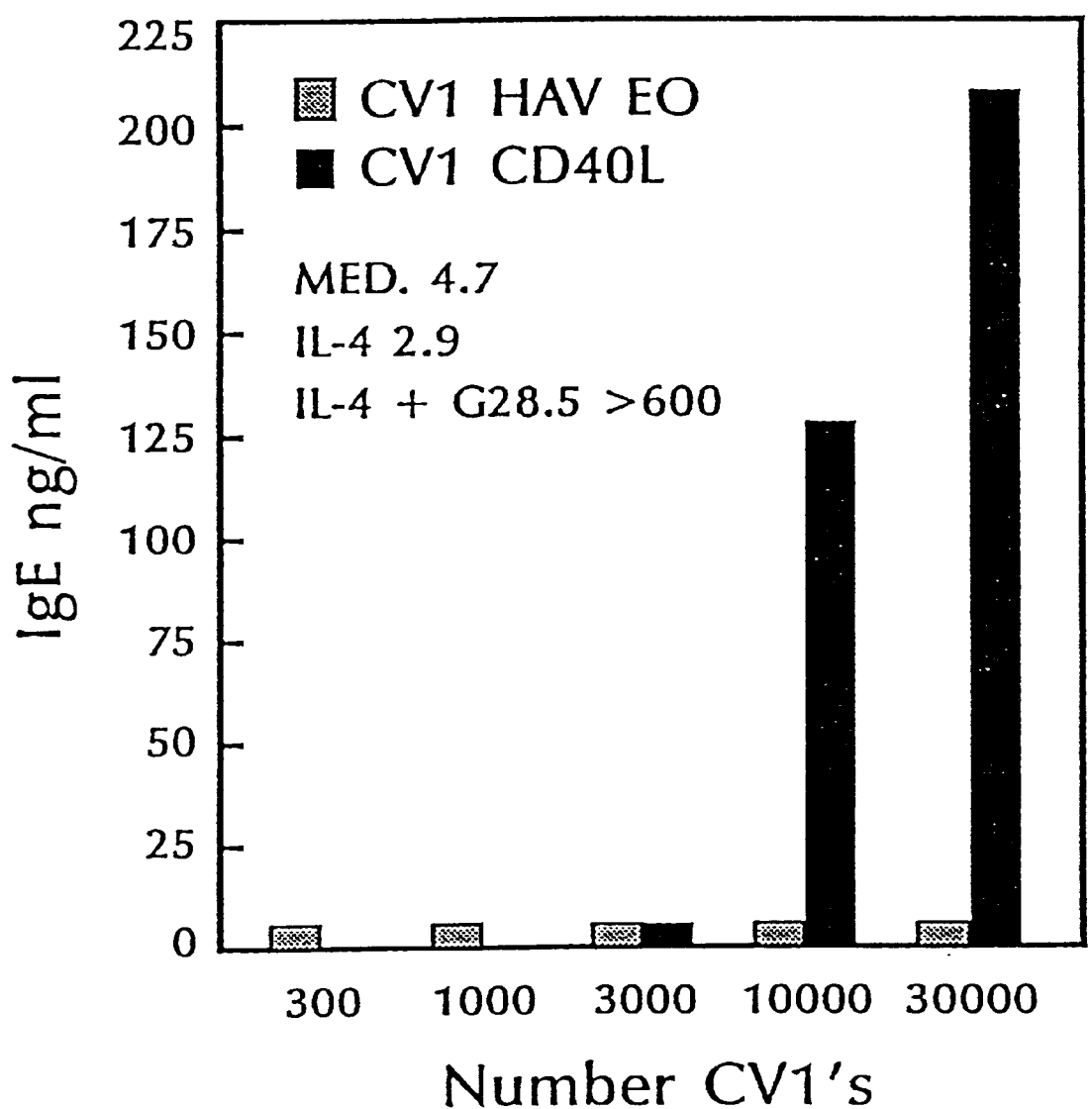
FIG. 6 illustrates that bound CD40-L augments IgE secretion.
Figure 7:
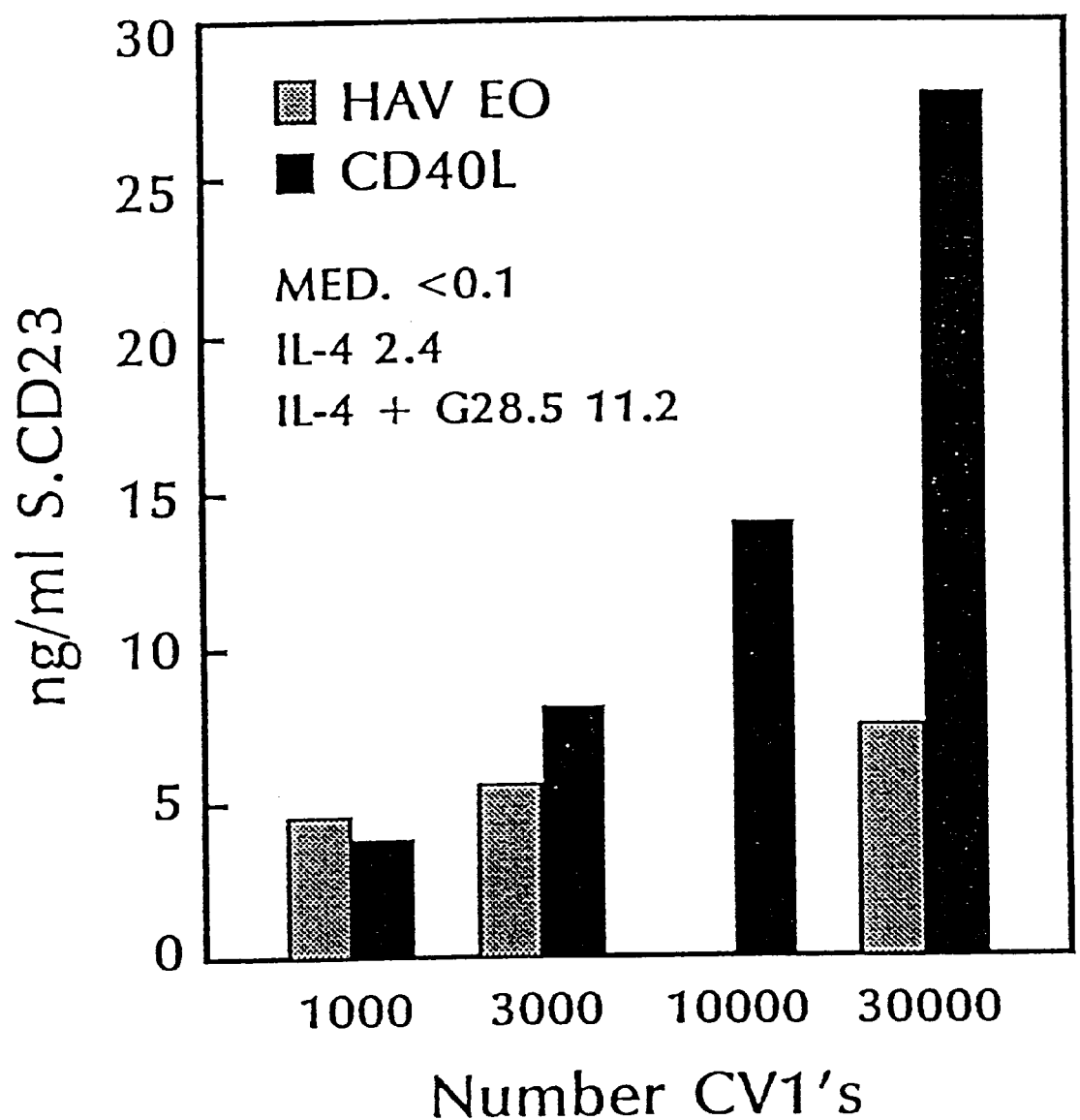
FIG. 7 illustrates that membrane-bound CD40-L stimulates CD23 shedding in the presence of IL-4.

FIG. 6 shows a comparison of IgE production in the supernatants (in ng/ml) for cultures of E⁻ cells and CV1 EBNA cells transfected with empty vector (HAVEO) or with CD40-L. No differences were noted with up to 3000 CV1 EBNA cells, however significant IgE production resulted with the addition of 10000 or 30000 CD40-L transfected CV 1 EBNA cells. As a comparison, when E⁻ cells were incubated with medium alone, 5 ng/ml IL-4 or 5 ng/ml IL-4 plus 500 ng/ml G28-5 antibody, IgE production was 4.7, 2.9 and >600 ng/ml, respectively. When CD23 shedding was measured in FIG. 7, 10000 and 30000 CV1 EBNA cells transfected with CD40-L showed increased CD23 shedding when compared to empty vector control CV1 EBNA cells. As a comparison, when E⁻ cells were incubated with medium alone, 5 ng/ml IL-4 or 5 ng/ml IL-4 plus 500 ng/ml G28–5 antibody, CD23 shedding was <0.1, 2.4 and 11.2 ng/ml, respectively. These data show that IgE production and CD23 shedding are both biological activities associated with membrane-bound CD40-L.

EXAMPLE 12

This example illustrates B cell proliferative activity, polyclonal immunoglobulin (Ig) production, antigen-specific antibody formation and various method for using membrane-bound and soluble CD40-L in clinical applications. We obtained murine splenic B cells according to procedures described in Grabstein et al. I supra, Maliszewski et al. I supra and Maliszewski et al. II supra. Briefly, the mixed culture of cells was purified by T cell depletion using T cell antiserum and complement, and adherent cell depletion by passage of Sephadex® G10 columns and by B cell positive selection by panning on petri dishes coated with goat anti-mouse IgM. Purified B cells were cultured in RPMI, fetal calf serum (5% for B cell proliferation assays and 20% for plaque forming cell assays or polyclonal antibody assays), 2-mercaptoethanol, antibiotics, amino acids and pyruvate. B cell proliferation was measured according to the assay described in Example 10 and in Grabstein et al. I supra, Maliszewski et al. I supra and Maliszewski et al. II supra. Antigen-specific antibody formation was measured by the procedure described in Grabstein et al., *J. Mol. Cell. Immunol.* 2:199, 1986 [Grabstein et al. II]. Briefly, antigen specific antibody formation used sheep red blood cells (SRBC) as antigen (0.03% v/v) in 2.0 ml cultures of 1×10⁶ murine B cells per culture. The B cell cultures were incubated for 5 days and plaque forming cells were determined by Jerne hemolytic plaque assay as described in Grabstein et al. II supra. Cell counts were determined in a coulter counter. Polyclonal Ig secretion was determined by isotype-specific ELISA assays in seven day cultures of 1×10⁶ B cells per 2.0 ml culture as described in Maliszewski et al. I supra and Maliszewski et al. II supra.

Figure 8:
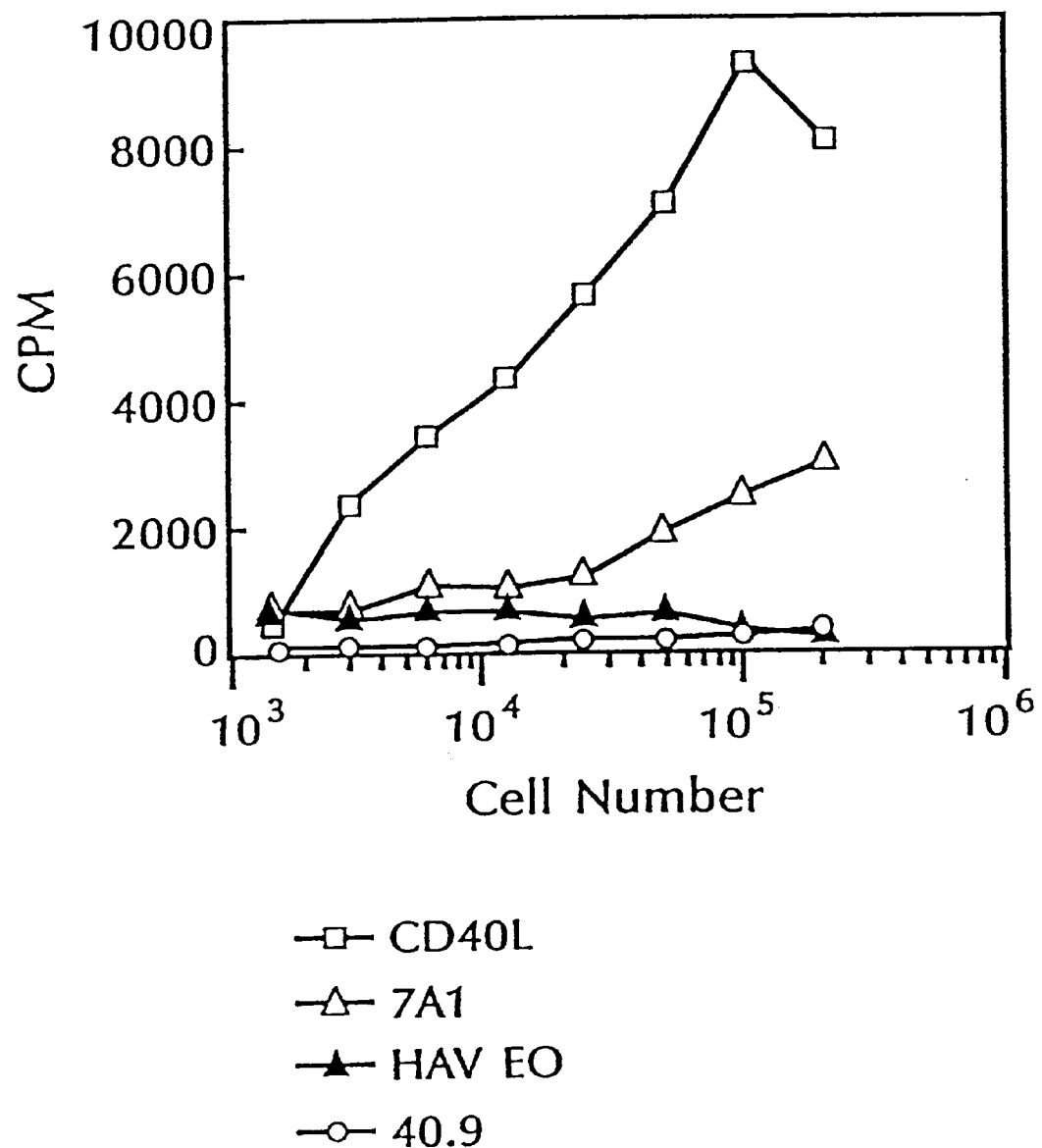
FIG. 8 illustrates proliferation of murine splenic B cells caused by membrane-bound murine CD40-L or 7A1 cells, which is a helper T cell clone.
Figure 10:
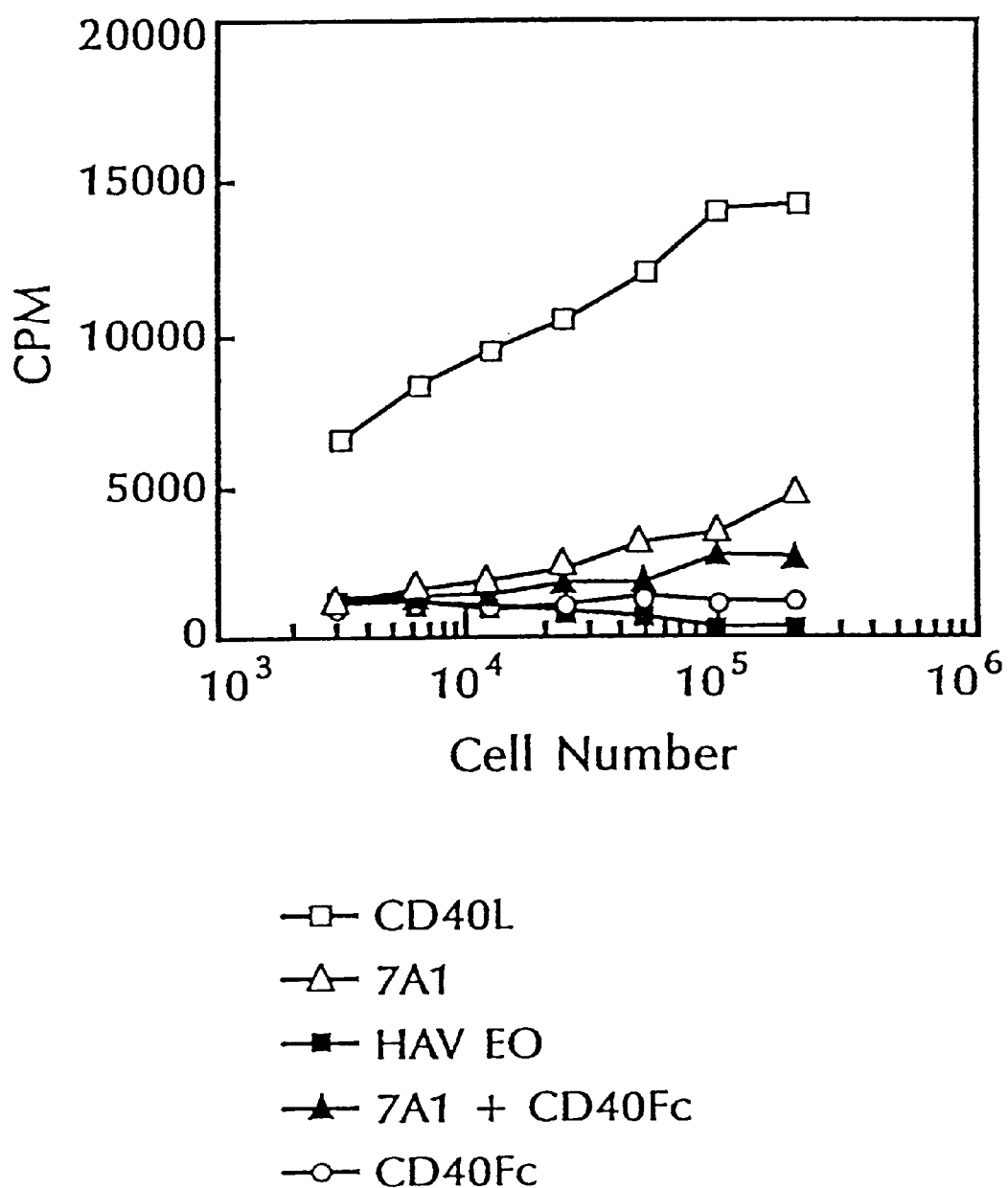
FIG. 10 illustrates a comparison of B cell proliferative activity of membrane-bound CD40-L and other cell types transfected with different cDNAs. Membrane-bound CD40-L showed significantly more B cell proliferative activity than a helper T cell clone or other control cells.
Figure 12:
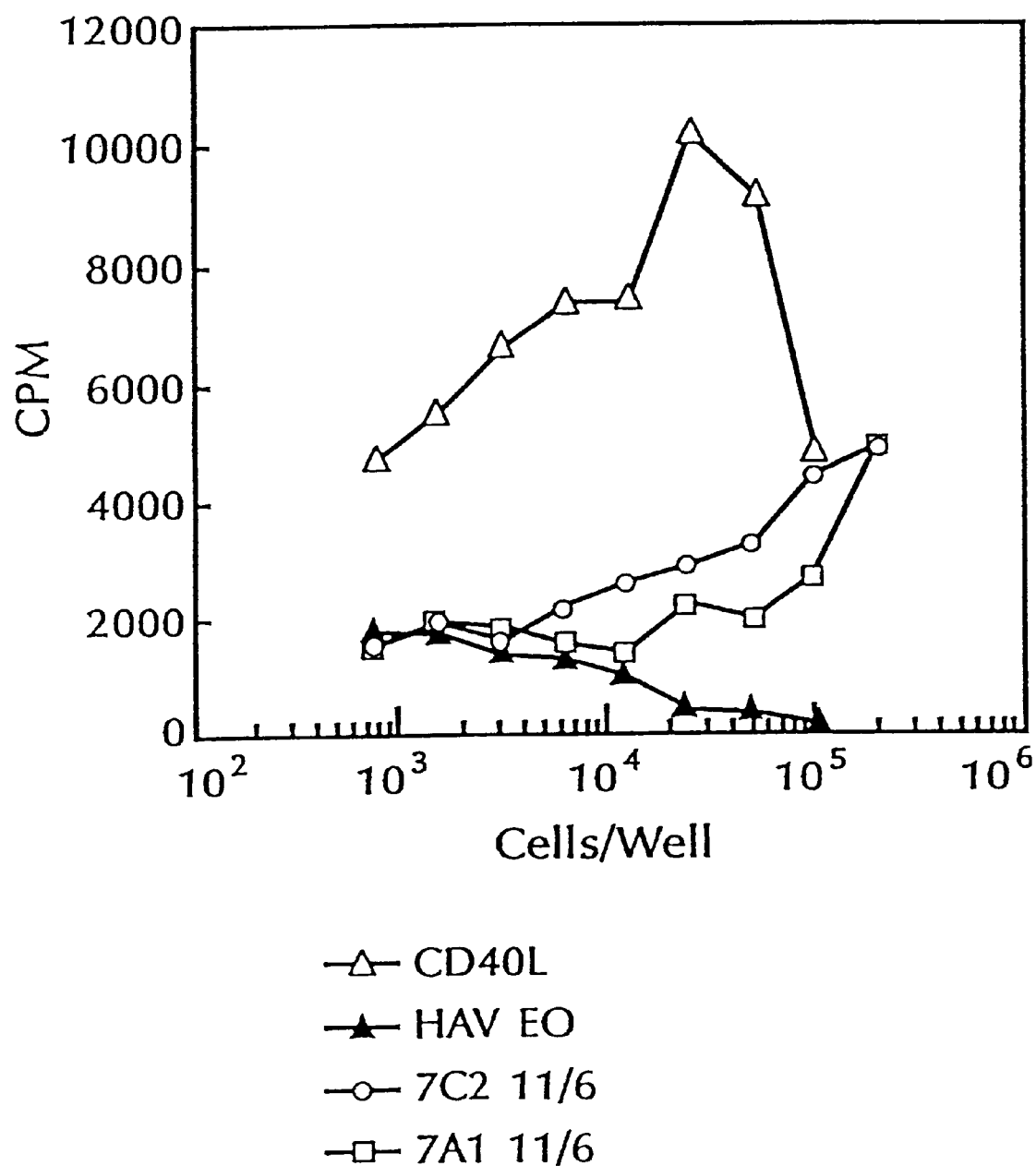
FIG. 12 illustrates a comparison of two helper T cell clones with cells expressing membrane-bound CD40-L for inducing murine B cell proliferation.

The results of B cell proliferation by CV1 EBNA cells transfected with CD40-L or empty vector or 7A1 cells (a T cell helper clone) are shown in FIGS. 8, 10 and 12. These data show that the greatest B cell proliferation was caused by CD40-L. T cell helper cells 7A1 and 7C2 had a minimal effect on B cell proliferation.

Figure 9:
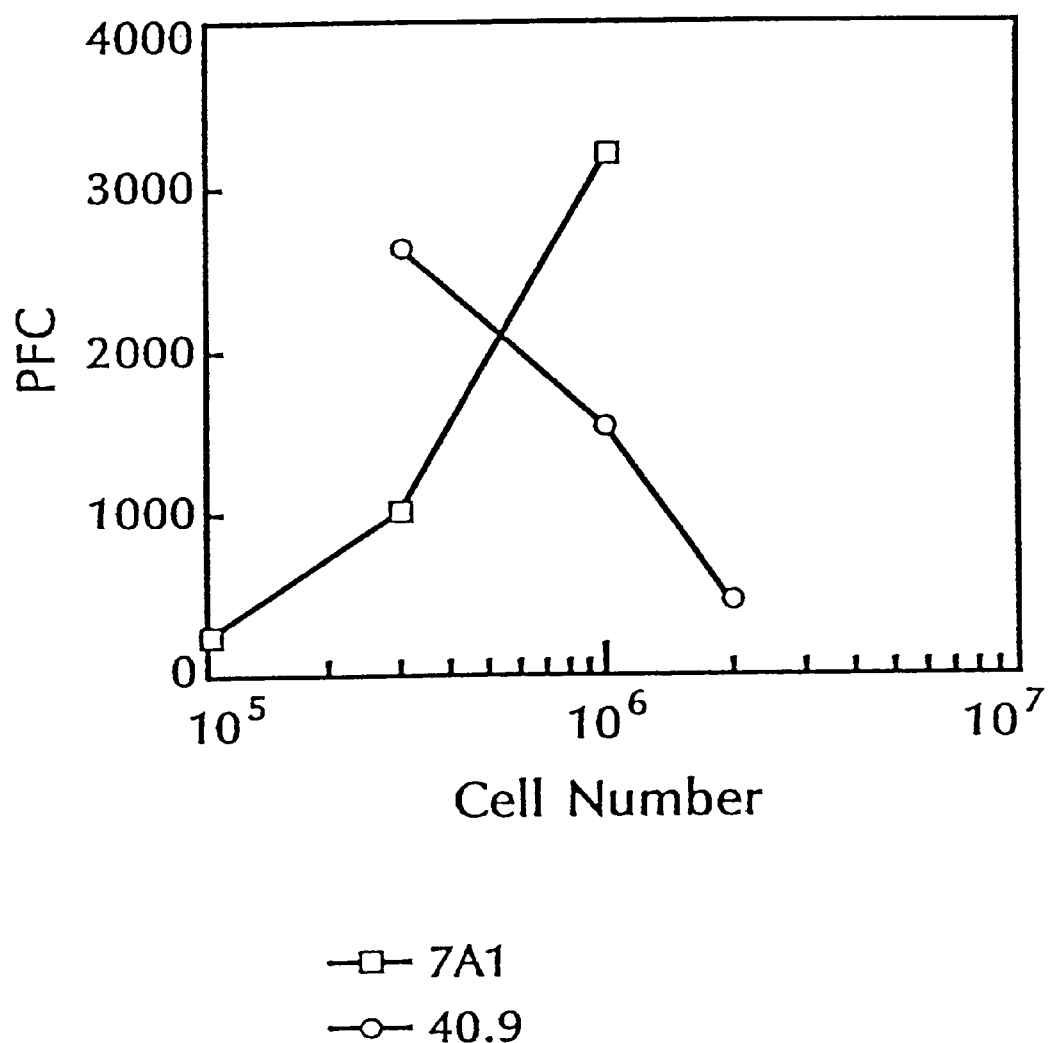
FIG. 9 illustrates a comparison of murine EL40.9 cells, a sorted cell line that was sorted on the basis of expression of murine CD40-L and T cells 7A1 for induction of an antigen-specific response indicated by plaque forming cells (PFC) by anti-sheep red blood cells (SCBC).
Figure 11:
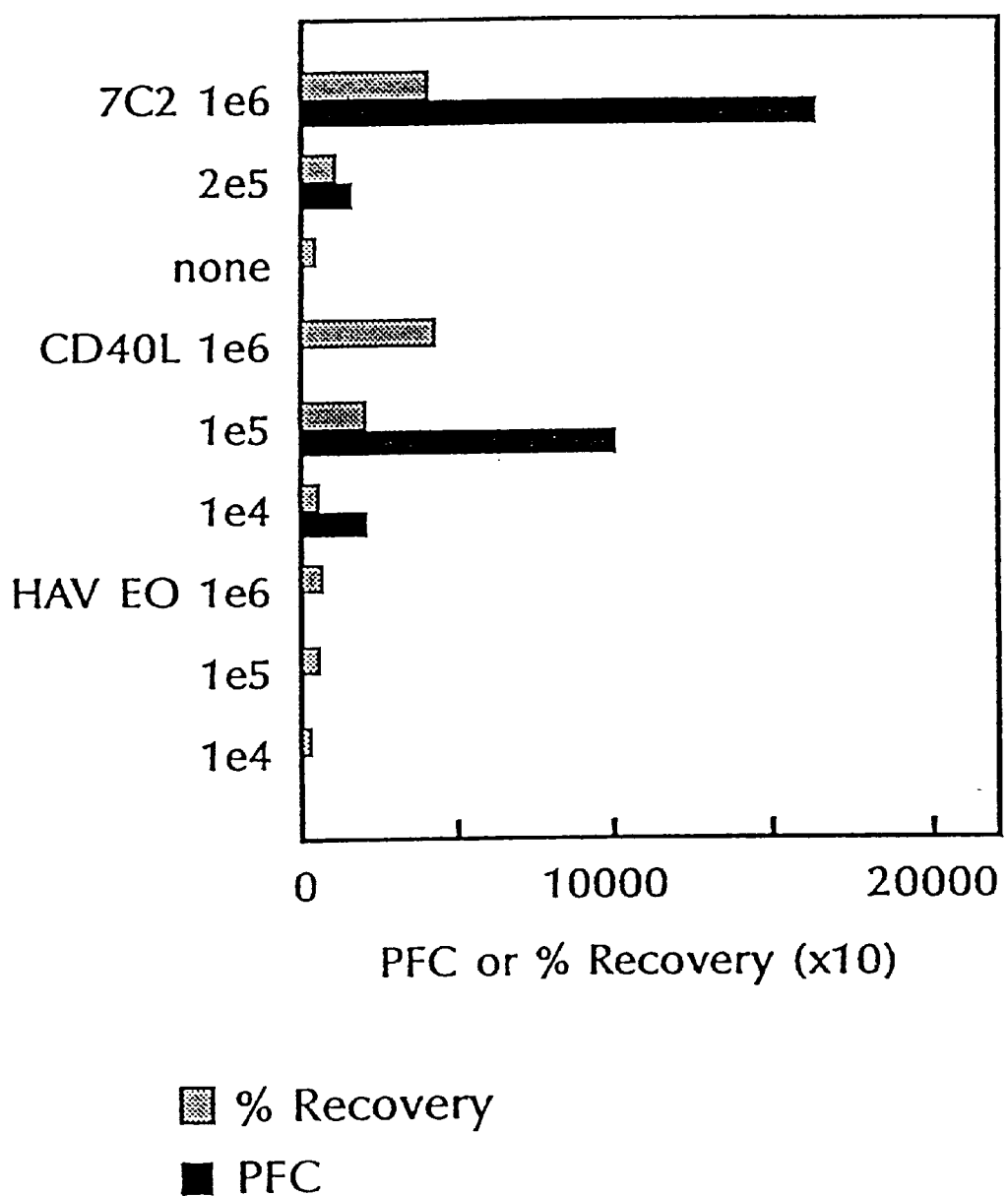
FIG. 11 illustrates that 7C2 cells (a helper T cell clone) and CV1 cells transfected with murine CD40-L cDNA induce anti SRBC plaque forming cells.
Figure 13A:
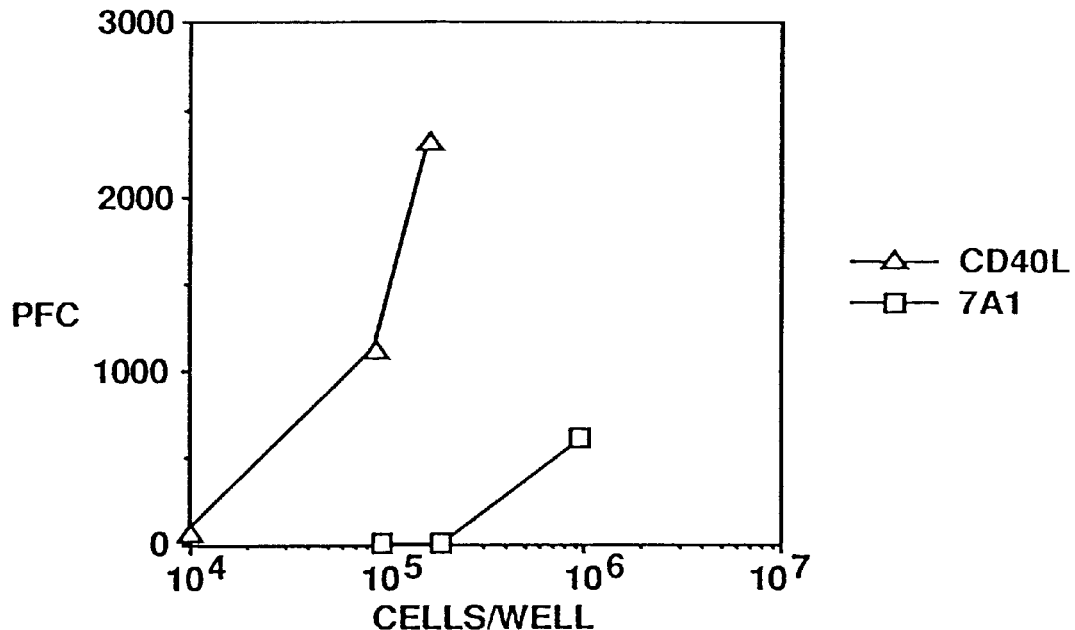
FIGS. 13A–13B illustrate induction of antigen-specific plaque forming cells by membrane-bound CD40-L and a helper T cell clone in the presence or absence of added interleukin-2 (IL-2).
Figure 13B:
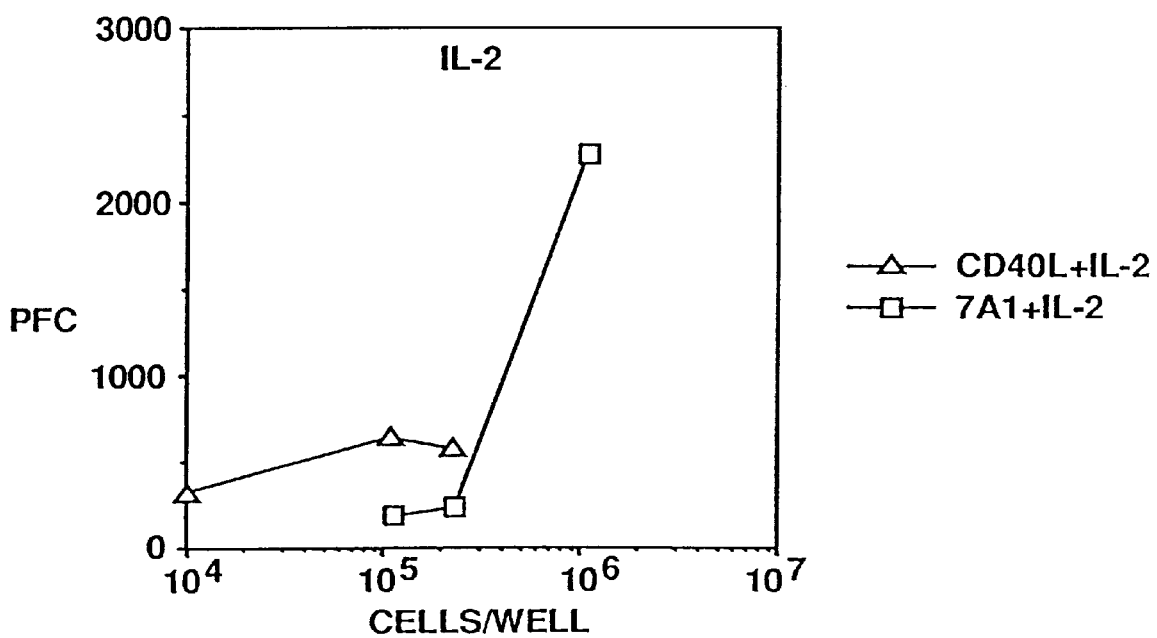

The effects of various cells upon antigen specific antibody formation are shown in FIGS. 9 and 11. FIG. 9 shows a comparison of plaque forming cells comparing T cell helper clone 7A1 and murine EL40.9 cells which secrete a soluble CD40-L. The EL40.9 cells seem to have an inhibitory effect upon antigen specific antibody formation. FIG. 11 shows PFC (plaque forming cells) for T cell helper cells 7C2 and CV 1 EBNA cells transfected with either empty vector or CD40-L. Both 7C2 cells and membrane-bound CD40-L stimulated antigen specific antibody formation (PFC). FIGS. 13A–13B compare antigen specific antibody formation of CD40-L and 7A 1 cells in the presence or absence of 10 ng/ml interleukin-2 (IL-2). IL-2 increased PFC for 7A 1 cells but did not increase PFC caused by membrane-bound CD40-L.

Polyclonal Ig production by murine B cells was compared for stimulation or inhibition with membrane-bound CD40-L, control CV1 EBNA cells and helper T cells 7A1 in the presence of cytokines IL-4 (10 ng/ml) and IL-5 (1:40 dilution of COS cell supernatants) or without added cytokines.The amount of IgA, IgG3, IgE, IgG2b, IgM and IgG1 are shown in Tables 3–8, respectively.

TABLE 3

IgA, ng/ml

| | # CELLS | MEDIA | +IL-4 + IL-5 |
|---|---|---|---|
| CD40-L | 2 × 10(5) | 666.275 ± 174.444 | 64.639 ± 51.780 |
| | 1 × 10(5) | 288.085 ± 20.773 | 291.831 ± 10.673 |
| | 1 × 10(4) | 53.750 ± 36.531 | 910.072 ± 62.713 |
| HAVEO | 2 × 10(5) | 0 | 628.190 ± 42.907 |
| | 1 × 10(5) | 0 | 477.755 ± 57.478 |
| | 1 × 10(4) | 0 | 295.640 ± 12.736 |
| 7A1 (2C11) | 1 × 10(6) | 0 | 2177.549 ± 377.052 |
| | 2 × 10(5) | 0 | 646.898 ± 86.325 |
| | 1 × 10(5) | 0 | 480.671 ± 40.011 |
| MEDIA | | 0 | 458.152 ± 77.258 |
| LPS | | 88.531 ± 31.248 | 132.336 ± 51.356 |

TABLE 4

IgG3, ng/ml

| | # CELLS | MEDIA | +IL-4 + IL-5 |
|---|---|---|---|
| CD40-L | 2 × 10(5) | 108.427 ± 14.359 | 0 |
| | 1 × 10(5) | 118.079 ± 8.021 | 46.535 ± 9.899 |
| | 1 × 10(4) | 127.591 ± 6.268 | 467.023 ± 78.276 |
| HAVEO | 2 × 10(5) | 0 | 29.773 ± 5.224 |
| | 1 × 10(5) | 11.205 ± 4.434 | 66.323 ± 8.673 |
| | 1 × 10(4) | 26.389 ± 10.221 | 34.671 ± 12.975 |
| 7A1 (2C11) | 1 × 10(6) | 33.420 ± 9.972 | 820.856 ± 39.442 |
| | 2 × 10(5) | 0 | 436.074 ± 59.332 |
| | 1 × 10(5) | 0 | 239.760 ± 45.978 |
| MEDIA | | 21.808 ± 7.107 | 64.773 ± 13.924 |
| LPS | | 816.697 ± 43.553 | 103.720 ± 11.883 |

TABLE 5

IgE, ng/ml

| | # CELLS | MEDIA | +IL-4 + IL-5 |
|---|---|---|---|
| CD40-L | 2 × 10(5) | 0 | 64.144 ± 4.979 |
| | 1 × 10(5) | 0 | 83.493 ± 9.093 |
| | 1 × 10(4) | 0 | 461.155 ± 60.514 |
| HAVEO | 2 × 10(5) | 0 | 0 |
| | 1 × 10(5) | 0 | 4.208 ± .527 |
| | 1 × 10(4) | 0 | 0 |
| 7A1 (2C11) | 1 × 10(6) | 0 | 208.091 ± 8.090 |
| | 2 × 10(5) | 0 | 32.530 ± 0.723 |
| | 1 × 10(5) | 0 | 15.889 ± 2.947 |
| MEDIA | | 0 | 12.602 ± 1.460 |
| LPS | | 0 | 408.355 ± 9.764 |

TABLE 6

IgG2b, ng/ml

| | # CELLS | MEDIA | +IL-4 + IL-5 |
|---|---|---|---|
| CD40-L | 2 × 10(5) | 0 | 0 |
| | 1 × 10(5) | 0 | 6.230 ± .285 |
| | 1 × 10(4) | 0 | 47.414 ± .241 |
| HAVEO | 2 × 10(5) | 0 | 7.001 ± 2.358 |
| | 1 × 10(5) | 0 | 6.230 ± 2.285 |
| | 1 × 10(4) | 0 | 9.620 ± 2.650 |
| 7A1 (2C11) | 1 × 10(6) | 0 | 189.343 ± 2.837 |
| | 2 × 10(5) | 0 | 22.431 ± 6.835 |
| | 1 × 10(5) | 0 | 7.207 ± 1.580 |

TABLE 6-continued

| | | IgG2b, ng/ml | |
|---|---|---|---|
| | # CELLS | MEDIA | +IL-4 + IL-5 |
| MEDIA | | 0 | 7.422 ± 1.602 |
| LPS | | 0 | 33.291 ± 3.183 |

TABLE 7

| | | IgM, μg/ml | |
|---|---|---|---|
| | # CELLS | MEDIA | +IL-4 + IL-5 |
| CD40-L | 2 × 10(5) | 1.805 ± 0.639 | 0.439 ± 0.184 |
| | 1 × 10(5) | 2.237 ± 0.583 | 5.878 ± 0.858 |
| | 1 × 10(4) | 2.293 ± 0.595 | 96.730 ± 13.009 |
| HAVEO | 2 × 10(5) | 0 | 10.890 ± 2.126 |
| | 1 × 10(5) | 0 | 13.303 ± 0.993 |
| | 1 × 10(4) | 0.624 ± 0.178 | 22.538 ± 2.304 |
| 7A1 (2C11) | 1 × 10(6) | 0.769 ± 0.124 | 104.857 ± 17.463 |
| | 2 × 10(5) | 0.142 ± 0.052 | 27.016 ± 1.706 |
| | 1 × 10(5) | 0.126 ± 0.048 | 13.070 ± 0.600 |
| MEDIA | | 0.231 ± 0.057 | 36.809 ± 2.860 |
| LPS | | 53.302 ± 9.668 | 41.974 ± 6.158 |

TABLE 8

| | | IgG1, ng/ml | |
|---|---|---|---|
| | # CELLS | MEDIA | +IL-4 + IL-5 |
| CD40-L | 2 × 10(5) | 0 | 130.185 ± 24.547 |
| | 1 × 10(5) | 0 | 310.588 ± 1.261 |
| | 1 × 10(4) | 0 | 270.727 ± 17.511 |
| HAVEO | 2 × 10(5) | 0 | 187.668 ± 57.730 |
| | 1 × 10(5) | 0 | 43.320 ± 49.770 |
| | 1 × 10(4) | 0 | 1363.464 ± 45.841 |
| 7A1 (2C11) | 1 × 10(6) | 0 | 145.652 ± 136.070 |
| | 2 × 10(5) | 0 | 365.563 ± 24.276 |
| | 1 × 10(5) | 0 | 449.475 ± 101.012 |
| MEDIA | | 0 | 133.660 ± 386.231 |
| LPS | | 0 | 246.213 ± 21.526 |

These data indicate that the interaction of CD40 with its ligand is the principal molecular interaction responsible for T cell contact dependent induction of B cell growth and differentiation to both antigen-specific antibody production and polyclonal Ig secretion. As such, these data suggest that antagonists of this interaction, by soluble CD40, CD40/Fc fusion protein and possibly soluble CD40-L (monomeric), will significantly interfere with development of antibody responses. Therefore clinical situations where CD40, CD40/Fc fusion proteins and soluble CD40-L are suitable include allergy, lupus, rheumatoid arthritis, insulin dependent diabetes mellitus, and any other diseases where autoimmune antibody or antigen/antibody complexes are responsible for clinical pathology of the disease. Moreover, membrane-bound CD40-L or oligomeric soluble CD40-L will be useful to stimulate B cell proliferation and antibody production. As such, these forms of CD40-L are most useful for vaccine adjuvants and as a stimulating agent for mAb secretion from hybridoma cells.

EXAMPLE 13

This example illustrates the effect of membrane-bound CD40-L upon proliferation of and IgE secretion from peripheral blood mononuclear cells (E−). E− cells were obtained according to the procedure described in Example 10 and incubated for 7 or 10 days in the presence of CV1 EBNA cells transfected with empty vector or mCD40-L cDNA. Additionally, CD40/Fc fusion protein (described in Example 1) or TNF Receptor/Fc fusion protein (described in WO 91/03553) was added to some of the preparations as indicated in FIG. 14. IgE secretion was measured according to the procedure described in Example 8 and B cell proliferation was measured according to the procedure described in Example 10.

Figure 14A:
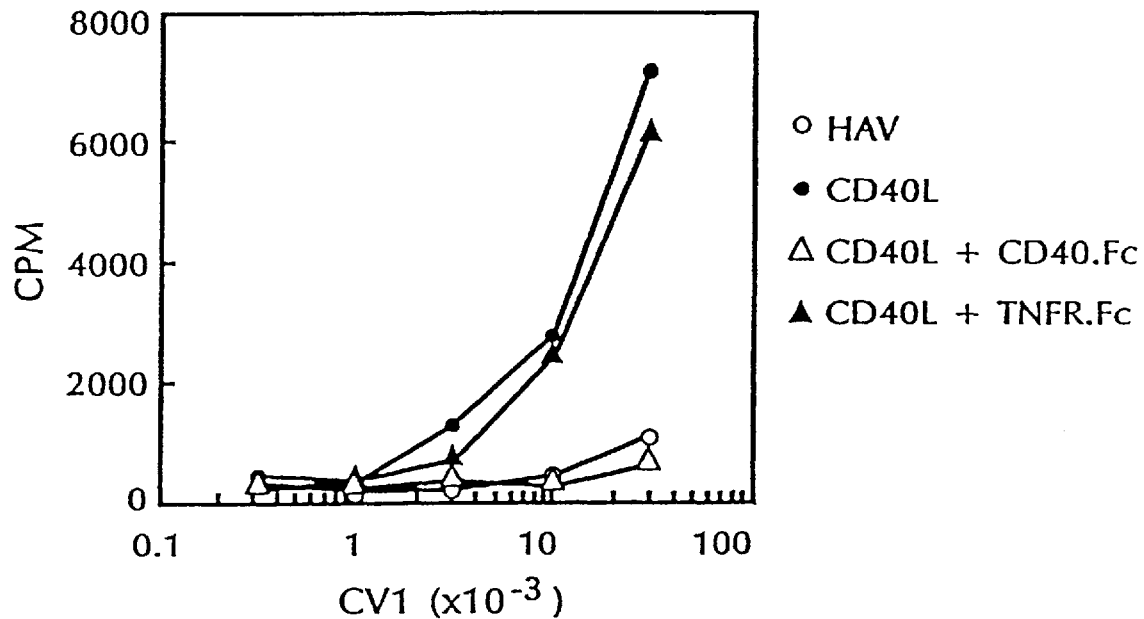
FIGS. 14A–14B show effects of membrane-bound CD40-L stimulating B cell proliferation and IgE secretion. The effects of membrane-bound CD40-L were inhibited by CD40 receptor but not by TNF receptor.
Figure 14B:
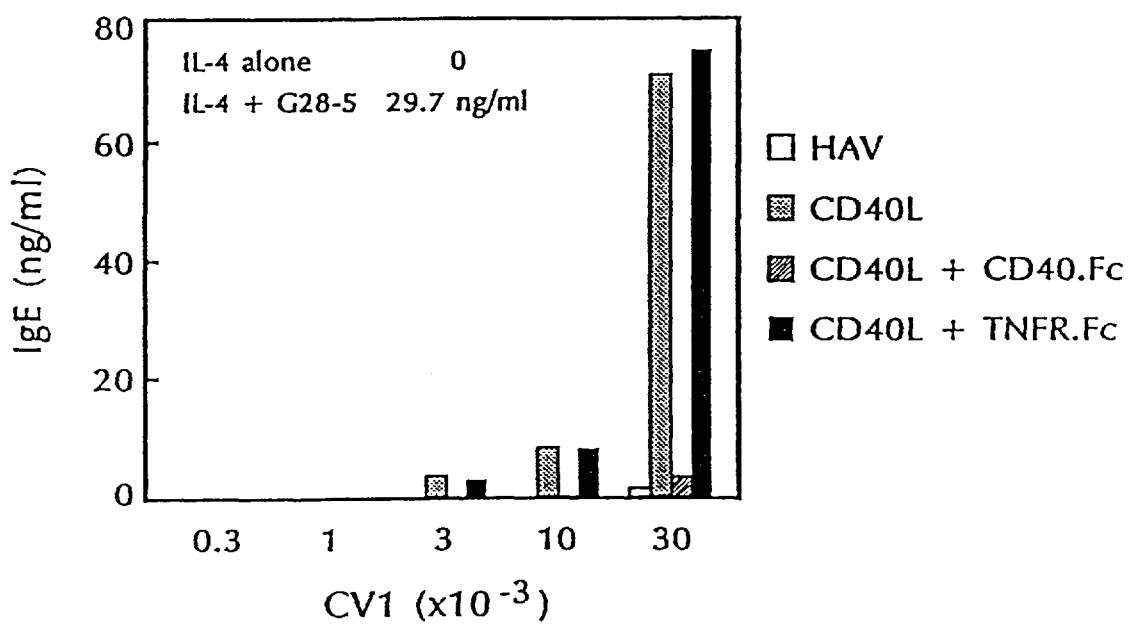
Figure 16A:
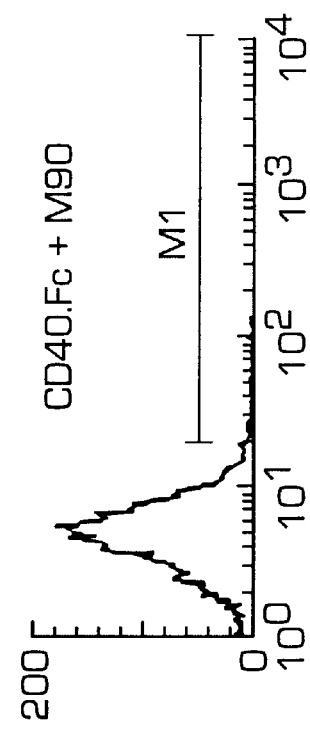
FIGS. 16A–16D illustrate the ability of monoclonal antibodies M90 and M91 to inhibit binding of 2 μg/ml CD40/Fc to peripheral blood T cells activated as described for FIG. 15.
Figure 16B:
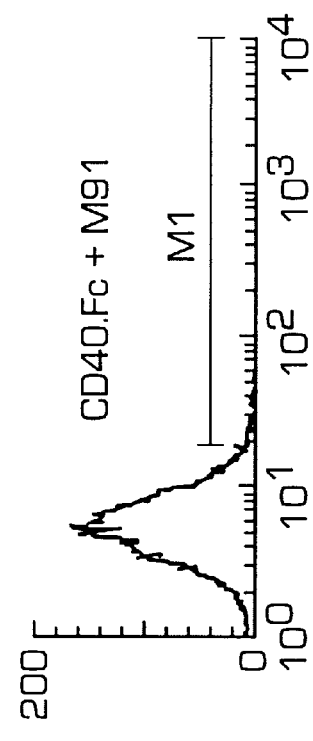
Figure 16C:
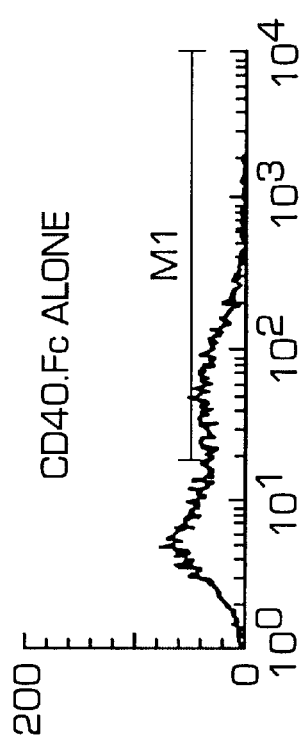
Figure 16D:
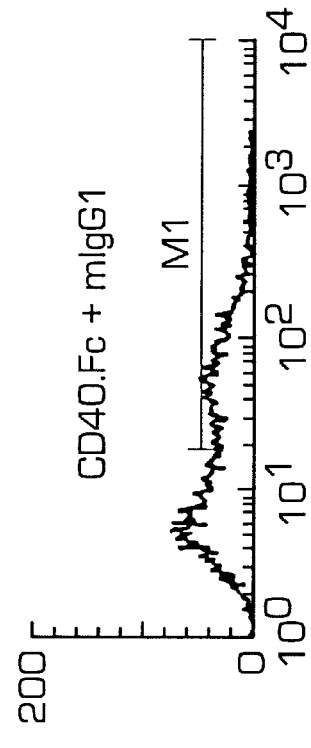

The results for B cell proliferation and IgE secretion are shown in FIGS. 14A–14B for five different concentrations of transfected CV1 EBNA cells. Both B cell proliferation and IgE secretion were increased in the presence of membrane-bound CD40-L. Addition of CD40/Fc fusion protein ablated both B cell proliferation and IgE secretion. The TNF Receptor/Fc fusion protein had no effect. As a comparison for IgE secretion, addition of IL-4 as a control agent (without transfected CV1 EBNA cells) produced no IgE in this assay and addition of IL-4 plus G28-5 anti-CD40 mAb resulted in 29.7 ng/ml IgE in this assay.

EXAMPLE 14

This example describes construction of a CD40-L/Fc DNA construct to express a soluble CD40-L/Fc fusion protein referred to as CD40-L/FC2 construct. DNA encoding CD40-L/FC2 comprises sequences encoding a leader (or signal) peptide, an eight amino acid hydrophilic sequence described by Hopp et al. (Hopp et al., *Bio/Technology* 6:1204,1988; referred to as FLAG™), a suitable Fc region of an immunoglobulin, a [Gly$_4$Ser]$_3$ repeat sequence (described in U.S. Pat. No. 5,073,627, which is incorporated by reference herein) or other suitable linker sequence, and the extracellular region of human CD40-L from amino acid 50 to amino acid 261 (SEQ ID NO:11). A pDC406 expression vector containing a leader sequence, FLAG™, and human IgG$_1$ Fc is prepared using conventional techniques of enzyme cutting and ligation of fragments encoding a leader sequence, FLAG™, and human IgG$_1$ Fc, and restricted with Nsi 1 and Not 1.

A PCR technique (Saiki et al., *Science* 239:487, 1988) was employed using 5' (upstream) and 3' (downstream) oligonucleotide primers to amplify the DNA sequences encoding CD40 extracellular ligand binding domain from a cloning vector containing human CD40-L (ATCC 68873; SEQ ID NO:11) to form a PCR fragment. The upstream oligonucleotide primer (SEQ ID NO:13) introduced a Nsi 1 site upstream from a linker sequence ([Gly$_4$Ser]$_3$SerSer), which was followed by 21 nucleotides of the extracellular domain of CD40-L (amino acids 51 through 57 of SEQ ID NO:11). A downstream oligonucleotide primer (SEQ ID NO:14) introduced a Not 1 site just downstream of the termination codon of the CD40-L. The PCR fragment was then ligated into the pDC406 expression vector containing a leader sequence, FLAG™, and human IgG$_1$ Fc. The nucleotide and predicted amino acid sequence of CD40-L/FC2 are presented in SEQ ID NO:15 and SEQ ID NO:16. The resultant DNA construct (CD40-L/FC2) was transfected into the monkey kidney cell line CV-1/EBNA (ATCC CRL 10478). The construct encoded a soluble CD40-L capable of binding CD40, as evidenced by binding observed in fluorescence-activated cell sorting (FACS) analysis using cells that express CD40.

Large scale cultures of human embryonic kidney 293 cells (ATCC CRL 1573) transfected with the construct encoding CD40-L/FC2 were grown to accumulate supernatant containing CD40-L/FC2. The 293 cell line, a permanent line of primary human embryonal kidney transformed by human adenovirus 5 DNA, permits expression of recombinant proteins ligated into the pCD406 vector. The CD40-L/FC2 fusion protein in supernatant fluid was purified by affinity purification. Briefly, culture supernatant containing the CD40-L/FC2 fusion protein was purified by filtering mammalian cell supernatants (e.g., in a 0.45µ filter) and applying filtrate to an antibody affinity column comprising biotinylated goat anti-human IgG (Jackson Immunoresearch Laboratories, Inc., Westgrove, Pa., USA) coupled to Streptavidin-agarose (Pierce Chemical, Rockford, Ill., USA) at 4° C., at a flow rate of approximately 60 to 80 ml/hr for a 1.5 cm×12.0 cm column. The column was washed with approximately 20 column volumes of PBS (phosphate buffered saline), until free protein could not be detected in wash buffer. Bound fusion protein was eluted from the column with 12.5 mM citrate buffer, 75 mM NaCl, pH 2.8, and brought to pH 7 with 500 mM Hepes buffer, pH 9.1. The purified, oligomeric CD40-L/FC2 peptide induced human B cell proliferation in the absence of any co-stimuli, and (in conjunction with the appropriate cytokine) resulted in the production of IgG, IgE, IgA and IgM, as described in Example 12 for membrane-bound CD40-L.

EXAMPLE 15

This example describes construction of a CD40-L DNA construct to express a soluble CD40-L fusion protein referred to as trimeric CD40-L. Trimeric CD40-L contains a leader sequence, a 33 amino acid sequence referred to as a "leucine zipper" or oligomerizing zipper (SEQ ID NO:17), and an eight amino acid hydrophilic sequence described by Hopp et al. (Hopp et al., *Bio/Technology* 6:1204,1988; referred to as FLAG™), followed by the extracellular region of human CD40-L from amino acid 50 to amino acid 261 (SEQ ID NO:11). The utility of the leader and the FLAG™ sequences have been described in the Detailed Description. The 33 amino acid sequence presented in SEQ ID NO:17 trimerizes spontaneously in solution. Fusion proteins comprising this 33 amino acid sequence are thus expected to form trimers or multimers spontaneously.

The construct is prepared by synthesizing oligonucleotides representing a leader sequence, the 33 amino acid sequence described above, and the FLAG™ sequence, then ligating the final product to a DNA fragment encoding amino acids 51 through 261 of SEQ ID NO:11, prepared as described in Example 14.

The resulting ligation product in expression vector pDC406 was transfected into the monkey kidney cell line CV-1/EBNA (ATCC CRL 10478). The pDC406 plasmid includes regulatory sequences derived from SV40, human immunodeficiency virus (HIV), and Epstein-Barr virus (EBV). The CV-1/EBNA cell line was derived by transfection of the CV-1 cell line with a gene encoding Epstein-Barr virus nuclear antigen-1 (EBNA-1) that constitutively expresses EBNA-1 driven from the human CMV intermediate-early enhancer/promoter. The EBNA-1 gene allows for episomal replication of expression vectors, such as pDC406, that contain the EBV origin of replication.

Once cells expressing the fusion construct are identified, large scale cultures of transfected cells are grown to accumulate supernatant from cells expressing trimeric CD40-L. The trimeric CD40-L fusion protein in supernatant fluid is purified by affinity purification substantially as described in U.S. Pat. No. 5,011,912. Silver-stained SDS gels of the eluted CD40-L fusion protein can be prepared to determine purity.

EXAMPLE 16

This example describes two solid-phase binding assays, the first of which, (a), can be used to asses the ability of trimeric CD40-L to bind CD40, and the second of which, (b), is used to detect the presence of CD40-L.

(a) Quantitative CD40-L ELISA

CD40/Fc is prepared and purified as described Example 1, and used to coat 96-well plates (Corning EasyWash ELISA plates, Corning, N.Y., USA). The plates are coated with 2.5 µg/well of CD40/Fc in PBS overnight at 4° C., and blocked with 1% non-fat milk in PBS for 1 hour at room temperature. Samples to be tested are diluted in 10% normal goat serum in PBS, and 50 µl is added per well. A titration of unknown samples is run in duplicate, and a titration of reference standard of CD40-L is run to generate a standard curve. The plates are incubated with the samples and controls for 45 minutes at room temperature, then washed four times with PBS. Second step reagent, rabbit anti-oligomerizing zipper, is added (50 µl/well, concentration approximately 2.5 µg/ml), and the plates are incubated at room temperature for 45 minutes. The plates are again washed as previously described, and goat F(ab')2 anti-rabbit IgG conjugated to horseradish peroxidase (Tago, Burlingame, Calif., USA) is added. Plates are incubated for 45 minutes at room temperature, washed as described, and the presence of CD40-L is detected by the addition of chromogen, tetramethyl benzidene (TMB; 100 µl/well) for 15 minutes at room temperature. The chromogenic reaction is stopped by the addition of 100 µl/well 2N $H_2SO_4$, and the $OD_{450}$-$OD_{562}$ of the wells determined. The quantity of trimeric CD40-L can be determined by comparing the OD values obtained with the unknown samples to the values generated for the standard curve. Values are expressed as the number of binding units per ml. A binding unit is roughly one ng of protein as estimated using a purified Fc fusion protein of the ligand as a standard. In this manner, the concentration and specific activity of several different batches of trimeric CD40-L purified as described in Example 19 have been determined.

(b) Qualitative Dot Blot

CD40-L trimer (1 µl of crude supernatant or column fractions) is adsorbed to dry BA85/21 nitrocellulose membranes (Schleicher and Schuell, Keene, N.H.) and allowed to dry. The membranes are incubated in tissue culture dishes for one hour in Tris (0.05 M) buffered saline (0.15 M) pH 7.5 containing 1% w/v BSA to block nonspecific binding sites. At the end of this time, the membranes are washed three times in PBS, and rabbit anti-oligomerizing zipper antibody is added at an approximate concentration of 10 µg/ml in PBS containing 1% BSA, following which the membranes are incubated for one hour at room temperature. The membranes are again washed as described, and a horseradish peroxidase (HRP)-labeled antibody (such as goat anti-rabbit Ig; Southern Biotech, Birmingham, Ala.) at an approximate dilution of 1:1000 in PBS containing 1% BSA is added. After incubating for one hour at room temperature, the membranes are washed and chromogen (i.e. 4-chloronaphthol reagent, Kirkegard and Perry, Gaithersburg, Md.) is added. Color is allowed to develop for ten minutes at room temperature, and the reaction is stopped by rinsing the membranes with water. The membranes are washed, and the presence of CD40-L is determined by analyzing for the presence of a blue-black color. This assay was used to determine the presence or absence of trimeric CD40-L in cell culture supernatant fluids and in purification column fractions. The assay further provides a semi-quantitative method of determining relative amounts of trimeric CD40-L by comparing the intensity of the color in unknown samples to the intensity of known quantities of controls.

EXAMPLE 17

This example describes construction of a human CD40-L DNA construct to express trimeric CD40-L in Chinese hamster ovary (CHO) cells. As described in Example 15, trimeric CD40-L contains a leader sequence, and a 33 amino acid sequence referred to as an oligomerizing zipper (SEQ ID NO:17), followed by the extracellular region of human CD40-L from amino acid 51 to amino acid 261 (SEQ ID NO:11). The construct was prepared by cutting the appropriate DNA from a plasmid containing human CD40-L (derived from the plasmid described in Example 15), and ligating the DNA into the expression vector pCAVDHFR. The resultant construct was referred to as CAV/DHFR-CD40LT. pCAVDHFR includes regulatory sequences derived from cytomegalovirus, SV40, and Adenovirus 2, along with the gene for dihydrofolate reductase (DHFR), and allows random integration of a desired gene into host cell chromosomes. Expression of DHFR enables the DHFR⁻ host cells to grow in media lacking glycine, hypoxanthine, and thymidine (GHT). A similar construct was also made for expression of murine CD40-L timer in CHO cells. In addition to the leader and oligomerizing zipper sequences, the murine construct also contained a sequence encoding the octapeptide referred to as Flag® (described previously) between the trimerization domain ("leucine zipper" or oligomerizing zipper) and the extracellular region of murine CD40-L. The nucleotide and amino acid sequence of the human and murine trimeric CD40-L-encoding DNAs are shown in SEQ ID NOs 20 and 22 respectively. Additional constructs can be prepared using standard methods. For example, vectors which incorporates dual promoters such as those described in U.S. Pat. No. 4,656,134, or vectors employing enhancer sequences such as those described in U.S. Pat. No. 4,937,190 or in Kaufman et al., *Nucl. Acids Res.* 19:4485, 1991, are also useful in preparing constructs for expression of CD40-L in CHO cells.

The resulting ligation product was transfected into CHO cells using either Lipofectin® Reagent or Lipofectamine™ Reagent (Gibco BRL, Gaithersburg, Md.). Both of these reagents are commercially available reagents used to form lipid-nucleic acid complexes (or liposomes) which, when applied to cultured cells, facilitate uptake of the nucleic acid into the cells. Cells which were transfected with the pCAVDHFR-CD40LT construct were selected in DMEM:F12 medium in the absence of GHT. Cells which were able to grow in the absence of GHT were tested for production of CD40-L using a solid phase binding assay as described in Example 16. Results indicated that in this transfection system, Lipofectamine™ Reagent gave higher rates of successful transfection.

Approximately 160 clones were screened and two positive clones were identified and expanded for further study. Cells were passaged in GHT-free DMEM:F12 medium, and monitored for stability by assessing production of trimeric CD40-L in the solid-phase binding assay described above. Based on these results, one clone was chosen which appeared to be stabley transfected with the CD40-L DNA, and which produced and secreted approximately 1 µg/106 cells/day of CD40-L trimer. Additional constructs comprising other vectors and all or a portion of the DNA sequences described in this example can be used to prepare additional stably transfected cell lines, substantially as described herein. For example, constructs encoding monomeric CD40-L similar to those described in Example 18 can be prepared, as can plasmids encoding any of the previously described constructs.

Once such stably transfected cells were identified, large scale cultures of transfected cells were grown to accumulate supernatant containing trimeric CD40-L. Suitable large-scale culture conditions include the use of bioreactors, as described below in Example 19. Similar procedures were followed to produce CHO cell lines that secreted a trimeric murine CD40-L at approximately 0.05 µg/$10^6$ cells/day. CHO cells stably transfected with either the human or murine CD40-L construct, having acquired a DHFR gene from the pCAVDHFR plasmid, are resistant to methotrexate. Methotrexate can be added to the culture medium to amplify the number of copies of the CD40-L trimer DNA in order to increase production of CD40-L trimer.

EXAMPLE 18

This example describes construction of a murine CD40-L DNA construct to express a soluble CD40-L protein referred to as monomeric CD40-L. Monomeric CD40-L contains a leader sequence, an eight amino acid sequence referred to as FLAG (amino acids 1–8 of SEQ ID NO:16), followed by the amino terminal truncated region of CD40-L encompassing the extracellular B-sheet forming region of the CD40 molecule from amino acid 119 to 260 of SEQ ID NO:1 (corresponding to amino acids 120 through 261 of human CD40-L, SEQ ID NO:12). A 68 amino acid stretch of the extracellular spacer region of the CD40-L molecule (amino acids 51–118 of SEQ ID NO:1) has been deleted in this construct, as has the transmembrane region (amino acids 1–50 of SEQ ID NO:1).

A PCR technique using 5' (upstream) and 3' (downstream) oligonucleotide primers was used to amplify the DNA sequences encoding the CD40-L truncated extracellular domain from a cloning vector containing murine CD40-L. The upstream oligonucleotide primer (ATATGAATTCGACTACAAAGATGACGATGATAAAC CTCAAATTGCAGCACACGTT; SEQ ID NO:18) appended an EcoRI site and the FLAG™ coding sequence upstream from CD40 nucleotide 355. The downstream oligonucleotide primer (CCTTCGCGGCCGCGTTCAGAGTTT GAGTAAGCCAA, SEQ ID NO:19) introduced a Not 1 site downstream of the authentic termination codon of the CD40L.

The PCR fragment was ligated into the multiple cloning site (EcoRI/NotI) of the baculovirus expression vector pAcGP67A (PharMingen, San Diego, Calif.) which contains the signal sequence for a glycoprotein of the *Autographica californica* nuclear polyhedrosis virus under the control of the viral polyhedrin promoter. The resultant DNA construct was cotransfected with *Autographica californica* viral DNA into *Spodoptera frugiperda* cells (SF21), and the resultant recombinant virus was plaque purified.

The CD40-L protein encoded by this construct was purified by FLAG™ affinity chromatography from serum free culture of recombinant virus infected cells. Purified protein had an apparent molecular weight of 21 Kd when run in a reducing PAGE and stained with Coomasie Blue. Both crude infected cell supernatants containing CD40-L and affinity purified CD40-L protein showed receptor binding activity in a solid phase assay utilizing the CD40Fc recombinant receptor. Mock infected controls had no activity.

A similar CD40-L construct was made without an amino terminal FLAG™ sequence. This construct utilized an existing Bam HI site at nucleotide 351 in the CD40-L sequence and the downstream PCR oligonucleotide primer described above (SEQ ID NO:19). After amplification of the CD40 sequence with a 5' upstream oligonucleotide homologous to CD40-L nucleotides 324–346, and the downstream primer which introduced a Not I site, the PCR product was cut with Bam HI and Not I and ligated into pAcGP67A cut with Bam HI and NotI. This construct was cotransfected into SF21 cells along with viral DNA as previously described, and recombinant virus was plaque purified, expanded and used to infect insect cells to produce serum free conditioned supernatants. CD40-L was detectable in these crude supernatants by both CD40Fc receptor binding assay and by detection of an 18 Kd band on a Coomassie Blue-stained PAGE. Similar copnstructs were also prepared for human CD40-L.

EXAMPLE 19

This example describes purification of trimeric murine CD40L from supernatant fluid from transfected CHO cells. A CHO cell line expressing muCD40LT was maintained in suspension in spinner-flask cultures. For production, the cells were centrifuged and resuspended into a controlled 3 liter bioreactor in serum-free medium. Oxygen, agitation and pH were controlled for at 40% dissolved $O_2$ (relative to air saturation), 150 RPM and 7.2, respectively. The culture was harvested after nine days. A total volume of approximately 160 ml of supernatant fluid from the bioreactor was dialyzed overnight at 4° C. against 4 L of 20 mM Tris pH 7.5 buffer containing 150 mM NaCl, and then adjusted to 1 M $(NH_4)_2SO_4$ by the addition of solid $(NH_4)_2SO_4$. Dialysis accomplished the removal of low-molecular weight contaminants; other techniques will also be useful for this purpose, for example, constant volume diafiltration.

The dialyzed supernatant was initially purified by hydrophobic interaction chromatography. The supernatant was applied to a 1.6×13 cm (26 ml) Phenyl Sepharose® CL-4B column (Pharmacia, Uppsala, Sweden) previously equilibrated with 10 mM Tris pH 8.0/1M $(NH_4)_2SO_4$ (Buffer A). The column was washed with 60 mL Buffer A, and bound proteins were eluted at 2 mL/min with a decreasing $(NH_4)_2SO_4$ gradient using Buffer A and 10 mM Tris pH 8.0 (Buffer B). The gradient conditions were 0 to 60% Buffer B in 20 ml, hold at 60% Buffer B for 60 ml, 60 to 100% Buffer B in 20 ml, and hold at 100% Buffer B for 60 ml. A total of 53 3 ml fractions were collected during the elution process. The elution of protein was monitored by absorbance at 280 nm. The presence of active trimeric CD40L was determined by an ELISA as described in Example 16. A peak of activity eluted in fractions 8–20. In a subsequent purification run, highsub and lowsub Phenyl Sepharose® 6 Fast Flow (Pharmacia, Uppsala, Sweden) were used for the hydrophobic interaction step; the highsub Phenyl Sepharose® column was found to give equivalent results to those obtained with Phenyl Sepharose® CL-4B.

Peak fractions from the Phenyl Sepharose® CL-4B column were pooled, and glycerol was added to a final concentration of 10% (v/v). The pool was then concentrated to a volume of approximately 4.5 ml using Amicon Centriprep 10 concentrators with a 10,000 molecular weight cutoff, and chromatographed over a sizing column (Superdex 200 26/60; Pharmacia, Uppsala, Sweden; 2.6×60 cm). The concentrated pool was loaded, and eluted with 20 mM Tris pH 7.5/150 mM NaCl/10% glycerol (v/v), at a flow rate of 2.0 ml/min. Protein elution was monitored at 280 nm, and eighty 2 ml fractions were collected. Activity was determined as described above; a peak of activity eluted in fractions 36–48. Purity was evaluated by sodium dodecyl sulfate polyacrylamide gel electrophoresis (SDS-PAGE) under reducing conditions on 10% acrylamide gels (Novex). The gels were stained by silver stain substantially as described by Oakley et al., *Anal. Biochem.* 105:361 (1980). The silver-stained gels showed several proteins present in the fractions.

Fractions from the peak of activity from the Superdex 200 column were pooled, concentrated as described above to approximately 2.0 ml, diluted 1:2 in 20 mM Bis Tris Propane pH 6.5/10% glycerol (v/v), and further purified by anion exchange chromatography. The concentrated pooled material was applied at 1 mL/min to a MONO Q® column (Pharmacia, 0.5×5 cm) equilibrated with 20 mM Bis Tris Propane pH 6.5/10% glycerol (v/v) (Buffer A). The column was washed with 16 mL Buffer A and eluted with a salt gradient using Buffer A and 20 mM Bis Tris Propane pH 6.5/500 mM NaCl/10% glycerol (v/v) (Buffer B). The column elution conditions were 0 to 60% Buffer B in 20 ml, 60 to 100% Buffer B in 1.0 ml, and hold at 100% Buffer B for 10 ml. A total of 30 1 ml fractions were collected during the elution process. Activity and $A_{280}$ were monitored as described previously. A peak of activity eluted in fractions 15–23. The fractions were evaluated by SDS-PAGE and silver stain as described above. Fractions 20–22 were estimated to contain about 80% trimeric murine CD40L, and were pooled. In a subsequent run, a HIGH PERFORMANCE Q® resin (Pharmacia, Uppsala, Sweden) was used and found to give equivalent results. Table 9 below summarizes the results of the procedure used to purify trimeric murine CD40L.

TABLE 9

Purification of Trimeric Murine CD40-L

| Step | Volume (ml) | Total # Binding Units | Total Protein (mg) | Specific Activity* |
|---|---|---|---|---|
| 1. Supernatant fluid | 160 | $5.2 \times 10^6$ | 280 | $1.9 \times 10^4$ |
| 2. Dialyzed Supernatant | 169 | $6.4 \times 10^6$ | 106 | $6.0 \times 10^4$ |
| 3. Phenyl Sepharose ® pool | 37 | $2.3 \times 10^6$ | 8.0 | $2.9 \times 10^5$ |
| 4. SUPERDEX ® 200 pool | 24 | $2.3 \times 10^6$ | 1.4 | $1.6 \times 10^5$ |
| 5. MONO Q ® pool | 7 | $6.4 \times 10^5$ | 0.91 | $7.0 \times 10^5$ |

*Specific activity is defined as the number of binding units of CD40-L per mg protein. One binding unit of CD40L is defined as 0.5 ng of purified CD40-L, as determined in a quantitative, enzyme-based binding assay. Protein concentration was determined using the BCA Protein Assay Reagent (Pierce); bovine serum albumen was used as the standard.

EXAMPLE 20

This example describes the effect of CD40-L trimer (CD40LT) on primary antibody response to a T-dependent antigen. On day 0, 6 BALB/c mice were injected subcutaneoulsy with 200 µl of a suspension containing 10 µg of ovalbumen (OVA), in the presence of Freund's incomplete adjuvant (IFA). Three of the mice also received 200 µl of PBS containing a total of 1.5 µg CD40LT, while the remaining mice received a similar amount of a control protein (murine serum immunoglobulin; msIgG). The mice were again treated with 1.5 µg of CD40LT or control protein on day 6.

Serum samples were taken on days 7 and 14, and analyzed for elevated levels of antigen-specific IgG or IgM using an OVA ELISA. Briefly, 96-well plates were coated with 10 µg/well of OVA at 4° C. overnight, then blocked with non-fat milk. Serial two-fold dilutions of serum samples were prepared in PBS containing 10% normal goat serum, and 50 µl of each dilution was added to a well. Plates were incubated for one hour at room temperature, and washed with PBS. The presence of antigen-specific IgG or IgM was detected using goat anti mouse IgG or IgM (Southern Biotech) conjugated to horseradish peroxidase for one hour at room temperature, followed by a wash step and the addition of substrate (TMB, Kirkegard and Perry). Color development proceeded for ten minutes at room temperature, and was stopped by the addition of $H_2SO_4$. The maximal dilution of serum dilution containing IgG or IgM anti-OVA activity was determined by plotting the $OD_{450}$–$OD_{562}$ of the diluted mouse sera, and comparing the OD values obtained with OD values from pre-immune sera. Results are presented in Table 10 below.

TABLE 10

Effect of Trimeric Murine CD40-L on Primary Immune Response

| Treatment: | Total IgG[a] Endpoint titer (est[c]) | | Relative Ab levels[b] % over non-immune$_{max}$ | |
|---|---|---|---|---|
| | Day 7 | Day 14 | Day 7 | Day 14 |
| msIgG (#1) | <50 | 400 | <25 | 216 |
| msIgG (#2) | <50 | >400 | <25 | 285 |
| msIgG (#3) | <50 | 200 | <25 | 212 |
| CD40LT (#1) | 400 | 200 | 279 | 240 |
| CD40LT (#2) | 800 | >400 | 379 | 339 |
| CD40LT (#3) | 200 | 200 | 178 | 228 |

[a]: Antigen-specific IgM titers were low at both day 7 and day 14 in both groups.
[b]: ($OD_{max}$ of treated mouse/$OD_{max}$ of pre-immune control) × 100
[c]: Estimated.

The mice treated with CD40LT exhibited greater levels of OVA-specific IgG as compared to control mice, indicating that CD40LT was able to boost a primary immune response to a T-dependent antigen, both enhancing the level of antigen-specific antibody and isotype switching from IgM to IgG.

A second experiment was carried out using different lots of reagents and varying the concentrations of the CD40-L. A significant difference between the control mice and the mice treated with CD40 ligand was not observed at day 7, however, CD40-L did enhance the day 14 response. Additional experiments to address the use of CD40-L will include an analysis of different antigens as well as the use of different adjuvants and delivery systems.

EXAMPLE 21

This example illustrates the activities of monoclonal antibodies to CD40-L. Supernatants from 264 hybridomas prepared as described in Example 7 were screened for anti-CD40-L activity by FACS analysis using human peripheral blood T cells stimulated with PMA and ionomycin for 16 hours. Under these conditions, four of the tested hybridoma supernatants gave a FACS profile similar to that obtained with CD40/Fc; an exemplary FACS profile is shown in FIGS. 15A–15D. Six additional hybridoma supernatants gave weak positive results, and the remainder did not appear to bind activated T cells.

The ten hybridoma supernatants that gave positive or weak positive results were then tested in another FACS assay using CV-1/EBNA cells transfected with vector alone or with vector encoding human CD40-L, as well as being reevaluated against activated T cells. Several of the supernatants appeared to be non-specifically reactive, however, three supernatants specifically stained CD40-L expressing CV-1/EBNA cells, and were selected for cloning and further evaluation.

Figure 17:
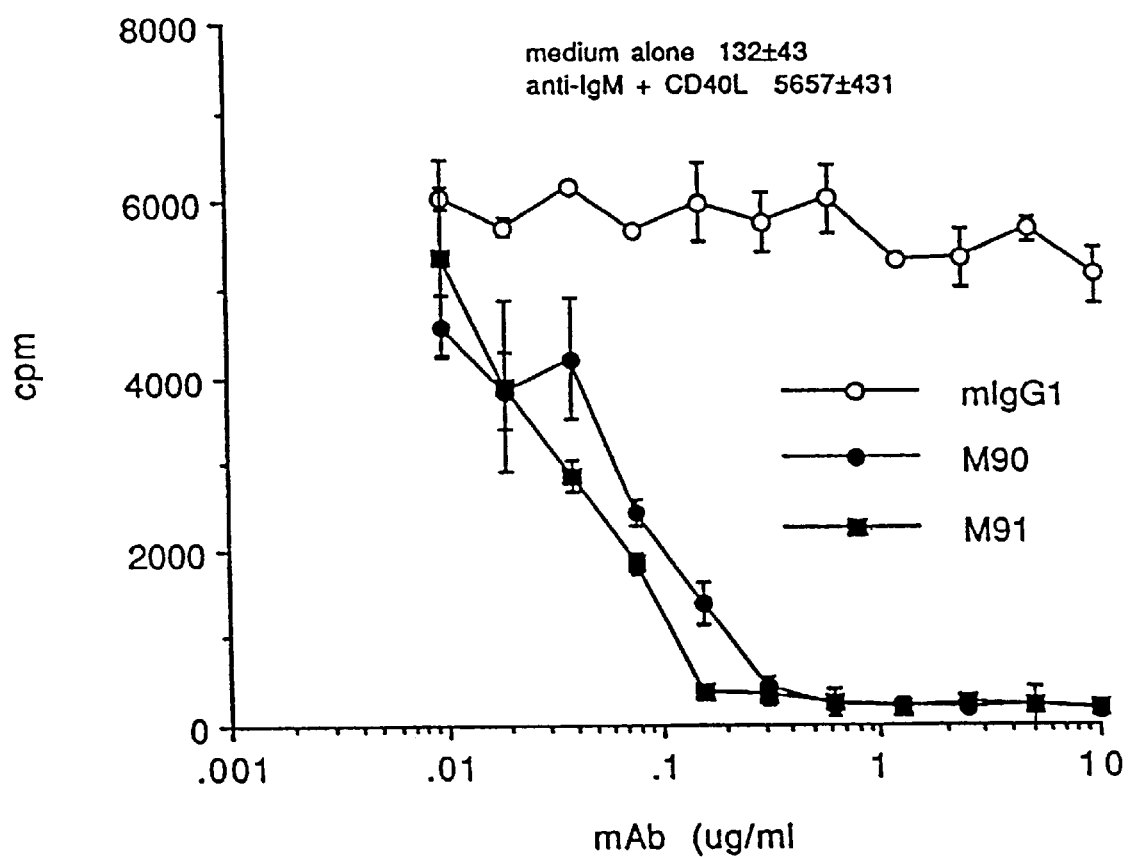
FIG. 17 demonstrates the ability of anti-CD40-L monoclonal antibodies to bind trimeric CD40-L and inhibit the ability of CD40-L to induce B cell proliferation. Purified tonsil B cells were cultured with 5 μg/ml immobilized rabbit anti-human IgM and recombinant soluble human CD40-L. M90, M91 or an isotype control antibody were titrated into the cultures; incorporation of tritiated thymidine was used as a measure of proliferation.

The three anti-CD40-L secreting clones were expanded and supernatant fluids were evaluated for ability to bind CD40-L and inhibit (or block) binding of CD40-L to CD40. In a FACS assay using activated human T cells (prepared as described above), the monoclonal antibody secreted by three of the clones blocked the binding of CD40/Fc to CD40-L, whereas the fourth did not. Representative results are shown in FIGS. 16A–16D. Several of the monoclonal antibodies were also tested for the ability to inhibit B cell proliferation in an assay substantially as described in Example 13 herein, using CD40-L-containing supernatant fluid from COS cells transfected with a vector encoding CD40-L. As shown in FIG. 17, the monoclonal antibodies that were able to inhibit binding of CD40/Fc to CD40-L by FACS analysis also inhibited the ability of trimeric CD40-L plus anti-IgM to induce proliferation of peripheral blood B cells.

The monoclonal antibodies were also evaluated in a solid phase ELISA in which plates were coated with a rabbit antibody to the oligomerizing zipper domain of trimeric CD40-L. Trimeric CD40-L was then added to the plates, followed by (after appropriate incubation and washing steps) supernatant fluids containing the monoclonal antibodies. The presence of antibodies to the CD40-L trimer was detected using enzyme labeled anti-mouse immunoglobulin followed by the appropriate substrate. The three monoclonal antibodies that inhibited the binding of CD40/c to CD40-L expressing T cells by FACS also bound to the CD40-L trimer used in the solid phase ELISA. Two of the hybridoma cell lines (designated M90 and M91) were selected for further expansion. These hybridoma cell have been deposited with the American Type Culture Collection, 10801 University Boulevard, Manassas, Va. 20110-2209 on Feb. 23, 1996, and given accession number HB 12055 (M90) and HB 12056 (M91).

EXAMPLE 22

This example illustrates the binding affinities of several different CD40-L constructs. Affinity experiments were conducted by biospecific interaction analysis (BIA) using a biosensor, an instrument that combines a biological recognition mechanism with a sensing device or transducer. An exemplary biosensor is BIAcore™, from Pharmacia Biosensor AB (Uppsala, Sweden; see Fägerstam L. G., *Techniques in Protein Chemistry* II, ed. J. J. Villafranca, Acad. Press, New York, 1991). BIAcore™ uses the optical phenomenon surface plasmon resonance (Kretschmann and Raether, *Z. Naturforschung, Teil.* A 23:2135, 1968) to monitor the interaction of two biological molecules. Molecule pairs having affinity constants in the range $10^5$ to $10^{10}$ $M^{-1}$, and association rate constants in the range of $10^3$ to $10^6$ $M^{-1}s^{-1}$, are suitable for characterization with BIAcore™.

Figure 18:
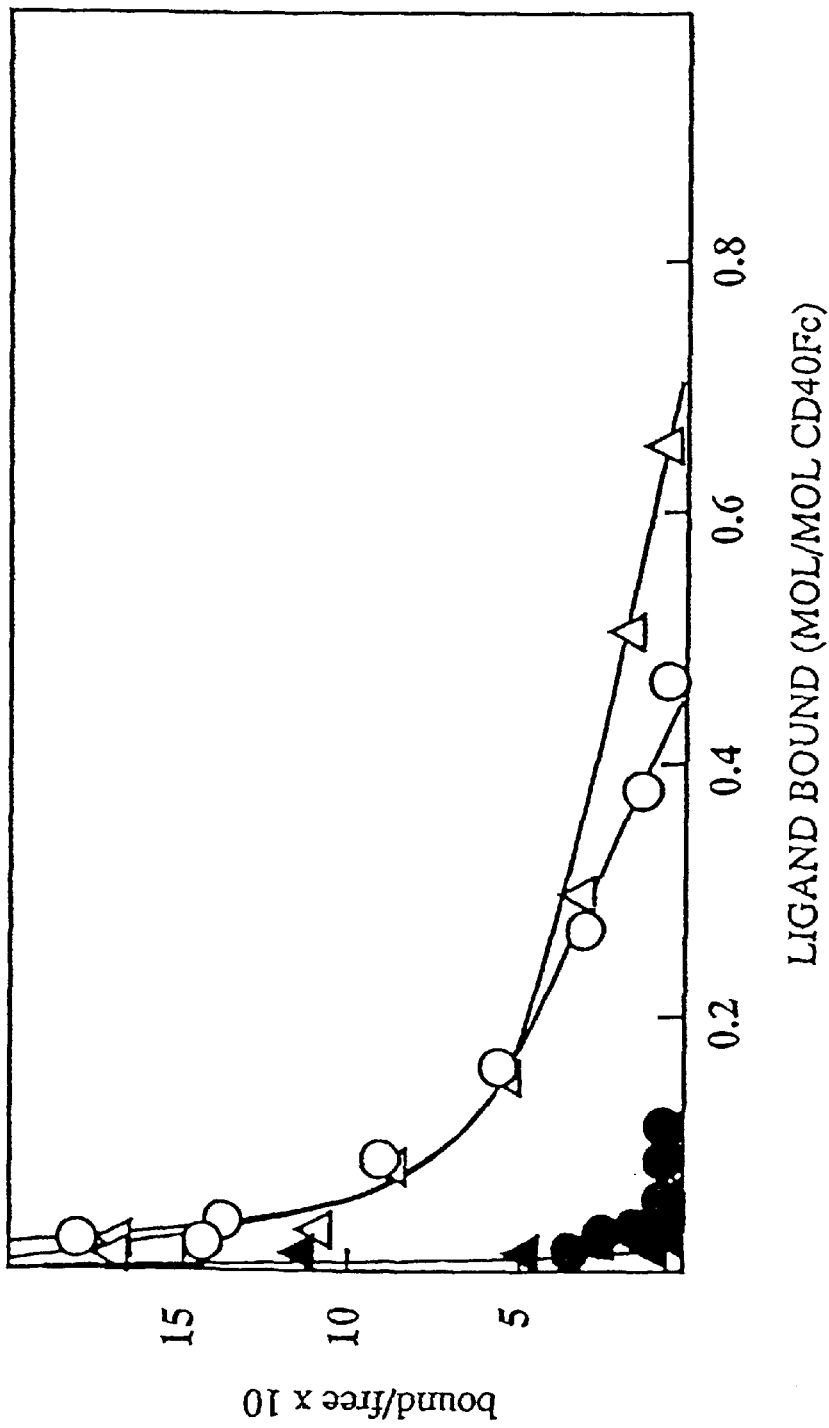
FIG. 18 presents the binding of trimeric human and murine CD40-L and dimeric human and murine CD40-L to C40/Fc as determined in a biosensor assay.
Figure 19A:
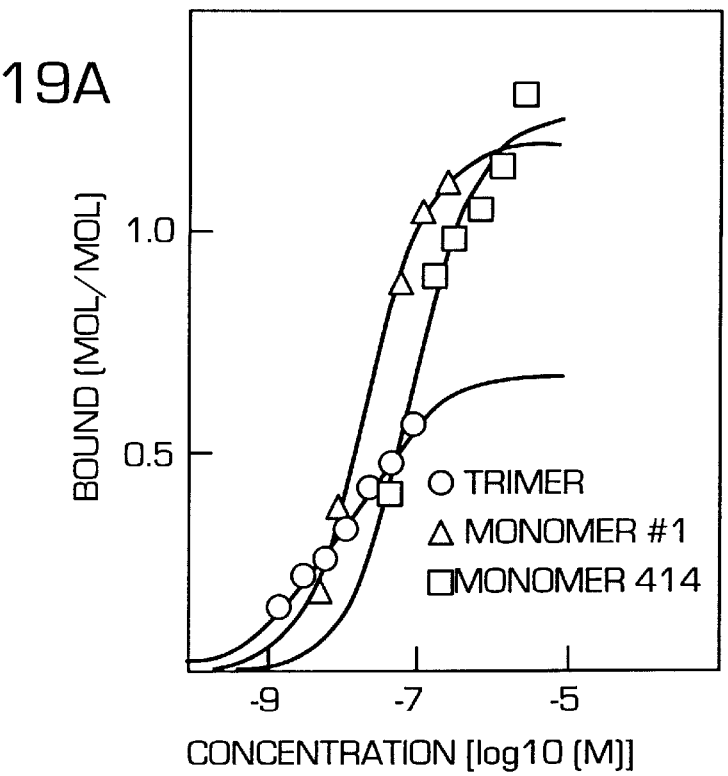
FIGS. 19A–19B illustrate the binding of trimeric human CD40-L and two preparations of monomeric human CD40-L to C40/Fc as determined in a biosensor assay.
Figure 19B:
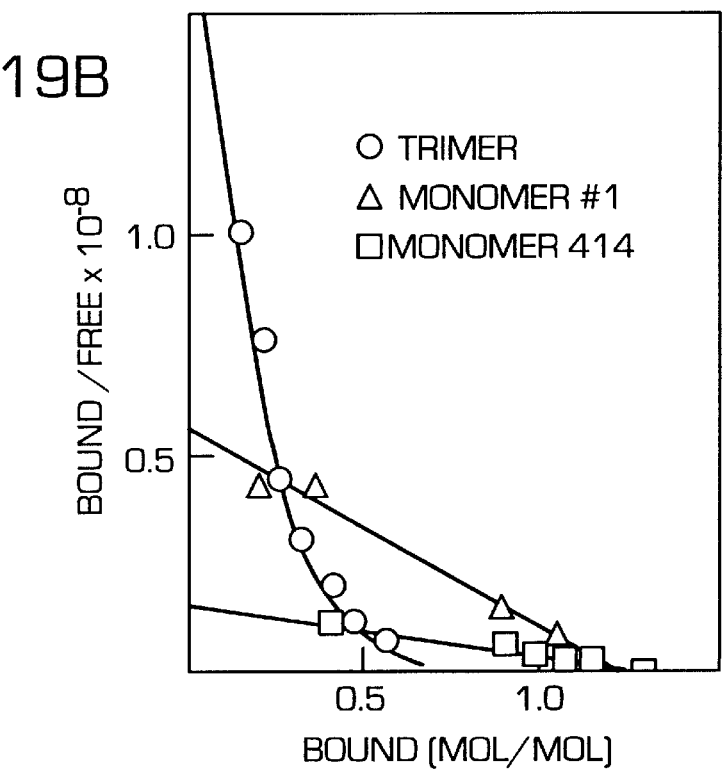

The biosensor chips were coated with goat anti-human $IgG_1$ Fc, which was used to bind CD40/Fc (prepared as described in Example 1) to the chip. The different constructs of CD40-L were then added at increasing concentrations; the chip was regenerated between the different constructs by the addition of sodium hydroxide. Two separate experiments were performed. In the first, the binding of a dimeric human CD40-L (Example 14), trimeric human CD40-L (Example 15), dimeric murine CD40-L (prepared substantially as described in Example 14 for human CD40-L/FC) and trimeric murine CD40-L (prepared substantially as described for the human CD40-L in Example 15) were compared. In the second experiment, the binding of trimeric human CD40-L was compared to the binding of two different preparations of monomeric human CD40-L prepared as described in Example 18. The resultant data were analyzed to determine the affinity and association rate constants of the different CD40-L constructs. Results are shown in Table 12 below, and in FIGS. 18 and 19A–19B.

TABLE 12

Binding of CD40-L to CD40/Fc

|  | Site 1 (mol/mol CD40/Fc) | $K_1$ $(M^{-1})$ | Site 2 (mol/mol CD40/Fc) | $K_2$ $(M^{-1})$ |
| --- | --- | --- | --- | --- |
| Human Trimer | 0.04 ± 0.02 | $5 \pm 3 \times 10^9$ | 0.68 ± 0.07 | $7.5 \pm 2.5 \times 10^7$ |
| Human Dimer | 0.013 ± 0.002 | $1.6 \pm 0.7 \times 10^{11}$ | 0.049 ± 0.004 | $7.0 \pm 2.1 \times 10^8$ |
| Murine Trimer | 0.02 ± 0.003 | $6 \pm 3 \times 10^{10}$ | 0.44 ± 0.02 | $1.6 \pm 0.2 \times 10^8$ |
| Murine Dimer | 0.05 ± 0.02 | $7 \pm 4 \times 10^9$ | 0.14 ± 0.23 | $4.0 \pm 1.0 \times 10^7$ |
| Human Trimer | 0.26 | $6.6 \times 10^8$ | 0.41 | $2.6 \times 10^7$ |
| Monomer #1 | Not Detected | Not Detected | 1.20 | $4.6 \times 10^7$ |
| Monomer #2 | Not Detected | Not Detected | 1.27 | $1.1 \times 10^7$ |

Analysis of the data indicated that a CD40-L monomer comprising solely the portion of the extracellular domain most homologous to TNF was capable of binding CD40, although with somewhat lower affinity than oligomeric CD40-L. An analysis of the ratio of binding in the second experiment demonstrated that there are twice as many CD40-L monomer units bound per CD40Fc molecule as trimeric CD40-L, confirming that two monomers of CD40-L bind one CD40/Fc dimer and one trimeric CD40-L binds one CD40/Fc dimer.

EXAMPLE 23

This example demonstrates that CD40-L enhances the generation of cytotoxic T lymphocytes (CTL) in mixed lymphocyte cultures (MLC). A 4-hour $^{51}$Cr release assay was used to assess the cytolytic activity of human T cells essentially as described in Alderson et al., *J. Exp. Med.* 172:577 (1990). Briefly, freshly isolated peripheral blood mononuclear cells from one donor were cultured in MLC (mixed lymphocyte culture) with irradiated, allogeneic stimulating cells (target cells), either in the presence or absence of membrane-bound CD40-L. $^{51}$Cr-labeled target cells were prepared by incubating tumor cell lines, or three day PHA blasts from a second donor, with 100 µCi of $^{51}$Cr for one hour at 37° C.

Cell cultures to be assessed for cytolytic activity were washed twice in culture medium and serially diluted in 96-well V-bottom plates (Costar). $^{51}$Cr-labeled target cells ($2 \times 10^3$) were added to each well (total volume of 200 µl/well), and the plates were incubated for four hours at 37° C. After incubation, the plates were centrifuged at 150 g for five minutes, and harvested using a Skatron SCS harvesting system (Skatron, Sterling, Va.). $^{51}$Cr content of the supernatants was determined using a Micromedic ME Plus gamma scintillation counter (Micromedic, Huntsville, Tenn.). Percent specific $^{51}$Cr release was calculated according to the formula 100×(experimental cpm−spontaneous cpm)/(maximum cpn/spontaneous cpm) where spontaneous cpm=cpm released in the absence of effector cells and maximum cpm=cpm released in the presence of 1N HCl. The results of this experiment indicated that membrane-bound CD40-L enhanced CTL generation. A polyclonal anti-IL-2 antiserum capable of neutralizing 10 ng/ml of IL-2 at a 1:500 dilution was used to demonstrate that CD40-L enhancement of CTL had both IL-2 dependent and IL-2 independent components.

Similar experiments were performed to analyze the phenotype of the responding cells. T cells were purified by rosetting with 2-aminoethylisothiouronium bromide hydrobromide-treated sheep red blood cells. CD4+ and CD8+ populations were further purified using immunomagnetic selection using a MACS (Milenyi Biotec, Sunnyvale, Calif.) according to the manufacturer's protocol. Whereas IL-2 enhanced CTL generation by PBMC, purified T cells and CD8+ T cells, CD40-L enhanced CTL generation by PBMC and purified T cells, but not by CD8+ T cells. Analysis of cytokine secretion using a CTLL assay for IL-2 or an ELISA for IFN-γ indicated that CD4+ cells costimulated with CD40-L produced 5 to 10-fold more IFN-γ and IL-2 than CD8+ cells. Moreover, CD40-L stimulated CD4+ cells were induced to become cytolytic in a lectin-mediated killing assay, whereas IL-2 costimulated both CD8+ and CD4+ cells to become cytolytic.

These data demonstrate that, in addition to accessory molecules expressed by antigen presenting cells, membrane proteins may be important in T—T cell interactions. The function of CD40-L may be to enhance the expansion of activated T cells within a proliferating T cell clone in a paracrine fashion.

EXAMPLE 24

This example illustrates preparation of a number of muteins of a CD40 ligand/zipper domain fusion protein. Mutations for constructs to be expressed in yeast (mutants 14, 18, 32, 41, 43, 10PP and 18PP) were generated by PCR misincorporation (Mulrad et al *Yeast* 8:79, 1992), and selected based on an apparent increase in secretion as improved secretion mutants.

Mutants 14, 18, 32, 41, and 43 were isolated in *S. cerevisiae*. Mutants 10PP and 18PP were isolated in *P. pastoris*. Mutations for constructs to be expressed in mammalian cells (FL194.W, 194.W, LZ12V, 215.T, 255.F, and 194.S) were also prepared using PCR, and were either the result of site-directed mutagenesis or were the random product of PCR. The types of mutations obtained and their effect on activity (ability to bind CD40 in a solid phase binding assay substantially as described in Example 16) are shown in Table 13 below.

TABLE 13

Mutations present in the CD40 ligand/zipper domain fusion protein

| Mutant No.: | Zipper Domain Mutation[a] | CD40L Domain Mutations[b] | Activity | Type of Mutant |
|---|---|---|---|---|
| 14 | I12N | K260N | + | random mutant |
| 18 | L13P | A130P, R181Q | + | random mutant |
| 32 | I12N | Q121P | + | random mutant |
| 41 | I5M, I16T | NA | + | random mutant |
| 43 | I16N | T134S, K164I, Q186L, N210S | + | random mutant |
| 10PP | I9N, K27R | NA[d] | + | random mutant |
| 18PP | L13P | NA | + | random mutant |
| LZ12.V | I12V | Deletion of aa 1–112 | + | PCR; random |
| 215.T | NA | Deletion of aa 1–112; A215T | + | PCR; random |
| 255.F | NA | Deletion of aa 1–112; S215F | − | PCR; site-directed |
| FL194W | NA | C194W | + | PCR; site-directed |
| 194.W | NA | Deletion of aa 1–112; C194W | + | PCR; site-directed |
| 194.S | NA | Deletion of aa 1–112; C194S | ND[e] | PCR; site-directed |
| 194.A | NA | Deletion of aa 1–112; C194A | ND[e] | PCR; site-directed |
| 194.D | NA | Deletion of aa 1–112; C194D | ND[e] | PCR; site-directed |
| 194.K | NA | Deletion of aa 1–112; C194K | ND[e] | PCR; site-directed |

[a]: Mutations are given as the residue present in the native peptide, the residue number, and the residue present in the mutein. Residue numbers for zipper domain mutations are relative to SEQ ID NO: 17.
[b]: Residue numbers for mutations in the CD40L domain are relative to SEQ ID NO: 12.
[c]: Mutant 10PP also contained mutations in regions other than CD40L domain or the zipper domain (T-4S, D-2P, relative to SEQ ID NO: 21).
[d]: Not applicable
[e]: Not done Mutant 18PP had only a single mutation in the molecule, which was sufficient to affect secretion in yeast. Mutant 41 had two mutations, both of which were in the isoleucine residues of the zipper domain. The mutations in the zipper improve secretion from yeast without apparent effect on activity. Mutant 194.W was expressed in yeast cells and purified either by a combination of ion exchange chromatography steps (194.W (c)) or by affinity chromatography (194.W (a)) using a monoclonal antibody that binds the oligomerizing zipper moiety. oligomerizing zipper moiety. The yeast-expressed mutant (194.W) exhibited greater affinity for CD40 in a biosensor assay performed substantially as described in Example 22, and exhibited greater biological activity than wild type CD40 ligand/zipper domain fusion protein (WT) expressed in yeast, in a B cell proliferation assay. These results are shown in Table 14.

TABLE 14

Comparison of WT and 194.W for Receptor Binding and B-cell Proliferation

| | Affinity | B-cell proliferation ($U/\mu g^a$) | |
|---|---|---|---|
| | $K_a$ ($M^{-1}$) | Experiment 1 | Experiment 2[d] |
| WT | $7.7 \times 10^7$ | 77[b] | 15 |
| 194.W (c) | $1.8 \times 10^9$ | 171 | 116 |

TABLE 14-continued

Comparison of WT and 194.W for Receptor Binding and B-cell Proliferation

| | Affinity | B-cell proliferation ($U/\mu g^a$) | |
|---|---|---|---|
| | $K_a$ ($M^{-1}$) | Experiment 1 | Experiment 2[d] |
| 194.W (a) | ND[c] | ND | 161 |

[a]: A unit (U) is the concentration that induces half-maximal proliferation
[b]: Average from two independent preparations
[c]: Not done
[d]: Average of two assays Moreover, FL194W expresssed in mammalian cells also demonstrated higher binding that WT CD40-L in a semi-quantitative western blot analysis.

Additional constructs were prepared by substituting the lung surfactant protein D (SPD) trimerization domain (SEQ ID NO:24; Hoppe, et al., *FEBS Letters* 344:191, 1994) in place of the trimer-forming zipper of SEQ ID NO:17. This construct is expressed in *S. cerevisiae* and in mammalian cells at low levels. Activity is determined as described previously; various mutants based on such constructs can also be prepared to optimize secretion or other product characteristics, as described above.

What is claimed is:

1. A recombinant CD40-L polypeptide that binds CD40, and comprises an extracellular region, a transmembrane region and a cytoplasmic region, wherein said polypeptide comprises amino acids 1 through 261 of SEQ ID NO:12.

2. A pharmaceutical composition comprising a recombinant CD40L polypeptide according to claim 1, and a suitable diluent or carrier.

3. A recombinant CD40-L polypeptide that binds CD40, and comprises an extracellular region, a transmembrane region and a cytoplasmic region, wherein said polypeptide is encoded by a DNA molecule comprising nucleotides 46 through 828 of SEQ ID NO:11.

4. A pharmaceutical composition comprising a recombinant CD40L polypeptide according to claim 3, and a suitable diluent or carrier.

5. A recombinant CD40-L polypeptide that binds CD40, and comprises an extracellular region, a transmembrane region and a cytoplasmic region, wherein said polypeptide comprises amino acids 1 through 260 of SEQ ID NO:2.

6. A pharmaceutical composition comprising a recombinant CD40L polypeptide according to claim 5, and a suitable diluent or carrier.

7. A recombinant CD40-L polypeptide that binds CD40, and comprises an extracellular region, a transmembrane region and a cytoplasmic region, wherein said polypeptide is encoded by a DNA molecule comprising nucleotides 1 through 780 of SEQ ID NO:1.

8. A pharmaceutical composition comprising a recombinant CD40L polypeptide according to claim 7, and a suitable diluent or carrier.

* * * * *